United States Patent
Makriyannis et al.

(10) Patent No.: US 8,410,097 B2
(45) Date of Patent: *Apr. 2, 2013

(54) HETEROPYRROLE ANALOGS ACTING ON CANNABINOID RECEPTORS

(75) Inventors: Alexandros Makriyannis, Watertown, MA (US); Rajesh Thotapally, Pune (IN); Venkata Kiran Rao Vemuri, Boston, MA (US); Teresa Olszewska, Gdansk (PL)

(73) Assignee: University of Connecticut, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/334,163

(22) Filed: Dec. 22, 2011

(65) Prior Publication Data

US 2012/0095047 A1 Apr. 19, 2012

Related U.S. Application Data

(62) Division of application No. 11/813,546, filed as application No. PCT/US2006/000720 on Jan. 10, 2006, now Pat. No. 8,084,451.

(60) Provisional application No. 60/642,544, filed on Jan. 10, 2005.

(51) Int. Cl.
*A61K 31/41* (2006.01)
*A61K 31/405* (2006.01)
*C07D 207/00* (2006.01)
*C07D 209/00* (2006.01)

(52) U.S. Cl. ........ 514/241; 514/310; 514/381; 514/406; 548/253; 548/312.4; 548/365.7

(58) Field of Classification Search .................. 514/241, 514/310, 381, 406; 548/253, 312.4, 365.7
See application file for complete search history.

(56) References Cited

U.S. PATENT DOCUMENTS

| | | | |
|---|---|---|---|
| 4,732,900 A | 3/1988 | Weber et al. | |
| 5,155,124 A | 10/1992 | Kimata et al. | |
| 5,208,231 A | 5/1993 | Kimata et al. | |
| 5,462,960 A | 10/1995 | Barth et al. | |
| 6,288,061 B1 * | 9/2001 | Sueoka et al. | 514/235.8 |
| 7,119,108 B1 | 10/2006 | Makriyannis et al. | |
| 7,393,842 B2 | 7/2008 | Makriyannis et al. | |
| 7,745,440 B2 | 6/2010 | Makriyannis et al. | |
| 8,084,451 B2 * | 12/2011 | Makriyannis et al. | 514/241 |

FOREIGN PATENT DOCUMENTS

| | | |
|---|---|---|
| WO | WO03/007887 A2 | 1/2003 |
| WO | WO03/027076 A2 | 4/2003 |
| WO | WO2005/000820 A2 | 1/2005 |

OTHER PUBLICATIONS

Jarbe T. U.; Lemay B. J.; Vemuri V. K.; Vadivel S. K.; Zvonok A.; Makriyannis A. Central mediation and differential blockade by cannabinergics of the discriminative stimulus effects of the cannabinoid CB(1) receptor antagonist rimonabant in rats. Psychopharmacology (Berl). 2011 DOI 10.1007/s00213-011-2226-3).

Cluny N. L.; Chambers A. P.; Vemuri V. K.; Wood J. T.; Eller L. K.; Freni C.; Reimer R. A.; Makriyannis A.; Sharkey K. A. The neutral cannabinoid CB receptor antagonist AM4113 regulates body weight through changes in energy intake in the rat. Pharmacol Biochem Behav. 2011, 97, (3), 537-43.

Randall P. A.; Vemuri V. K.; Segovia K. N.; Torres E. F.; Hosmer S.; Nunes E. J.; Santerre J. L.; Makriyannis A.; Salamone J. D. The novel cannabinoid CB1 antagonist AM6545 suppresses food intake and food-reinforced behavior. Pharmacol Biochem Behav. 2010, 97, (1), 179-84.

Jarbe T. U.; LeMay B. J.; Olszewska T.; Vemuri V. K.; Wood J. T.; Makriyannis A. Intrinsic effects of AM4113, a putative neutral CB1 receptor selective antagonist, on open-field behaviors in rats. Pharmacol Biochem Behav. 2008, 91, (1), 84-90.

Hodge J.; Bow J. P.; Plyler K. S.; Vemuri V. K.; Wisniecki A.; Salamone J. D.; Makriyannis A.; McLaughlin P. J. The cannabinoid CB1 receptor inverse agonist AM 251 and antagonist AM 4113 produce similar effects on the behavioral satiety sequence in rats. Behav Brain Res. 2008, 193, (2), 298-305.

Bergman J.; Delatte M. S.; Paronis C. A.; Vemuri K.; Thakur G. A.; Makriyannis A. Some effects of CB1 antagonists with inverse agonist and neutral biochemical properties. Physiol Behav. 2008, 93, (4-5), 666-70.

Sink K. S.; Vemuri V. K.; Wood J.; Makriyannis A.; Salamone J. D. Oral bioavailability of the novel cannabinoid CB1 antagonist AM6527: effects on food-reinforced behavior and comparisons with AM4113. Pharmacol Biochem Behav. 2009, 91, (3), 303-6.

Cluny N. L.; Vemuri V. K.; Chambers A. P.; Limebeer C. L.; Bedard H.; Wood J. T.; Lutz B.; Zimmer A.; Parker L. A.; Makriyannis A.; Sharkey K. A. A novel peripherally restricted cannabinoid receptor antagonist, AM6545, reduces food intake and body weight, but does not cause malaise, in rodents. Br J Pharmacol. 2010, 161, (3), 629-42.

Limebeer C. L.; Vemuri V. K.; Bedard H.; Lang S. T.; Ossenkopp K. P.; Makriyannis A.; Parker L. A. Inverse agonism of cannabinoid CB1 receptors potentiates LiCl-induced nausea in the conditioned gaping model in rats. Br J Pharmacol. 2010, 161, (2), 336-49.

Tam J.; Vemuri V. K.; Liu J.; Batkai S.; Mukhopadhyay B.; Godlewski G.; Osei-Hyiaman D.; Ohnuma S.; Ambudkar S. V.; Pickel J.; Makriyannis A.; Kunos G. Peripheral CB1 cannabinoid receptor blockade improves cardiometabolic risk in mouse models of obesity. J Clin Invest. 2010, 120, (8), 2953-66.

(Continued)

*Primary Examiner* — Susannah Chung

(74) *Attorney, Agent, or Firm* — Alix, Yale & Ristas, LLP

(57) ABSTRACT

Disclosed are biologically active hetero pyrrole analogs such as imidazoles, thiazoles, oxazoles and pyrazoles capable of interacting with the CB1 and/or the CB2 cannabinoid receptors. One aspect discloses hetero pyrrole analogs acting as antagonists for the CB1 and/or the CB2 receptors. Another aspect discloses hetero pyrrole analogs having selectivity for the CB1 or CB2 cannabinoid receptor. Also disclosed are pharmaceutical preparations employing the disclosed analogs and methods of administering therapeutically effective amounts of the disclosed analogs to provide a physiological effect.

20 Claims, No Drawings

OTHER PUBLICATIONS

Sink K. S.; Segovia K. N.; Collins L. E; Markus E. J.; Vemuri V. K.; Makriyannis A.; Salamone J. D. The CB1 inverse agonist AM251, but not the CB1 antagonist AM4113, enhances retention of contextual fear conditioning in rats. Pharmacol Biochem Behav. 2010, 95, (4), 479-84.

Sink K. S.; Segovia K. N.; Sink J.; Randall P. A.; Collins L. E.; Correa M.; Markus E. J.; Vemuri V. K.; Makriyannis A.; Salamone J. D. Potential anxiogenic effects of cannabinoid CB1 receptor antagonists/inverse agonists in rats: comparisons between AM4113, AM251, and the benzodiazepine inverse agonist FG-7142. Eur Neuropsychopharmacol. 2010, 20, (2), 112-22.

Storr M. A.; Bashashati M.; Hirota C.; Vemuri V. K.; Keenan C. M.; Duncan M.; Lutz B.; Mackie K.; Makriyannis A.; Macnaughton W. K.; Sharkey K. A. Differential effects of CB(1) neutral antagonists and inverse agonists on gastrointestinal motility in mice. Neurogastroenterol Motil. 2010, 22, (7), 787-96, e223.

Chambers A. P.; Vemuri V. K.; Peng Y.; Wood J. T.; Olszewska T.; Pittman Q. J.; Makriyannis A.; Sharkey K. A. A neutral CB1 receptor antagonist reduces weight gain in rat. Am J Physiol Regul Integr Comp Physiol. 2007, 293, (6), R2185-93.

Sink K. S.; McLaughlin P. J.; Wood J. A.; Brown C.; Fan P.; Vemuri V. K.; Peng Y.; Olszewska T.; Thakur G. A.; Makriyannis A.; Parker L. A.; Salamone J. D. The novel cannabinoid CB1 receptor neutral antagonist AM4113 suppresses food intake and food-reinforced behavior but does not induce signs of nausea in rats. Neuropsychopharmacology. 2008, 33, (4), 946-55.

Patani G. A.; LaVoie, E. J. Bioisosterism: A Rational Approach in Drug Design. Chem Rev, 1996, vol. 96 (8), especially p. 3147.

* cited by examiner

HETEROPYRROLE ANALOGS ACTING ON CANNABINOID RECEPTORS

CROSS REFERENCE TO RELATED APPLICATION

This application is a divisional of U.S. patent application Ser. No. 11/813,546 filed Sep. 16, 2008, now U.S. Pat. No. 8,084,451 which is the U.S. National Phase of International Application No. PCT/US06/000720 filed Jan. 10, 2006, which claims priority to U.S. Provisional Application No. 60/642,544 filed Jan. 10, 2005, the contents of each of which are incorporated herein by reference in their entirety.

STATEMENT REGARDING FEDERALLY SPONSORED RESEARCH OR DEVELOPMENT

This invention was made with Government support under Grant No. DA7215 awarded by the National Institute on Drug Abuse. The Government may have certain rights in the invention.

FIELD OF THE INVENTION

The present invention relates generally to biologically active hetero pyrrole analogs such as imidazoles, thiazoles, oxazoles and pyrazoles capable of interacting with the CB1 and/or the CB2 cannabinoid receptors. One aspect of the invention is concerned with new and improved hetero pyrrole analogs acting as antagonists for the CB1 and/or the CB2 receptors. Another aspect of the invention is concerned with new and improved hetero pyrrole analogs having selectivity for the CB1 or CB2 cannabinoid receptor. Still other aspects of the invention are concerned with pharmaceutical preparations employing the inventive analogs and methods of administering therapeutically effective amounts of the inventive analogs to provide a physiological effect.

BACKGROUND OF THE INVENTION

Marijuana (*Cannabis sativa*) and derivatives have been used for medicinal and recreational purposes. The major active constituent extracted from *Cannabis sativa* is the classical cannabinoid $\Delta^9$-Tetrahydrocannabinol ($\Delta^9$-THC). The effects of such cannabinoids are due to an interaction with specific high-affinity receptors. Presently, two cannabinoid receptors have been characterized: CB1, a central receptor found in the mammalian brain and a number of other sites in peripheral tissues; and CB2, a peripheral receptor found principally in cells related to the immune system. The CB1 receptor is believed to mediate the psychoactive properties associated with classical cannabinoids. Characterization of these receptors has been made possible by the development of specific synthetic ligands such as the agonists WIN 55212-2 and CP 55,940.

In addition to acting at the cannabinoid receptors, cannabinoids such as $\Delta^9$-THC also affect cellular membranes, thereby producing undesirable side effects such as drowsiness, impairment of monoamine oxidase function and impairment of non-receptor mediated brain function. The addictive and psychotropic properties of some cannabinoids also limit their therapeutic value.

International Publication number WO 03/007887 A2 to Finke et al describes imidazole derivatives alleged to have binding affinity for the central cannabinoid receptor. International Publication number WO 03/027076 A2 to Kruse et al also describes some imidazole derivatives alleged to have binding affinity for cannabinoid receptors.

SUMMARY OF THE INVENTION

Briefly stated, one embodiment of the invention is concerned with new and improved cannabimimetic (cannabinoid like) imidazole analogs. The inventive cannabimimetic imidazole ligands of this embodiment can be represented by general formula I:

I

R4
A
B
R3
N1  5  4
    3
R1  2  N   O
R2

A comprises a direct bond, O or —(CH$_2$)$_j$N(R5).

B comprises a direct bond, O or N(R5).

R5 is hydrogen, alkyl or substituted alkyl and I is 0 or 1.

In a variation of formula I R1 and R2 each independently comprise —(CH$_2$)$_n$—Z.

n is an integer from 0 to about 7.

Z comprises H, halogen, N$_3$, NCS, CN, NO$_2$, NX$_1$X$_2$, OX$_3$, OAc, O-acyl, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, alkoxy, alkylmercapto, alkylamino, di-alkylamino, alkylsulfinyl or alkylsulfonyl.

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members.

X$_3$ comprises H, alkyl, hydroxyloweralkyl, or alkyl-NX$_1$X$_2$.

j is an integer from 0 to about 6.

In a variation of formula I R1 and R2 each independently comprise —(CH$_2$)$_n$—Z.

n is an integer from 0 to about 7.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of formula I R1 and R2 each independently comprise —(CH$_2$)$_n$—Z.

n is an integer from 0 to about 7.

Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —$(CH_2)_n$— group and the Z group can be any available ring carbon atom or any available ring nitrogen atom.

In a variation of formula I R1 and R2 each independently comprise —$(CH_2)_n$—Z.

n is an integer from 0 to about 7.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula I, R1 and R2 each independently comprise —$(CH_2)_n$—Z.

n is an integer from 0 to about 7.

Z comprises

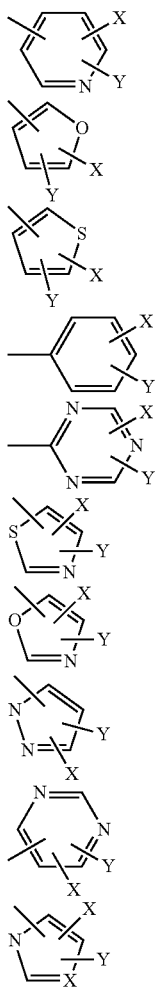

wherein X and Y each independently comprise H, halogen, $N_3$, NCS, CN, $NO_2$, $NX_1X_2$, $OX_3$, OAc, O-acyl, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, alkyl, alcohol, alkoxy, alkylmercapto, alkylamino, di-alkylamino, alkylsulfinyl, alkylsulfonyl or methylene dioxy when Z comprises a structure having two adjacent carbon atoms.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

In a variation of formula I R1 and R2 each independently —$(CH_2)_n$—Z.

n is an integer from 0 to about 7.

Z comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms.

In a variation of formula I R1 and R2 each independently comprise —$(CH_2)_n$—Z.

n comprises an integer from 0 to about 7.

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 3 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members.

In a variation of formula I R1 and R2 each independently comprise —$(CH_2)_m$-$Q_1$-$(CH_2)_n$—Z.

$Q_1$ comprises N, O, S, —CH═CH—, —CO, $SO_2$ or $OSO_2$.

m is an integer from 1 to about 7 n is an integer from 0 to about 7.

Z comprises H, halogen, $N_3$, NCS, CN, $NO_2$, $NX_1X_2$, $OX_3$, OAc, O-acyl, O-aroyl, $O(CH_2)_jOH$, $O(CH_2)_jOX_3$, $O(CH_2)_j$ $NX_1X_2$, NH-acyl, NH-aroyl, CHO, C(halogen)$_3$, $COOX_3$, $SO_3H$, $SO_2NX_1X_2$, $CONX_1X_2$, alkyl, alkoxy, alkylmercapto, alkylamino, alkylsulfinyl or alkylsulfonyl.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

j is an integer from 0 to about 6.

In a variation of formula I R1 and R2 each independently comprise -$Q_2$-$(CH_2)_n$—Z.

$Q_2$ is optionally present and if present comprises —$CH_2$—N, —$CH_2$—O, —$CH_2$—S, —$CH_2$—$SO_2$ or —$CH_2$—$OSO_2$.

n is an integer from 0 to about 7.

Z comprises H, halogen, $N_3$, NCS, CN, $NO_2$, $NX_1X_2$, $OX_3$, OAc, O-acyl, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, alkoxy, alkylmercapto, alkylamino, di-alkylamino, alkylsulfinyl or alkylsulfonyl.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

j is an integer from 0 to about 6.

In a variation of formula I R1 and R2 each independently comprise —$(CH_2)_m$-$Q_1$-$(CH_2)_n$—Z.

$Q_1$ comprises N, O, S, CH=CH, C≡C, CO, $SO_2$ or $OSO_2$.

m is an integer from 1 to about 7 n is an integer from 0 to about 7.

Z comprises a bicyclic ring, a heterobicyclic ring, a tricyclic ring, a heterotricyclic ring, a polycyclic ring or a heteropolycyclic ring.

In a variation of formula I R1 and R2 each independently comprise —$(CH_2)_m$-$Q_1$-$(CH_2)_n$—Z.

$Q_1$ comprises N, O, S, CH=CH, C≡C, CO, $SO_2$ or $OSO_2$.

m is an integer from 1 to about 7.

n is an integer from 0 to about 7.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; a bicyclic ring, a heterobicyclic ring, a tricyclic ring, a heterotricyclic ring, a polycyclic ring, a heteropolycyclic ring or any above group substituted on at least one available ring atom by an alkyl group or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula I R1 and R2 each independently comprise —$(CH_2)_m$-$Q_1$-$(CH_2)_n$—Z.

$Q_1$ comprises N, O, S, CH=CH, C≡C, CO, $SO_2$ or $OSO_2$.

m is an integer from 1 to about 7.

n is an integer from 0 to about 7.

Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —$(CH_2)_n$— group and the Z group can be any available ring carbon atom or any available ring nitrogen atom.

In a variation of formula I R1 and R2 each independently comprise —$(CH_2)_m$-$Q_1$-$(CH_2)_n$—Z.

$Q_1$ comprises N, O, S, CH=CH, C≡C, CO, $SO_2$ or $OSO_2$.

m is an integer from 1 to about 7.

n is an integer from 0 to about 7.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula I R1 and R2 each independently comprise —$(CH_2)_m$-$Q_1$-$(CH_2)_n$—Z.

$Q_1$ comprises N, O, S, CH=CH, C≡C, CO, $SO_2$ or $OSO_2$ m is an integer from 1 to about 7.

n is an integer from 0 to about 7.

Z comprises

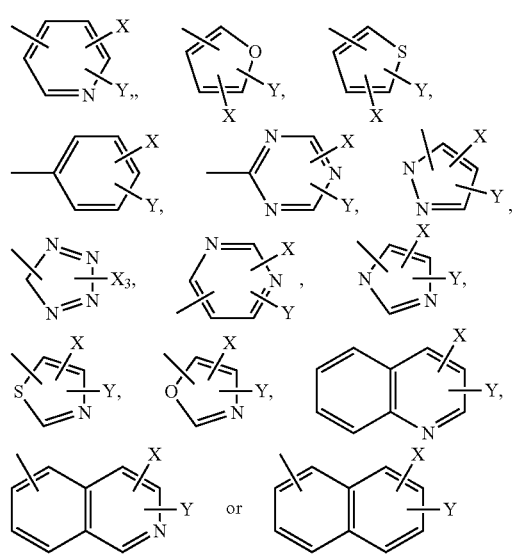

wherein X and Y each independently comprise H, halogen, $N_3$, NCS, CN, $NO_2$, $NX_1X_2$, $OX_3$, OAc, O-acyl, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, alkyl, alcohol, alkoxy, alkylmercapto, alkylamino or di-alkylamino, alkylsulfinyl, alkylsulfonyl, or methylene dioxy when Z comprises a structure having two adjacent carbon atoms.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

In a variation of formula I R1 and R2 each independently comprise. —$(CH_2)_m$-$Q_1$-$(CH_2)_n$—Z.

$Q_1$ comprises N, O, S, CH=CH, C≡C, CO, $SO_2$ or $OSO_2$.

m is an integer from 1 to about 7.

n is an integer from 0 to about 7.

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members.

In a variation of formula I R1 and R2 each independently comprise —$(CH_2)_m$-$Q_1$-$(CH_2)_n$—Z.

$Q_1$ comprises N, O, S, CH=CH, C≡C, CO, $SO_2$ or $OSO_2$.

m is an integer from 1 to about 7.

n is an integer from 0 to about 7.

Z comprises

[chemical structures]

In a variation of formula I R1 and R2 each independently comprise -T-$(CH_2)_n$—Z.

n comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Z comprises H, halogen, $N_3$, NCS, CN, $NO_2$, $NX_1X_2$, $OX_3$, OAc, O-acyl, O-aroyl, $O(CH_2)_j$OH, $O(CH_2)_j OX_3$, $O(CH_2)_j NX_1X_2$, NH-acyl, NH-aroyl, CHO, C(halogen)$_3$, $COOX_3$, $SO_3H$, $SO_2NX_1X_2$, $CONX_1X_2$, alkoxy, alkylmercapto, alkylamino, di-alkylamino, alkylsulfinyl, or alkylsulfonyl.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

j is an integer from 0 to about 6.

In a variation of formula I R1 and R2 each independently comprise -T-$(CH_2)_n$—Z.

n comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula I R1 and R2 each independently comprise -T-$(CH_2)_n$—Z.

n comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula I R1 and R2 each independently comprise -T-$(CH_2)_n$—Z.

n comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Z comprises

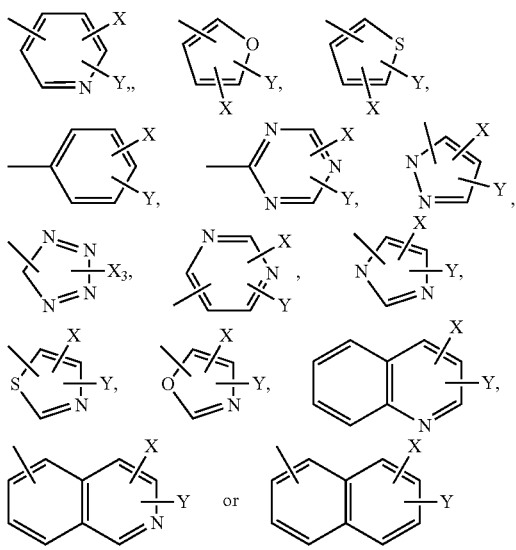

wherein X and Y each independently comprise H, halogen, $N_3$, NCS, CN, $NO_2$, $NX_1X_2$, $OX_3$, OAc, O-acyl, O-aroyl, NH-acyl, NH-aroyl, CHO, C(halogen)$_3$, COOX$_3$, SO$_3$H, SO$_2$NX$_1$X$_2$, CONX$_1$X$_2$, alkyl, alcohol, alkoxy, alkylmercapto, alkylamino, di-alkylamino, alkylsulfinyl, alkylsulfonyl or methylene dioxy when Z comprises a structure having two adjacent carbon atoms.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-NX$_1$X$_2$.

In a variation of formula I R1 and R2 each independently comprise -T-$(CH_2)_n$—Z.

n comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members.

In a variation of formula I R1 and R2 each independently comprise -T-$(CH_2)_n$-$Q_1$-$(CH_2)_m$.

each n independently comprises an integer from 0 to about 7.

m is an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

$Q_1$ comprises NH, O, S, CH=CH, C≡C, CO, SO$_2$ or OSO$_2$.

Z comprises H, halogen, $N_3$, NCS, CN, $NO_2$, $NX_1X_2$, $OX_3$, OAc, O-acyl, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, alkyl, alcohol, alkoxy, alkylmercapto, alkylamino or di-alkylamino, alkylsulfinyl or alkylsulfonyl.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-NX$_1$X$_2$.

j is an integer from 0 to about 6.

In a variation of formula I R1 and R2 each independently comprise -T-$(CH_2)_n$-$Q_1$-$(CH_2)_m$.

each n independently comprises an integer from 0 to about 7.

m is an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

$Q_1$ comprises NH, O, S, CH=CH, C≡C, CO, SO$_2$ or OSO$_2$.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_m$ group and the Z group can be any available ring carbon atom or any available ring nitrogen atom.

In a variation of formula I R1 and R2 each independently comprise -T-$(CH_2)_n$-$Q_1$-$(CH_2)_m$.

each n independently comprises an integer from 0 to about 7.

m is an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

$Q_1$ comprises NH, O, S, CH=CH, C≡C, CO, $SO_2$ or $OSO_2$.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_m$— group and the Z group can be any available ring carbon atom or any available ring nitrogen atom.

In a variation of formula I R1 and R2 each independently comprise -T-$(CH_2)_n$-$Q_1$-$(CH_2)_m$.

each n independently comprises an integer from 0 to about 7.

m is an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

$Q_1$ comprises NH, O, S, CH=CH, C≡C, CO, $SO_2$ or $OSO_2$.

Z comprises

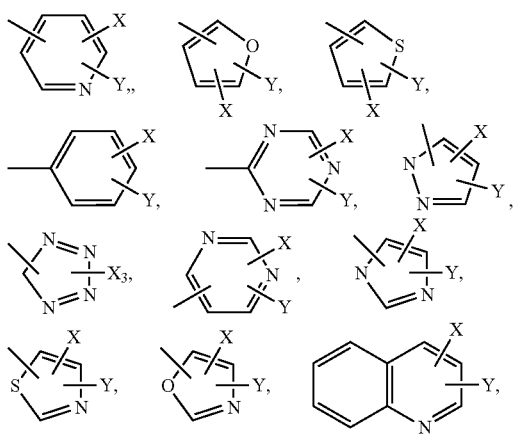

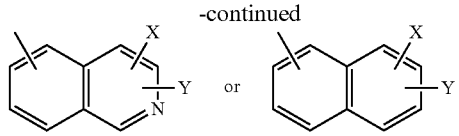

wherein X and Y each independently comprise H, halogen, $N_3$, NCS, CN, $NO_2$, $NX_1X_2$, $OX_3$, OAc, O-acyl, O-aroyl, $O(CH_2)_jOX_3O(CH_2)_jNX_1X_2$, NH-acyl, NH-aroyl, CHO, C(halogen)$_3$, $COOX_3$, $SO_3H$, $SO_2NX_1X_2$, $CONX_1X_2$, alkyl, alcohol, alkoxy, alkylmercapto, alkylamino, di-alkylamino, alkylsulfinyl, alkylsulfonyl or methylene dioxy when Z comprises a structure having two adjacent carbon atoms.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

In a variation of formula I R1 and R2 each independently comprise -T-$(CH_2)_n$-$Q_1$-$(CH_2)_m$—Z.

each n independently comprises an integer from 0 to about 7.

m is an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

$Q_1$ comprises NH, O, S, CH=CH, C≡C, CO, $SO_2$ or $OSO_2$.

Z comprises an unsaturated ring having 5 ring atoms and 0 to 2 independently selected heteroatoms as ring members fused to an unsaturated ring having 5 ring atoms and 0 to 2 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members.

In a variation of formula I R1 and R2 each independently comprise -T-$(CH_2)_n$-$Q_1$-$(CH_2)_m$—Z.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

each n independently comprises an integer from 0 to about 7.

m is an integer from 0 to about 7.

$Q_1$ comprises NH, O, S, CH=CH, C≡C, CO, $SO_2$ or $OSO_2$.

Z comprises:

—N◯E   or   —N◯N—E.

E comprises a C1 to about C4, linear or branched alkyl group, a phenyl group, a substituted phenyl group, a benzyl group or a substituted benzyl group.

In a variation of formula I R1 and R2 each independently comprise -T-(CH$_2$)$_n$-Q$_1$-(CH$_2$)$_m$—Z.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

each n independently comprises an integer from 0 to about 7.

m is an integer from 0 to about 7.

Q$_1$ comprises NH, O, S, CH=CH, C≡C, CO, SO$_2$ or OSO$_2$

Z comprises

—N◯O ,   —N(CH$_2$)$_k$ ,   —N((CH$_2$)$_k$)

—◯O(CH$_2$)$_k$   or   —N(A$_1$)(A$_2$)

k is an integer from 1 to about 5. A$_1$ and A$_2$ each independently comprise a C1 to about C4 alkyl group, a phenyl group or a substituted phenyl group.

In a variation of formula I R3 comprises a carbocyclic ring having about 4 to about 7 members, a heterocyclic ring having about 4 to about 7 members, an aromatic ring having about 5 to about 7 ring members, a heteroaromatic ring having about 5 to about 7 members, a bicyclic ring, a heterobicyclic ring, a tricyclic ring, a heterotricyclic ring, a polycyclic ring or a heteropolycyclic ring.

In a variation of formula I R3 comprises

—G◯J L wherein G comprises CH or N, and L and J each independently comprise (CH$_2$)$_n$, O, NH or S. n is an integer from 0 to about 7.

In a variation of formula I R3 comprises

—◯G=J L wherein G, L and J each independently comprise CH or N.

In a variation of formula I R3 comprises

[structures: norbornyl-Y, adamantyl-Y, bicyclic alkyl, pinane, and substituted phenyl with X, Y]

wherein X and Y each independently comprise H, halogen, N$_3$, NCS, phenyl, CN, NO$_2$, NX$_1$X$_2$, OX$_3$, OAc, O-acyl, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, alkyl, alcohol, alkoxy, alkylmercapto, alkylamino, di-alkylamino, alkylsulfinyl or alkylsulfonyl.

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members).

X$_3$ comprises H, alkyl, hydroxyloweralkyl, or alkyl-NX$_1$X$_2$.

j is 0 to about 6.

In a variation of formula I R3 comprises a carbocyclic ring having 4 to 6 ring atoms fused to a heterocyclic ring having from 5 to 7 ring atoms, a carbocyclic ring having 4 to 6 ring atoms fused to a heteroaromatic ring having from 5 to 7 ring atoms, a heterocyclic ring having 6 ring atoms fused to a heterocyclic ring having from 5 to 7 ring atoms, a heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms.

In a variation of formula I R4 comprises H, halogen, N$_3$, NCS, phenyl, CN, NO$_2$, NX$_1$X$_2$, OX$_3$, OAc, O-acyl, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, alkyl, alcohol, alkoxy, alkylmercapto, alkylamino or di-alkylamino, alkylsulfinyl, or alkylsulfonyl.

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members).

X$_3$ comprises H, alkyl, hydroxyloweralkyl, or alkyl-NX$_1$X$_2$.

j is an integer from 0 to about 6.

In a variation of formula I R4 comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring or a heteropolycyclic ring.

In an advantageous variation of formula I R4 comprises

[Chemical structures shown]

In a variation of formula I R4 comprises —(CH$_2$)$_d$—Z.

d is an integer from 1 to about 6.

Z comprises H, halogen, N$_3$, NCS, phenyl, CN, NO$_2$, NX$_1$X$_2$, OX$_3$, OAc, O-acyl, O-aroyl, O(CH$_2$)$_j$OH, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, alkyl, alkoxy, alkylmercapto, alkylamino, di-alkylamino, alkylsulfinyl or alkylsulfonyl.

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members).

X$_3$ comprises H, alkyl, hydroxyloweralkyl, or alkyl-NX$_1$X$_2$.

j is an integer from 0 to about 6.

In a variation of formula I R4 comprises —CH$_2$OH or —CH$_2$Oalkyl.

In a variation of formula I R4 comprises —(CH$_2$)$_d$—Z.

d is an integer from 1 to about 6.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_d$— group and the Z group can be any available ring carbon atom or any available ring nitrogen atom.

In a variation of formula I R4 comprises —(CH$_2$)$_d$—Z.

d is an integer from 1 to about 6.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_d$— group and the Z group can be any available ring carbon atom or any available ring nitrogen atom.

In a variation of formula I R4 comprises —(CH$_2$)$_p$-Q$_1$-(CH$_2$)$_q$—Z.

Q$_1$ comprises NH, O, S, CH=CH, C≡C, CO, SO$_2$ or OSO$_2$.

p is an integer from 1 to about 7.

q is an integer from 0 to about 7.

Z comprises H, halogen, N$_3$, NCS, phenyl, CN, NO$_2$, NX$_1$X$_2$, OX$_3$, OAc, O-acyl, O-aroyl, NH-acyl, NH-aroyl, O(CH$_2$)$_j$OX$_3$, O(CH$_2$)$_j$NX$_1$X$_2$, CHO, C(halogen)$_3$, COOX$_3$, SO$_3$H, SO$_2$NX$_1$X$_2$, CONX$_1$X$_2$, alkyl, alkoxy, alkylmercapto, alkylamino, di-alkylamino, alkylsulfinyl or alkylsulfonyl.

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members.

X$_3$ comprises H, alkyl, hydroxyloweralkyl, or alkyl-NX$_1$X$_2$.

j is an integer from 0 to about 6.

In a variation of formula I R4 comprises —(CH$_2$)$_p$-Q$_1$-(CH$_2$)$_q$—Z.

Q$_1$ comprises NH, O, S, CH=CH, C≡C, CO, SO$_2$ or OSO$_2$.

p is an integer from 1 to about 7.

q is an integer from 0 to about 7.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$), group and the Z group can be any available ring carbon atom or any available ring nitrogen atom.

In a variation of formula I R4 comprises —(CH$_2$)$_p$-Q$_1$-(CH$_2$)$_q$—Z.

Q$_1$ comprises NH, O, S, CH=CH, C≡C, CO, SO$_2$ or OSO$_2$.

p is an integer from 1 to about 7.

q is an integer from 0 to about 7.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —($CH_2$)$_n$— group and the Z group can be any available ring carbon atom or any available ring nitrogen atom.

In a variation of formula I R4 comprises —($CH_2$)$_p$-$Q_1$-($CH_2$)$_q$—Z.

$Q_1$ comprises NH, O, S, CH=CH, C≡C, CO, $SO_2$ or $OSO_2$.

p is an integer from 1 to about 7.

q is an integer from 0 to about 7.

Z comprises

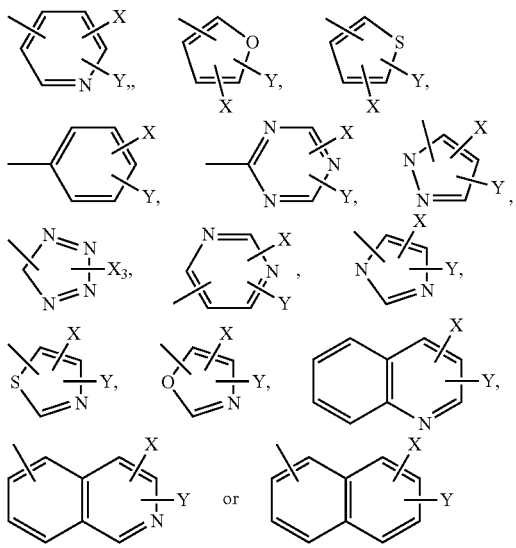

wherein X and Y each independently comprise H, halogen, $N_3$, NCS, CN, $NO_2$, $NX_1X_2$, $OX_3$, OAc, O-acyl, O-aroyl, O($CH_2$)$_j$$OX_3$, O($CH_2$)$_j$$NX_1X_2$, NH-acyl, NH-aroyl, CHO, C(halogen)$_3$, $COOX_3$, $SO_3H$, $SO_2NX_1X_2$, $CONX_1X_2$, alkyl, alcohol, alkoxy, alkylmercapto, alkylamino, di-alkylamino, alkylsulfinyl, alkylsulfonyl or methylene dioxy when Z comprises a structure having two adjacent carbon atoms.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

J is an integer from 0 to about 6.

In any variation of formula I, when A is a direct bond; and B is N(R5); and either of R1 and R2 is phenyl [optionally substituted with one more halogen atoms, ($C_1$-$C_6$) alkyl, ($C_1$-$C_6$) alkoxy, trifluoromethyl, cyano, nitro, ($C_1$-$C_6$) alkyl sulfonyl, ($C_1$-$C_6$) alkyl sulfonyl amino, ($C_1$-$C_6$) alkyl carbonylamino, ($C_1$-$C_6$) alkyl amino-carbonyl-amino or phenyl], ($C_2$-$C_6$) alkyl, cyclohexyl [optionally substituted with ($C_1$-$C_6$) alkyl, ($C_1$-$C_6$) alkoxy, trifluoromethyl, cyano or one or more fluorine atoms], 1-napthyl or 2-napthyl [optionally substituted with one or more halogen atoms, ($C_1$-$C_6$) alkyl, ($C_1$-$C_6$) alkoxy, trifluoromethyl or cyano], benzyl [optionally substituted on the phenyl ring with one or more halogen atoms, ($C_1$-$C_6$) alkyl, ($C_1$-$C_6$) alkoxy, trifluoromethyl or cyano], a 5- to 10-membered saturated or unsaturated heterocyclic radical [optionally substituted with one or more fluorine atoms, ($C_1$-$C_6$) alkyl, ($C_1$-$C_6$) alkoxy, trifluoromethyl or cyano] and a 5- to 10-membered aromatic monocyclic or bicyclic heterocyclic radical [optionally substituted with one more halogen atoms, ($C_1$-$C_6$) alkyl, ($C_1$-$C_6$) alkoxy, trifloromethyl, cyano, nitro or phenyl] and R3 is any above described variation; then R4 can not be H, ($C_1$-$C_6$) alkyl, benzyl, chloro, or bromo.

In any variation of formula I when A is a direct bond; and B is N(R5); and either R1 or R2 is phenyl, thienyl, 2-pyridinyl, 3-pyridinyl, 4-pyridinyl, pyrimidinyl, pyrazinyl, pyridazinyl, triazinyl or any above group substituted with 1, 2, 3 or 4 substituents which can be the same or different, selected from $C_{1-3}$ alkyl, $C_{1-3}$ alkoxy, hydroxy, halogen, trifluoromethyl, trifluoromethylthio, trifluoromethoxy, nitro, amino, mono- or dialkyl($C_{1-2}$)-amino, mono- or dialkyl ($C_{1-2}$)-amido, ($C_{1-3}$)-alkoxycarbonyl, carboxyl, cyano, carbornyl, acetyl and naphthyl; and R3 is any above described variation; then R4 can not be H, halogen, CN, carbornyl, formyl, acetyl, trifluoroacetyl, fluoroacetyl, propionyl, sulfamoyl, methanesulfonyl, methylsulfanyl, branched or unbranched $C_{1-4}$ alkyl group, which $C_{1-4}$ alkyl group may be substituted with 1 to 3 fluoro atoms or with a single bromo, chloro, iodo, cyano or hydroxy group.

Another embodiment of the invention comprises cannabimimetic thiazole and oxazole ligands represented by formula II:

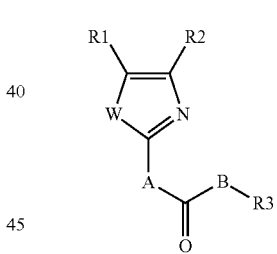

II wherein A, B, R1, R2 and R3 are as defined above for compounds of formula I.

W comprises S or O.

In any variation of formula II, when A is a direct bond; B is NR5 as defined above; R1 and R3 are any above described variation; and W is S; then R2 cannot be a phenyl group with one or more substituents selected from branched or unbranched $C_{1-3}$-alkyl, branched or unbranched $C_{1-3}$-alkoxy, hydroxy, halogen, $CF_3$, trifluoromethylthio, trifluoromethoxy, nitro, amino, mono- or dialkyl($C_{1-2}$)-amino, mono- or dialkyl($C_{1-2}$)-amido, branched or unbranched ($C_{1-3}$)-alkoxycarbonyl, trifluoromethylsulfonyl, sulfamoyl, branched or unbranched ($C_{1-3}$)-sulfonyl, carboxyl, cyano, carbamoyl, branched or unbranched dialkyl($C_{1-3}$)-aminosulfonyl, branched or unbranched monoalkyl($C_{1-3}$)-aminosulfonyl and acetyl. Another embodiment of the invention comprises cannabimimetic triazole ligands represented by formula III:

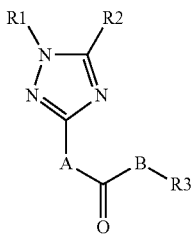

III wherein A, B, R1, R2 and R3 are as defined above for compounds of formula I.

In any variation of formula III, when A is a direct bond; B is NR5; R3 is any above described variation; then either or both of R1 and R2 cannot be a phenyl, naphthyl, thienyl, pyridyl, pyrimidyl, pyrazinyl, pyridazinyl, or triazinyl group, or any above group substituted with 1-4 substituents, which can be same or different, selected from branched or unbranched ($C_{1-3}$)alkyl or alkoxy, hydroxy, halogen, trifluoromethyl, trifluoromethylthio, trifluoromethoxy, nitro, amino, mono- or dialkyl($C_{1-2}$)-amino, mono- or dialkyl ($C_{1-2}$)-amido, ($C_{1-3}$)-alkoxycarbonyl, trifluoromethylsulfonyl, sulfomyl, ($C_{1-3}$)-alkylsulfonyl, carboxyl, cyano, carbornyl, ($C_{1-3}$)-dialkylaminosulfonyl, ($C_{1-3}$)-monoalkylamino-sulfonyl and acetyl.

Another embodiment of the invention comprises cannabimimetic pyrazole ligands represented by formula IV:

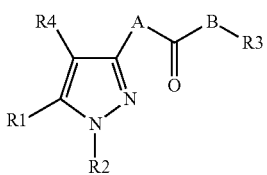

IV wherein A, B, R2, R3 and R4 are as defined above for compounds of formula I.

In a variation of formula IV R1 comprises -T-$(CH_2)_n$-Q-$(CH_2)_n$—Z.

each n independently comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Q is optionally present and if present comprises CH=CH, C≡C.

Z comprises H, halogen, $N_3$, NCS, CN, $NO_2$, $NX_1X_2$, $OX_3$, OAc, O-acyl, O-aroyl, O($CH_2$)$_j$$OX_3$, O($CH_2$)$_j$$NX_1X_2$, NH-acyl, NH-aroyl, NHC(O)—O—$X_3$, CHO, C(halogen)$_3$, COO$X_3$, $SO_3H$, $SO_2NX_1X_2$, CON$X_1X_2$, $SX_1$, Si($X_1$)$_3$, alkoxy, alkylmercapto, alkylamino, di-alkylamino, alkylsulfinyl or alkylsulfonyl.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

each j is independently an integer from 0 to about 6.

In a variation of formula IV R1 comprises -T-$(CH_2)_n$-Q-$(CH_2)_n$—Z.

each n independently comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Q is optionally present and if present comprises CH=CH, C≡C.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula IV R1 comprises -T-$(CH_2)_n$-Q-$(CH_2)_n$—Z.

each n independently comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Q is optionally present and if present comprises CH=CH, C≡C.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula IV R1 comprises -T-$(CH_2)_n$-Q-$(CH_2)_n$—Z.

each n independently comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Q is optionally present and if present comprises CH=CH, C≡C.

Z comprises

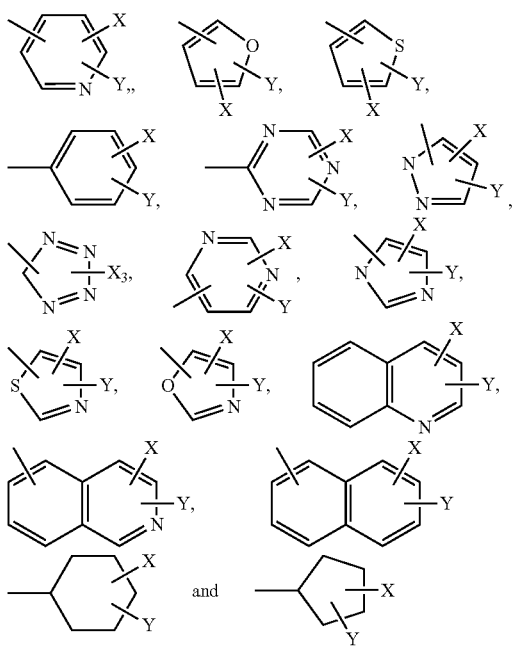

wherein X and Y each independently comprise H, halogen, $N_3$, NCS, CN, $NO_2$, $NX_1X_2$, $OX_3$, OAc, O-acyl, O-aroyl, $O(CH_2)_jOX_3$, $O(CH_2)_jNX_1X_2NH$-acyl, NH-aroyl, CHO, C(halogen)$_3$, $COOX_3$, $SO_3H$, $SO_2NX_1X_2$, $CONX_1X_2$, alkyl, alcohol, alkoxy, alkylmercapto, alkylamino or di-alkylamino, alkylsulfinyl, alkylsulfonyl, or methylene dioxy when Z comprises a structure having two adjacent carbon atoms.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

j is an integer from 0 to about 6.

In a variation of formula IV R1 comprises -T-(CH$_2$)$_n$-Q-(CH$_2$)$_n$—Z.

each n independently comprises an integer from 0 to about 7.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Q is optionally present and if present comprises CH=CH, C≡C.

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members In a variation of formula IV R1 comprises -T-(CH$_2$)$_n$-Q-(CH$_2$)$_n$—Z.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

each n independently comprises an integer from 0 to about 7.

Q is optionally present and if present comprises CH=CH, C≡C.

Z comprises

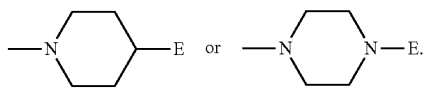

E comprises a C1 to about C4, linear or branched alkyl group, a phenyl group, a substituted phenyl group, a benzyl group or a substituted benzyl group.

In a variation of formula IV R1 comprises -T-(CH$_2$)$_n$-Q-(CH$_2$)$_n$—Z.

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

each n independently comprises an integer from 0 to about 7.

Q is optionally present and if present comprises CH=CH, C≡C.

Z comprises

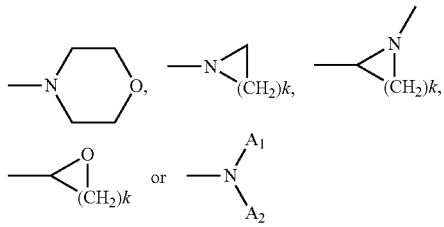

k is an integer from 1 to about 5. $A_1$ and $A_2$ each independently comprise a C1 to about C4 alkyl group, a phenyl group or a substituted phenyl group.

The inventive compounds in any formula, embodiment or variation include any and all possible isomers and steroisomers. In general, the compositions of the invention may be alternately formulated to comprise, consist of, or consist essentially of, any appropriate components herein disclosed. The compositions of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

Unless otherwise specifically defined, "acyl" refers to the general formula —C(O)alkyl.

Unless otherwise specifically defined, "acyloxy" refers to the general formula —O-acyl.

Unless otherwise specifically defined, "alcohol" refers to the general formula alkyl-OH and includes primary, secondary and tertiary variations.

Unless otherwise specifically defined, "alkyl" or "lower alkyl" refers to a linear, branched or cyclic alkyl group having from 1 to about 10 carbon atoms, and advantageously 1 to about 7 carbon atoms including, for example, methyl, ethyl, propyl, butyl, hexyl, octyl, isopropyl, isobutyl, tert-butyl, cyclopropyl, cyclohexyl, cyclooctyl. The alkyl group is saturated. The alkyl group can be unsubstituted, singly substituted or, if possible, multiply substituted, with substituent groups in any possible position. Unless otherwise specifically limited, a cyclic alkyl group includes monocyclic, bicyclic, tricyclic, tetracyclic and polycyclic rings, for example norbornyl, adamantyl and related terpenes.

Unless otherwise specifically defined, "alkoxy" refers to the general formula —O-alkyl.

Unless otherwise specifically defined, "alkylmercapto" refers to the general formula —S-alkyl.

Unless otherwise specifically defined, "alkylamino" refers to the general formula —(NH)-alkyl.

Unless otherwise specifically defined, "di-alkylamino" refers to the general formula —N-(alkyl)$_2$. Unless otherwise specifically limited di-alkylamino includes cyclic amine compounds such as piperidine and morpholine.

Unless otherwise specifically defined, an aromatic ring is an unsaturated ring structure having about 5 to about 7 ring members and including only carbon as ring atoms. The aromatic ring structure can be unsubstituted, singly substituted or, if possible, multiply substituted, with substituent groups in any possible position.

Unless otherwise specifically defined, "aryl" refers to an aromatic ring system that includes only carbon as ring atoms, for example phenyl, biphenyl or naphthyl. The aryl group can be unsubstituted, singly substituted or, if possible, multiply substituted, with substituent groups in any possible position.

Unless otherwise specifically defined, "aroyl" refers to the general formula —C(=O)-aryl.

Unless otherwise specifically defined, a bicyclic ring structure comprises 2 fused or bridged rings that include only carbon as ring atoms. The bicyclic ring structure can be saturated or unsaturated. The bicyclic ring structure can be unsubstituted, singly substituted or, if possible, multiply substituted, with substituent groups in any possible position. The individual rings may or may not be of the same type. Examples of bicyclic ring structures include naphthalene and bicyclooctane.

Unless otherwise specifically defined, a carbocyclic ring is a non-aromatic ring structure, saturated or unsaturated, having about 3 to about 8 ring members that includes only carbon as ring atoms, for example, cyclohexadiene or cyclohexane. The carbocyclic ring can be unsubstituted, singly substituted or, if possible, multiply substituted, with substituent groups in any possible position.

Unless otherwise specifically defined, "halogen" refers to an atom selected from fluorine, chlorine, bromine and iodine.

Unless otherwise specifically defined, a heteroaromatic ring is an unsaturated ring structure having about 5 to about 8 ring members independently selected from carbon atoms and one or more heteroatoms, including oxygen, nitrogen and/or sulfur, for example, pyridine, furan, quinoline, and their derivatives. The heteroaromatic ring can be unsubstituted, singly substituted or, if possible, multiply substituted, with substituent groups in any possible position.

Unless otherwise specifically defined, a heterobicyclic ring structure comprises 2 fused or bridged rings having ring members independently selected from carbon and one or more heteroatoms, including oxygen, nitrogen and/or sulfur. The heterobicyclic ring structure can be saturated or unsaturated. The heterobicyclic ring can be unsubstituted, singly substituted or, if possible, multiply substituted, with substituent groups in any possible position. The individual rings may or may not be of the same type. Examples of heterobicyclic ring structures include isobenzofuran and indole.

Unless otherwise specifically defined, a heterocyclic ring is a saturated or unsaturated ring structure having about 3 to about 8 ring members independently selected from carbon atoms and one or more heteroatoms, including oxygen, nitrogen and/or sulfur; for example, piperidine, morpholine, piperazine, pyrrolidine, thiomorpholine, and their derivatives. The heterocyclic ring can be unsubstituted, singly substituted or, if possible, multiply substituted, with substituent groups in any possible position.

Unless otherwise specifically defined, a heterotricyclic ring structure comprises 3 fused, bridged, or both fused and bridged rings having ring members independently selected from carbon and one or more heteroatoms, including oxygen, nitrogen and/or sulfur. The heterotricyclic ring structure may be saturated or unsaturated. The heterotricyclic ring structure can be unsubstituted, singly substituted or, if possible, multiply substituted, with substituent groups in any possible position. The individual rings may or may not be of the same type. Examples of heterotricyclic ring structures include carbazole, phenanthroline, phenazine, 2,4,10-trioxaadamantane and tetradecahydro-phenanthroline.

Unless otherwise specifically defined, a heteropolycyclic ring structure comprises more than 3 rings that may be fused, bridged or both fused and bridged and that have ring members independently selected from carbon and one or more heteroatoms, including oxygen, nitrogen and/or sulfur. The heteropolycyclic ring structure can be saturated or unsaturated. The heteropolycyclic ring structure can be unsubstituted, singly substituted or, if possible, multiply substituted, with substituent groups in any possible position. The individual rings may or may not be of the same type. Examples of heteropolycyclic ring structures include azaadamantine, tropane, homotropane and 5-norbornene-2,3-dicarboximide.

Unless otherwise specifically defined, the term "phenacyl" refers to the general formula -phenyl-acyl.

Unless otherwise specifically defined, a polycyclic ring structure comprises more than 3 rings that may be fused, bridged or both fused and bridged, and that includes carbon as ring atoms. The polycyclic ring structure can be saturated or unsaturated. The polycyclic ring structure can be unsubstituted, singly substituted or, if possible, multiply substituted, with substituent groups in any possible position. The individual rings may or may not be of the same type. Examples of polycyclic ring structures include adamantine, bicyclooctane, norbornane and bicyclononanes.

Unless otherwise specifically defined, a spirocycle refers to a ring system wherein a single atom is the only common member of two rings. A spirocycle can comprise a saturated carbocyclic ring comprising about 3 to about 8 ring members, a heterocyclic ring comprising about 3 to about 8 ring atoms wherein up to about 3 ring atoms may be N, S, or O or a combination thereof.

Unless otherwise specifically defined, a tricyclic ring structure comprises 3 rings that may be fused, bridged or both fused and bridged, and that includes carbon as ring atoms. The tricyclic ring structure can be saturated or unsaturated. The tricyclic ring structure can be unsubstituted, singly substituted or, if possible, multiply substituted, with substituent groups in any possible position. and may be substituted or unsubstituted. The individual rings may or may not be of the same type. Examples of tricyclic ring structures include fluorene and anthracene.

Unless otherwise specifically limited the term substituted means substituted by a below-described substituent group in any possible position. Substituent groups for the above moieties useful in the invention are those groups that do not significantly diminish the biological activity of the inventive compound. Substituent groups that do not significantly diminish the biological activity of the inventive compound include, for example, H, halogen, $N_3$, NCS, CN, $NO_2$, $NX_1X_2$, $OX_3$, $C(X_3)_3$, OAc, O-acyl, O-aroyl, NH-acyl, NH-aroyl, NHCOalkyl, CHO, C(halogen)$_3$, $COOX_3$, $SO_3H$, $PO_3H_2$, $SO_2NX_1X_2$, $CONX_1X_2$, alkyl, alcohol, alkoxy, alkylmercapto, alkylamino, di-alkylamino, sulfonamide, thioalkoxy or methylene dioxy when the substituted structure has two adjacent carbon atoms, wherein $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members and $X_3$ comprises H, alkyl, hydroxyloweralkyl, or alkyl-$NX_1X_2$. Unless otherwise specifically limited a substituent group may be in any possible position.

Some of the inventive compounds show a high affinity for at least one of the cannabinoid receptors. Thus, another aspect of the invention is use of at least one of the inventive compounds to interact with a cannabinoid receptor.

Some of the novel imidazole derivatives show selectivity for the CB1 cannabinoid receptor. These inventive CB1 selective analogs are able to interact with the CB1 cannabinoid receptor without affecting the peripheral (CB2) receptor to the same degree. Therefore, still another aspect of the invention is use of at least one of the inventive compounds to preferentially interact with a CB1 cannabinoid receptor.

The inventive imidazole analogs described herein, and physiologically acceptable salts thereof, have pharmacological properties when administered in therapeutically effective amounts for providing a physiological response. Thus, another aspect of the invention is the administration of a therapeutically effective amount of at least one of the inventive compounds, or a physiologically acceptable salt thereof, to an individual or animal to provide a physiological response.

A better understanding of the invention will be obtained from the following detailed description of the article and the desired features, properties, characteristics, and the relation of the elements as well as the process steps, one with respect to each of the others, as set forth and exemplified in the description and illustrative embodiments.

DETAILED DESCRIPTION

As used herein a "therapeutically effective amount" of a compound, is the quantity of a compound which, when administered to an individual or animal, results in a sufficiently high level of that compound in the individual or animal to cause a physiological response, for example a discernible increase or decrease in stimulation of cannabinoid receptors. The inventive compounds described herein, and physiologically acceptable salts thereof, have pharmacological properties when administered in therapeutically effective amounts for providing a physiological response useful to treat marijuana abuse, obesity, schizophrenia, epilepsy, stress, memory disorders, migraine, vomiting, thymic disorders, dyskinesia, kinetic disorder, anxiety disorders, psychotic disorders, cognitive disorders, appetite disorders, mood disorders, delirious disorders, neuropathies, Parkinson's disease, Alzheimers disease, depression, psychosomatic-induced disease, as well as for alcohol, opioid, nicotine and cocaine addiction, etc. Additionally, these analogs can be useful in cancer chemotherapy. Typically, a "therapeutically effective amount" of an inventive compound is believed to range from about 10 mg/day to about 1,000 mg/day.

As used herein, an "individual" refers to a human. An "animal" refers to, for example, veterinary animals, such as dogs, cats, horses and the like, and farm animals, such as cows, pigs and the like.

The compound of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

The following examples are given for purposes of illustration only in order that the present invention may be more fully understood. These examples are not intended to limit in any way the scope of the invention unless otherwise specifically indicated.

EXAMPLES

A number of inventive cannabimimetic imidazole and pyrazole derivatives were prepared. Table 1 illustrates some prepared CB1 selective imidazole analogs (compounds 1-1 to 1-41). Table 2 illustrates some prepared CB1 selective pyrazole analogs (compounds 2-1 to 2-3). Tables 3 to 5 illustrate some other disclosed compounds (3-1 to 3-12; 4-1 to 4-7; and 5-1 to 5-21).

TABLE 1
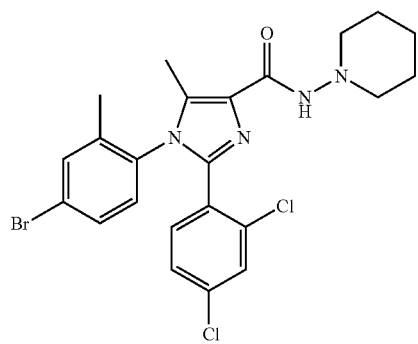 [SMILES: Cc1cc(Br)ccc1-n1c(-c2ccc(Cl)cc2Cl)nc(C(=O)NN2CCCCC2)c1C]
1-1
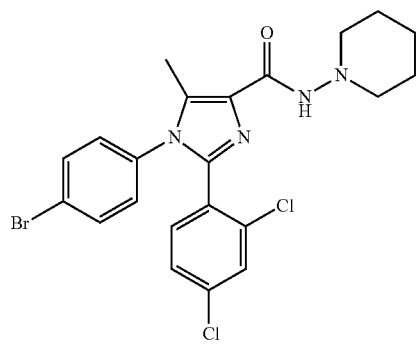 [SMILES: Cc1c(C(=O)NN2CCCCC2)nc(-c2ccc(Cl)cc2Cl)n1-c1ccc(Br)cc1]
1-2
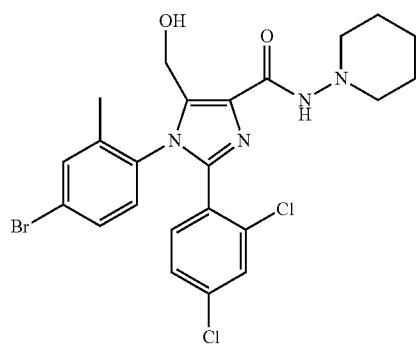 [SMILES: Cc1cc(Br)ccc1-n1c(-c2ccc(Cl)cc2Cl)nc(C(=O)NN2CCCCC2)c1CO]
1-3
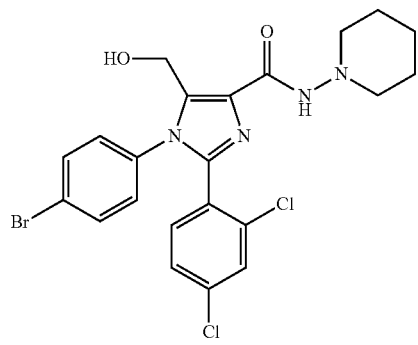 [SMILES: O=C(NN1CCCCC1)c1nc(-c2ccc(Cl)cc2Cl)n(-c2ccc(Br)cc2)c1CO]
1-4
TABLE 1-continued
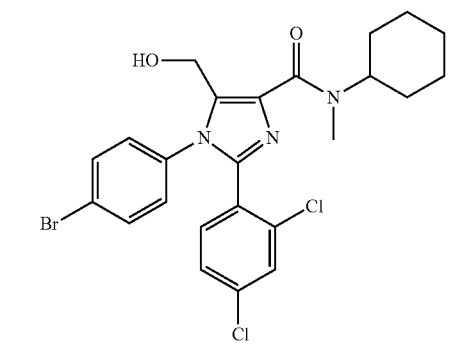 [SMILES: CN(C(=O)c1nc(-c2ccc(Cl)cc2Cl)n(-c2ccc(Br)cc2)c1CO)C1CCCCC1]
1-5
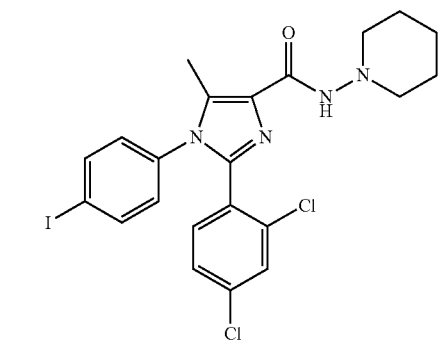 [SMILES: Cc1c(C(=O)NN2CCCCC2)nc(-c2ccc(Cl)cc2Cl)n1-c1ccc(I)cc1]
1-6
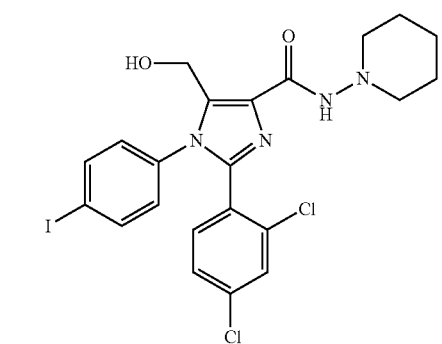 [SMILES: O=C(NN1CCCCC1)c1nc(-c2ccc(Cl)cc2Cl)n(-c2ccc(I)cc2)c1CO]
1-7
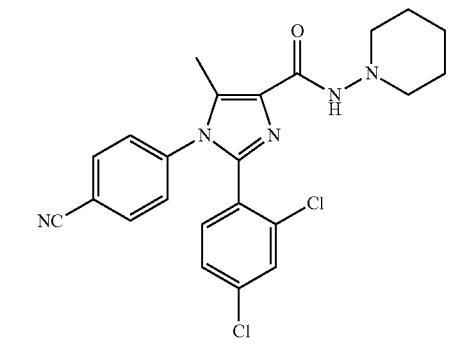 [SMILES: Cc1c(C(=O)NN2CCCCC2)nc(-c2ccc(Cl)cc2Cl)n1-c1ccc(C#N)cc1]
1-8

TABLE 1-continued
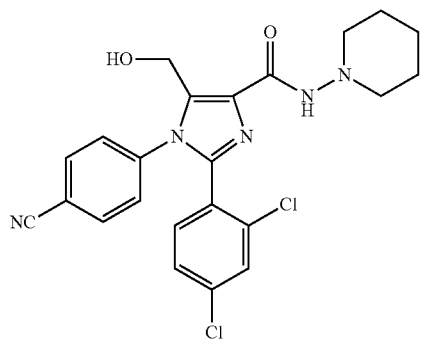 [SMILES: N#Cc1ccc(-n2c(-c3ccc(Cl)cc3Cl)nc(C(=O)NN3CCCCC3)c2CO)cc1]
1-9
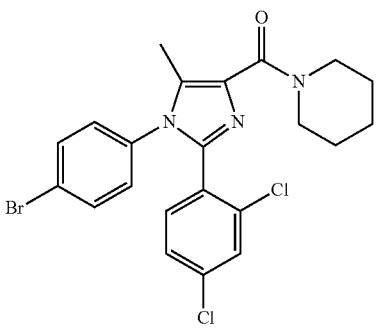
1-13
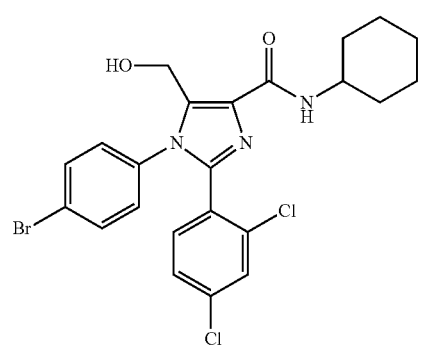 [SMILES: O=C(NC1CCCCC1)c1nc(-c2ccc(Cl)cc2Cl)n(-c2ccc(Br)cc2)c1CO]
1-10
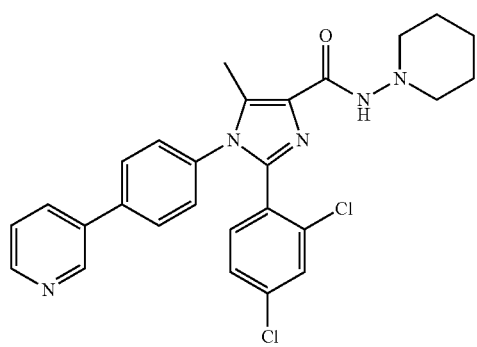
1-14
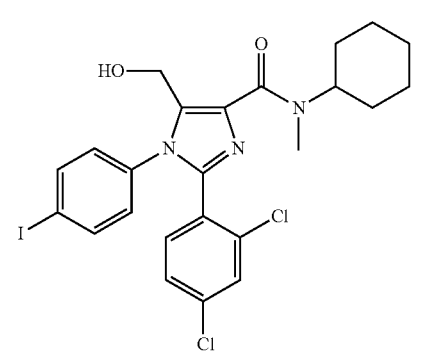 [SMILES: CN(C(=O)c1nc(-c2ccc(Cl)cc2Cl)n(-c2ccc(I)cc2)c1CO)C1CCCCC1]
1-11
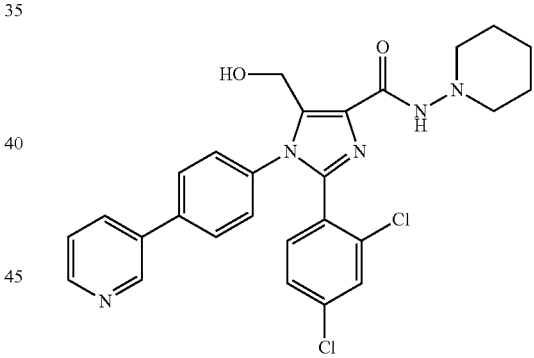
1-15
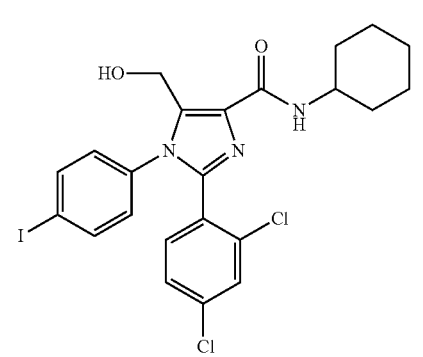
1-12
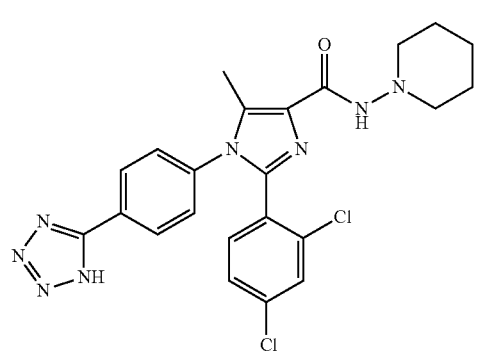
1-16

TABLE 1-continued
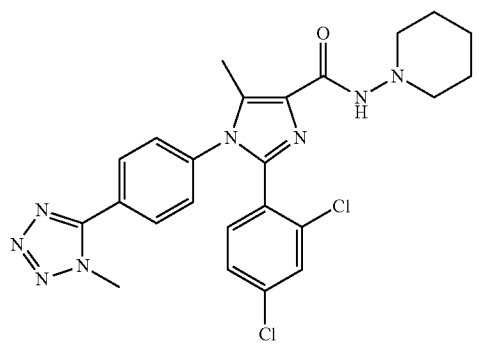
1-17
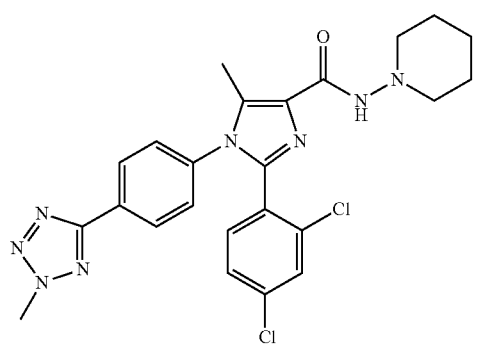
1-18
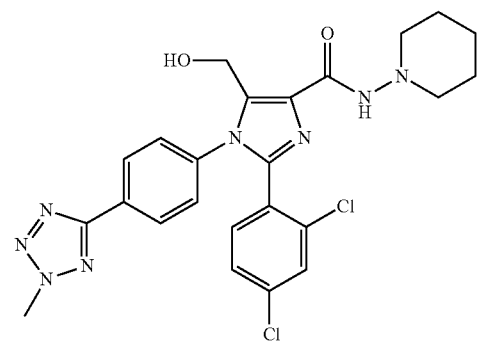
1-19
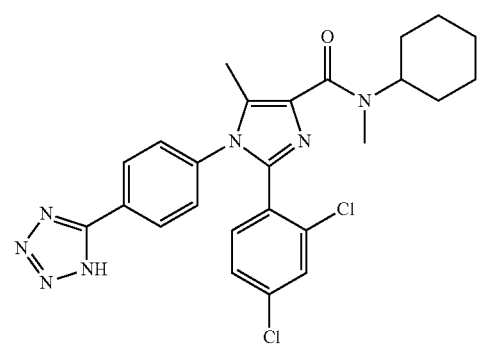
1-20
TABLE 1-continued
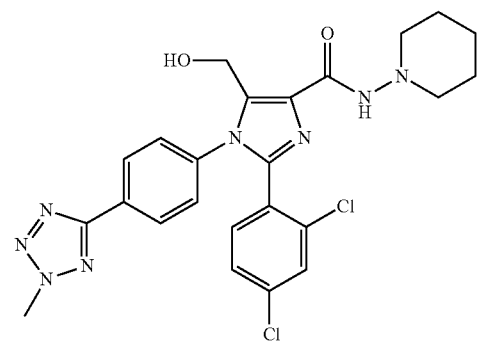
1-21
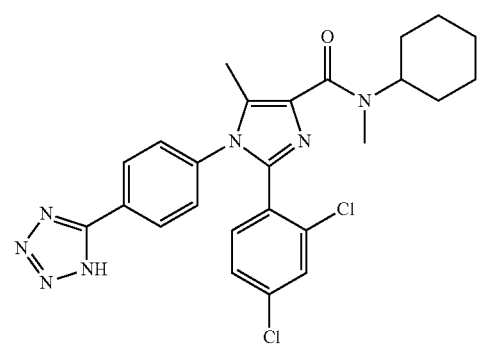
1-22
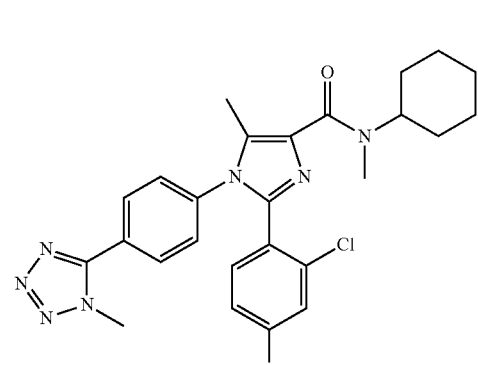
1-23
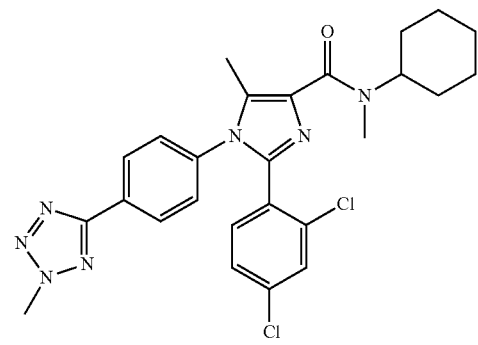
1-24

TABLE 1-continued
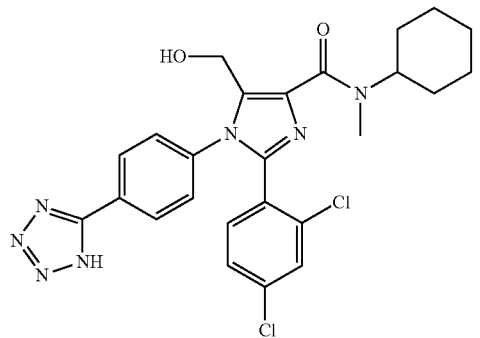 1-25
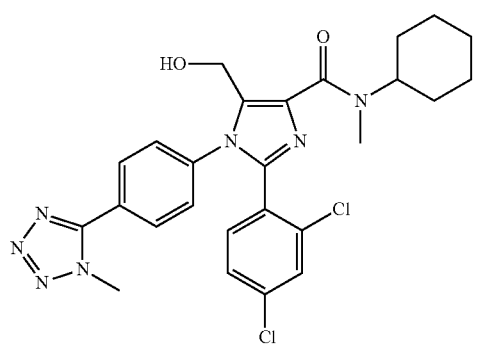 1-26
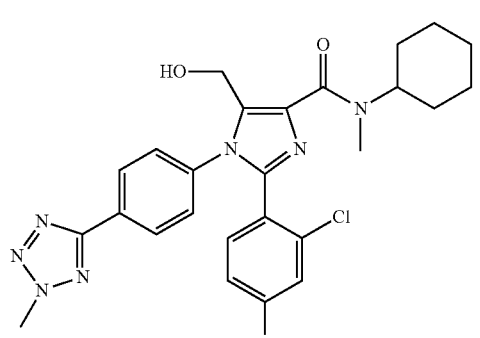 1-27
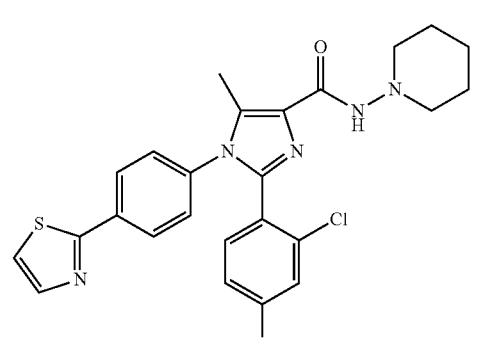 1-28
TABLE 1-continued
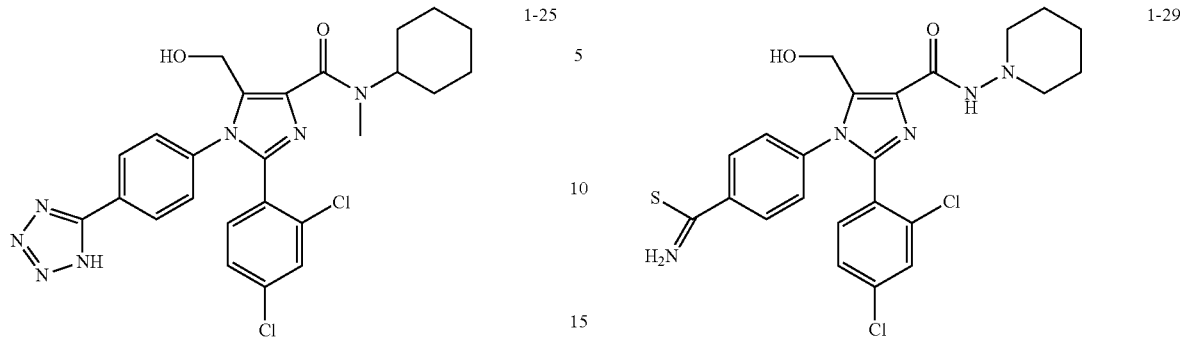 1-29
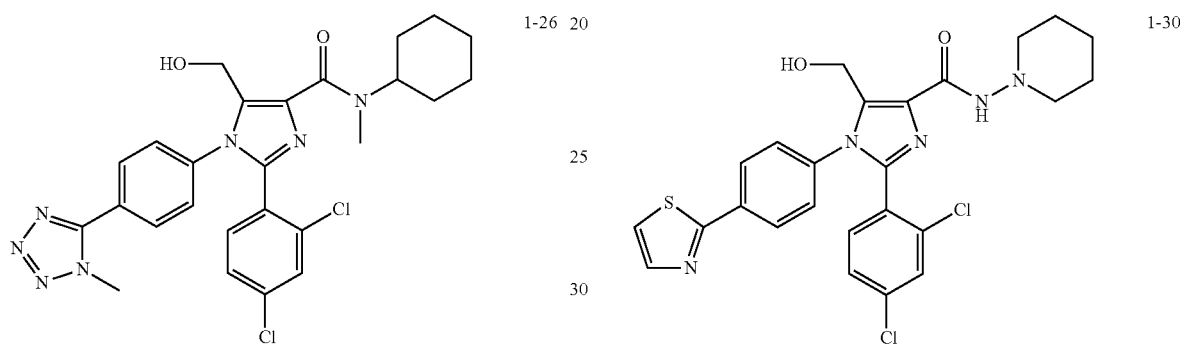 1-30
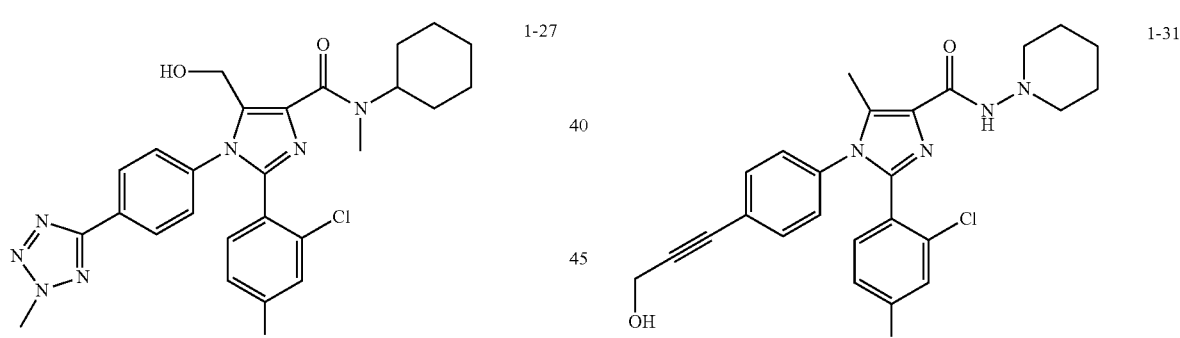 1-31
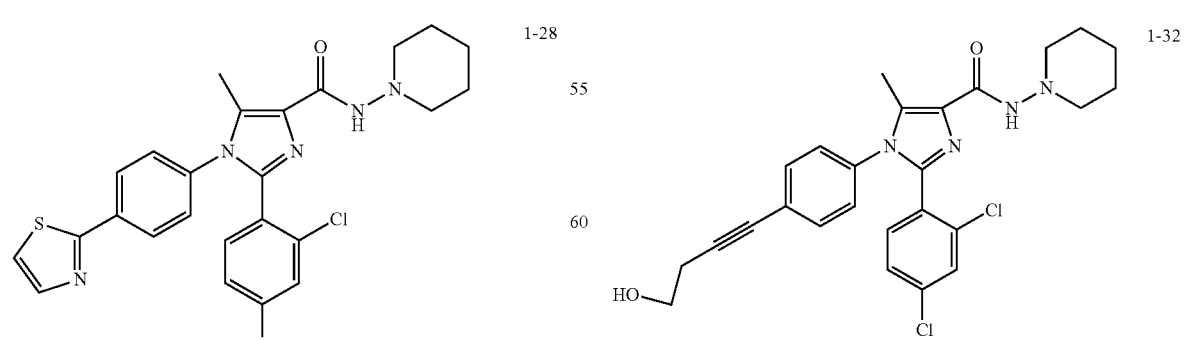 1-32

TABLE 1-continued
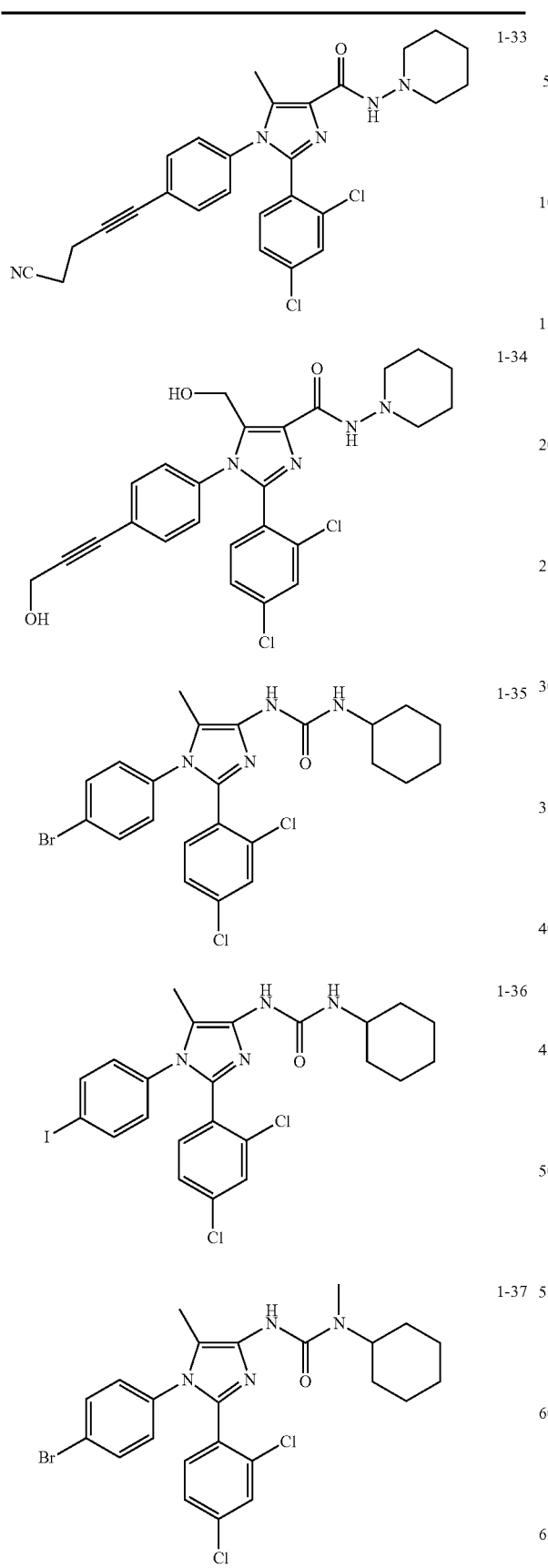
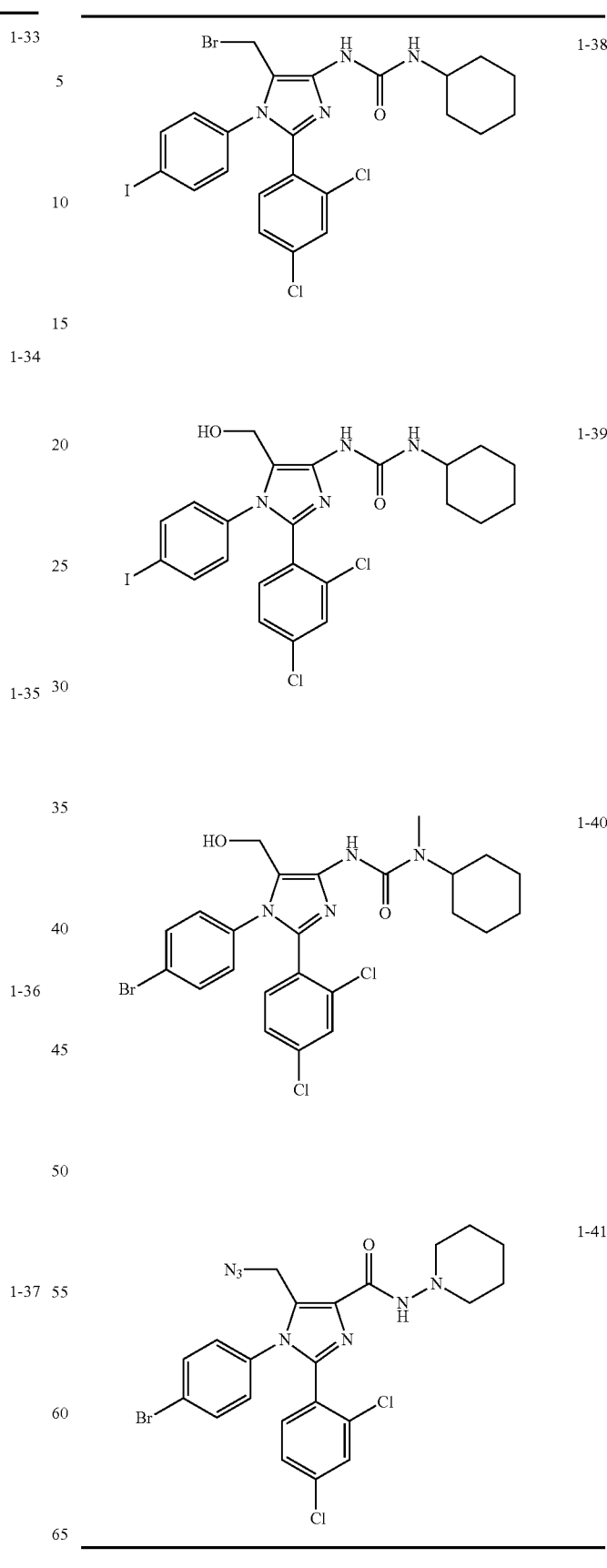

TABLE 2
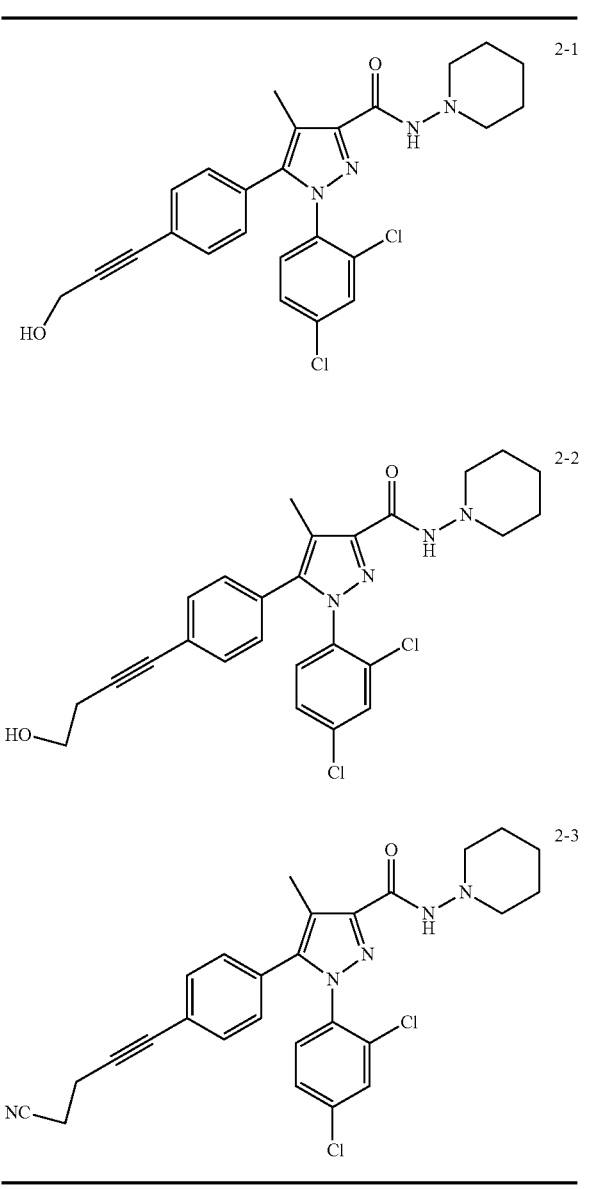
TABLE 3
TABLE 3-continued
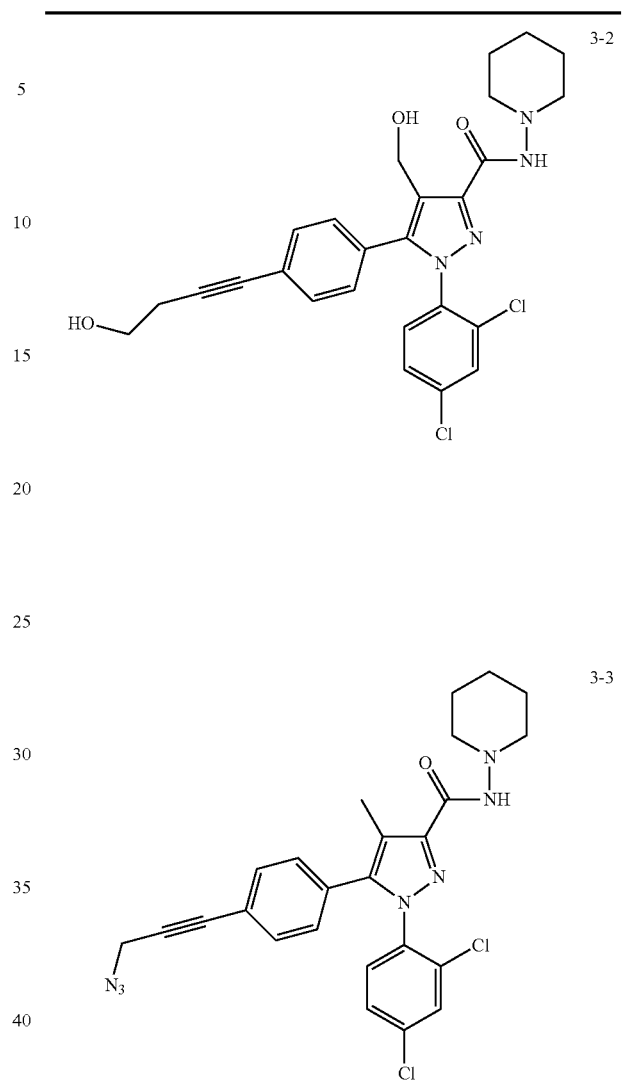
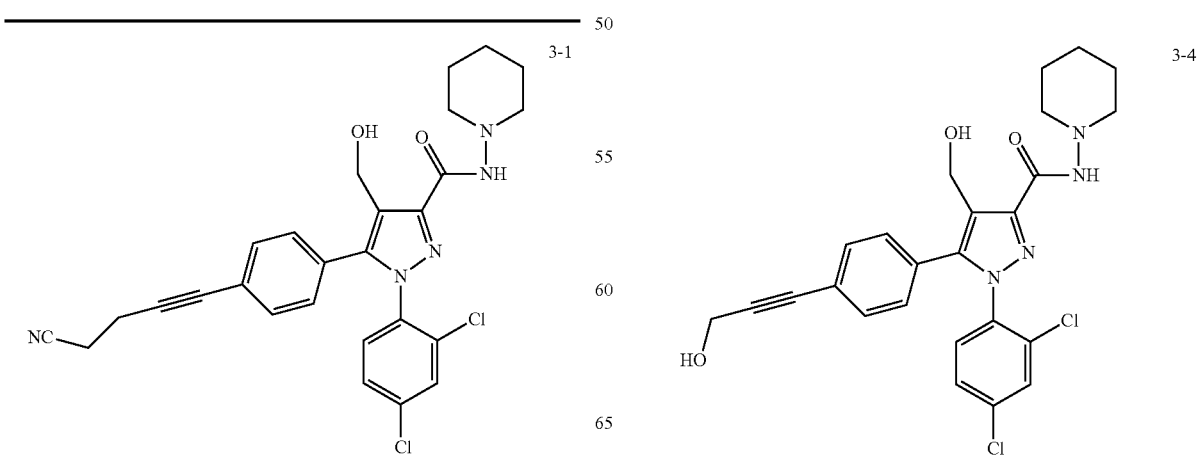

TABLE 3-continued
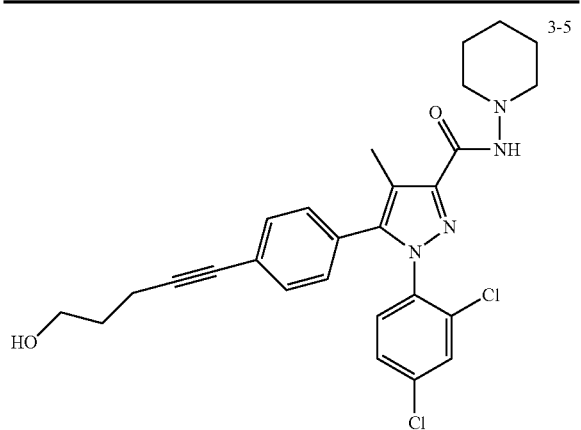
3-5
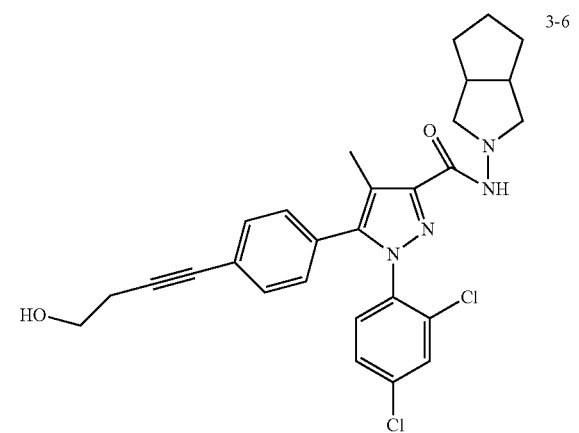
3-6
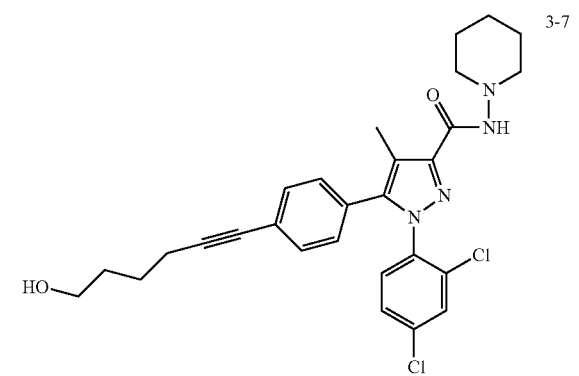
3-7
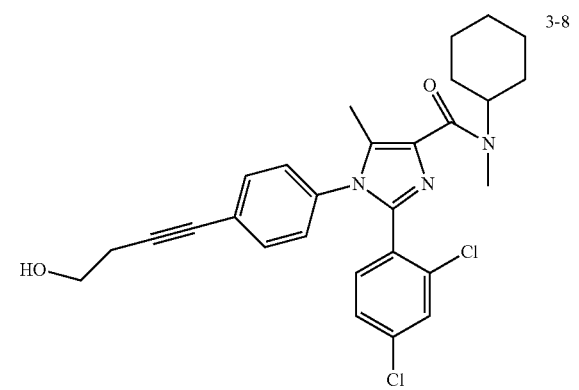
3-8
TABLE 3-continued
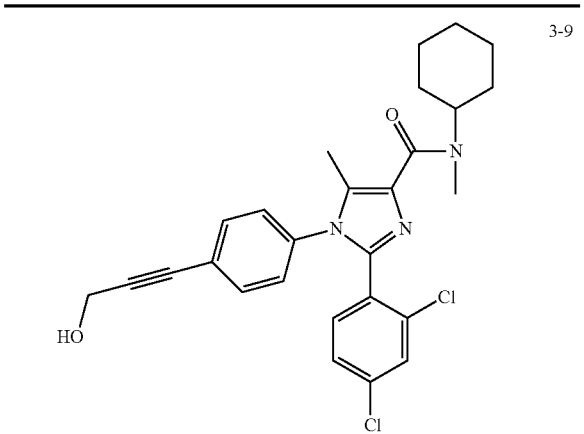
3-9
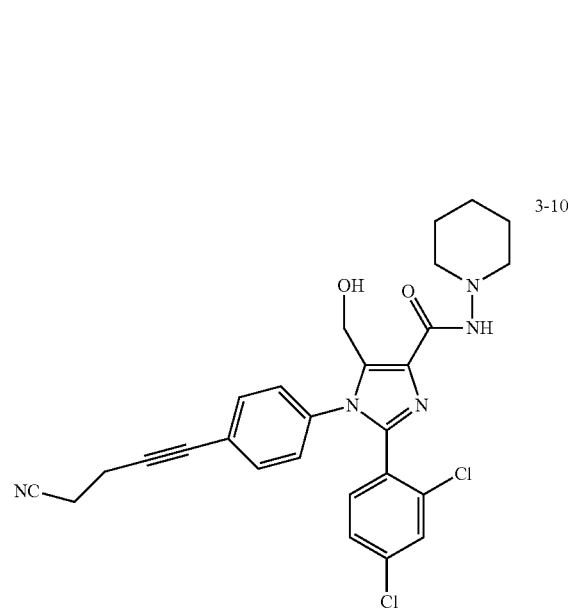
3-10
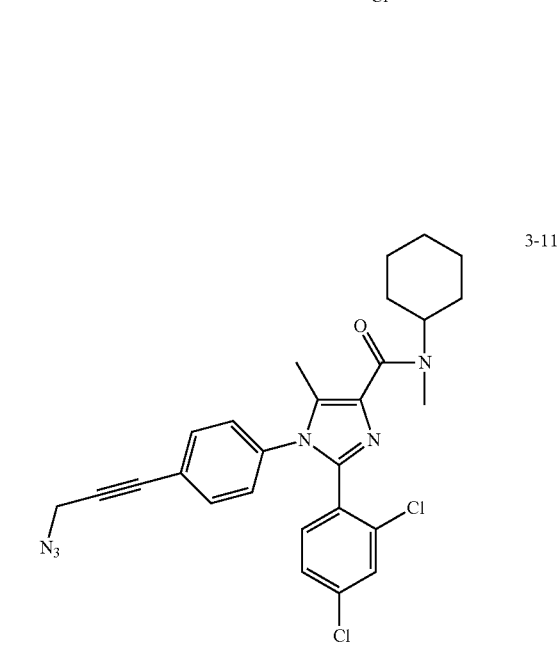
3-11

TABLE 3-continued
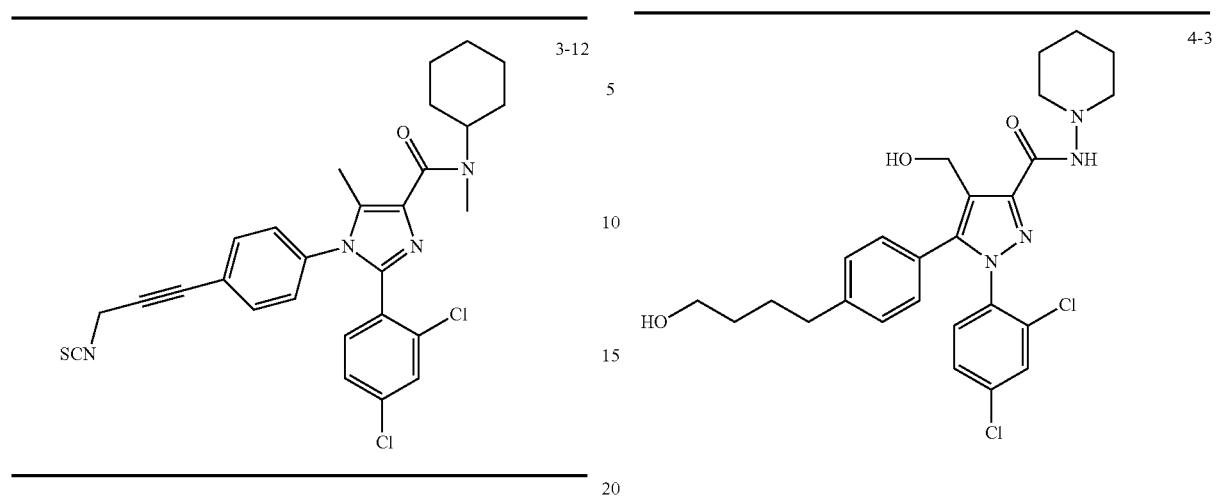
TABLE 4
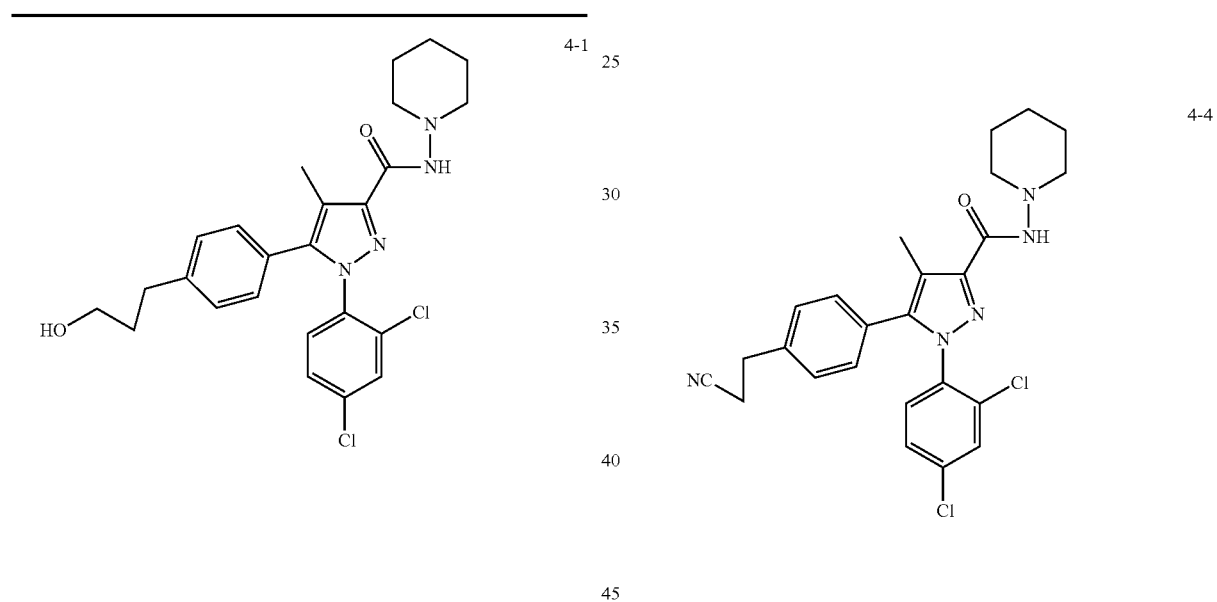
TABLE 4-continued
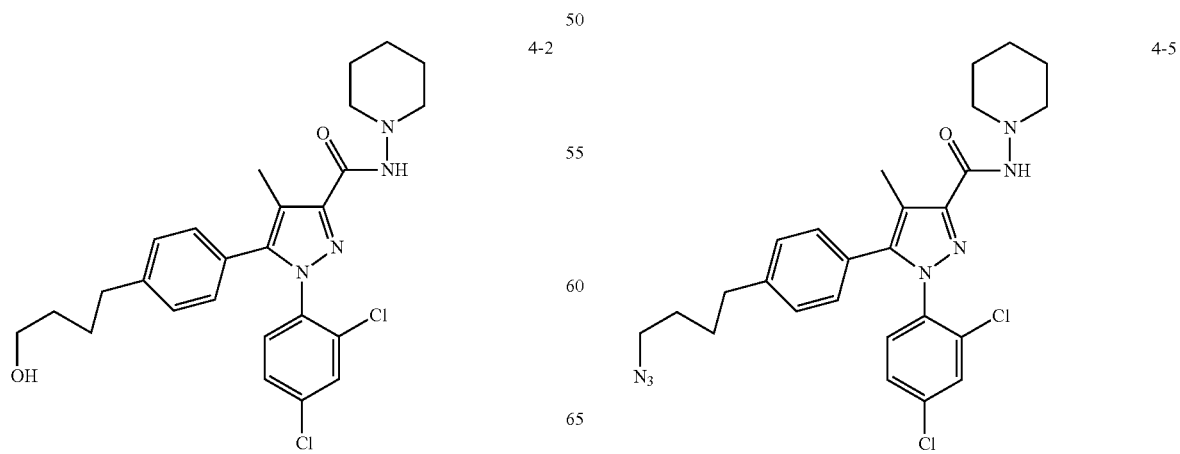

TABLE 4-continued
4-6
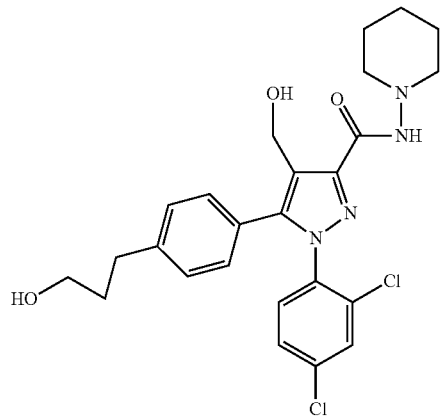
4-7
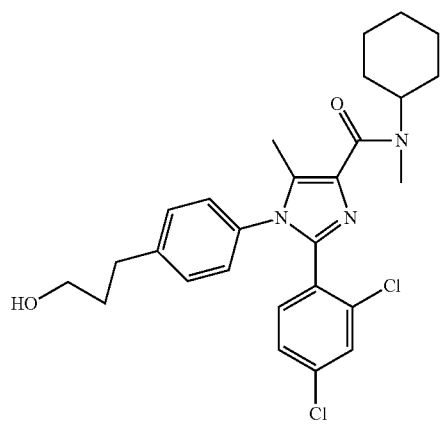
TABLE 5
5-1
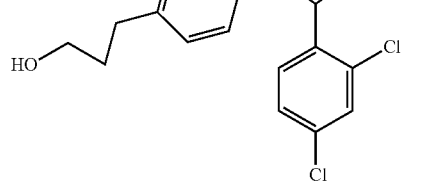
TABLE 5-continued
5-2
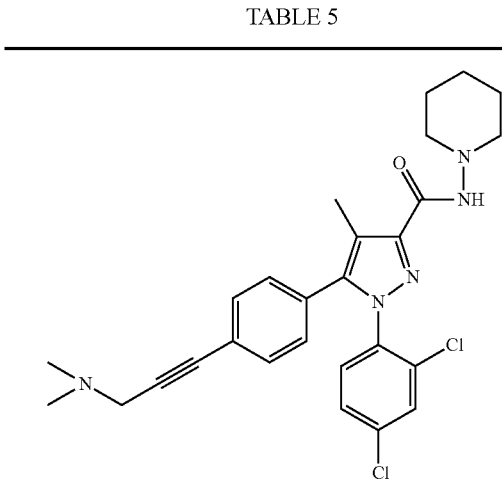
5-3
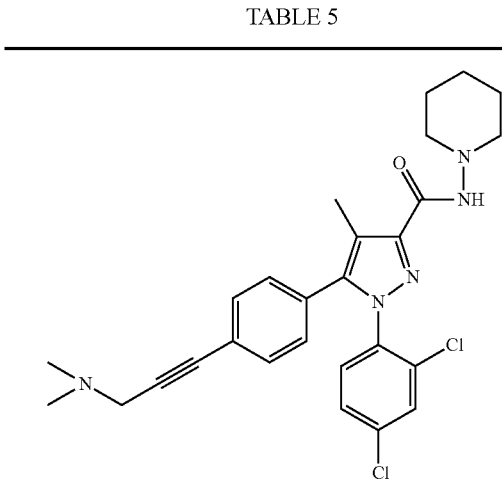
5-4
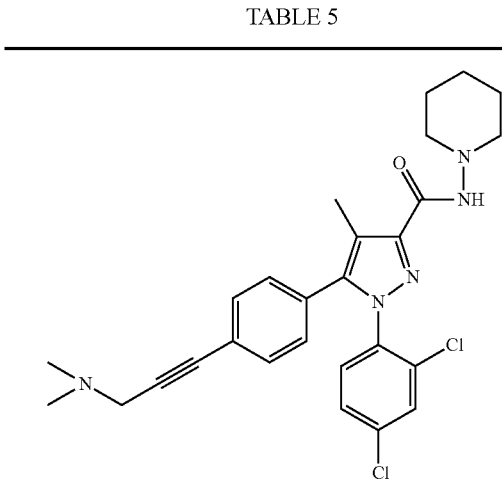
5-5
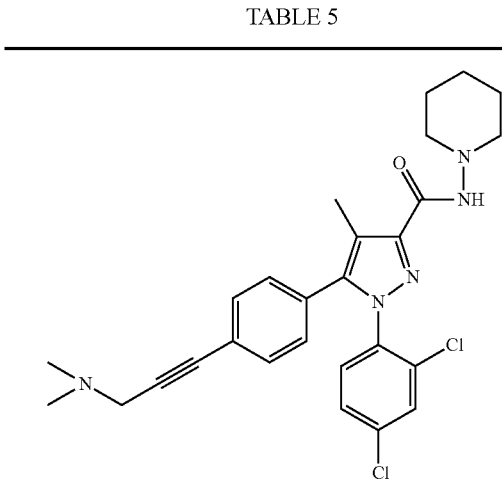

TABLE 5-continued

TABLE 5-continued
5-12
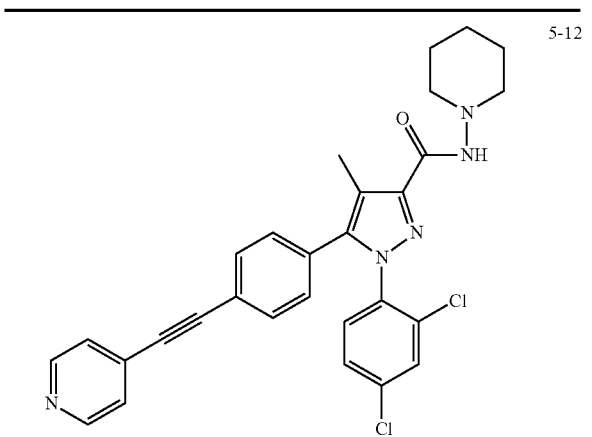
5-13
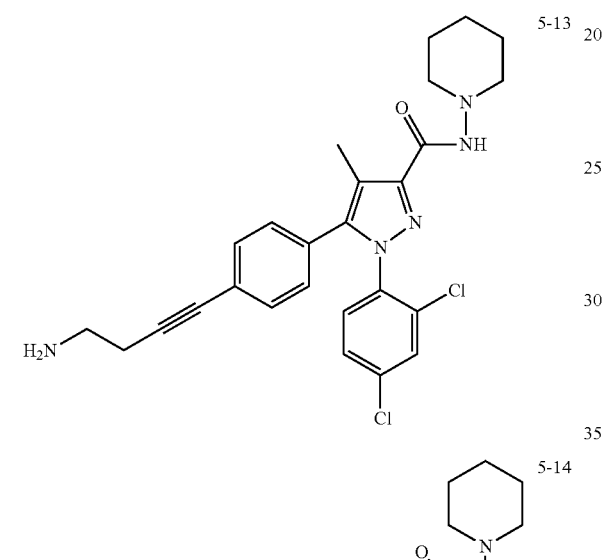
5-14
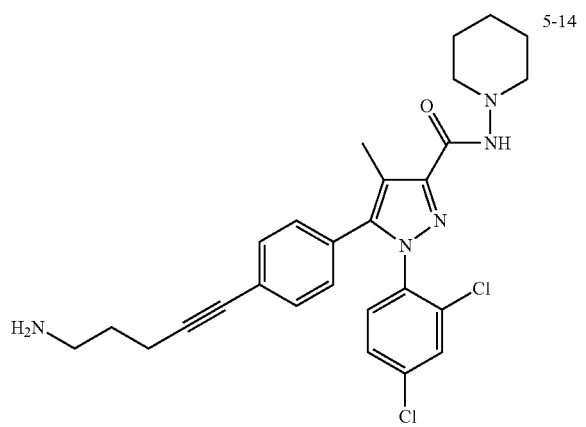
5-15
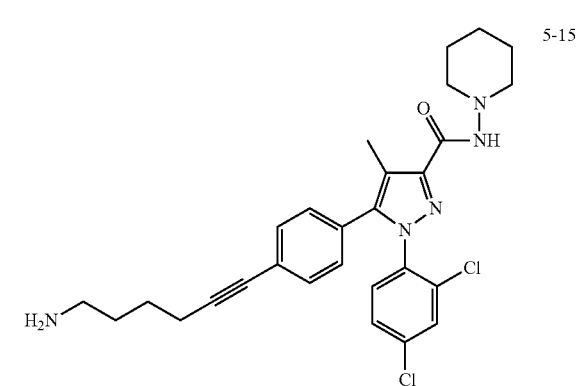
TABLE 5-continued
5-16
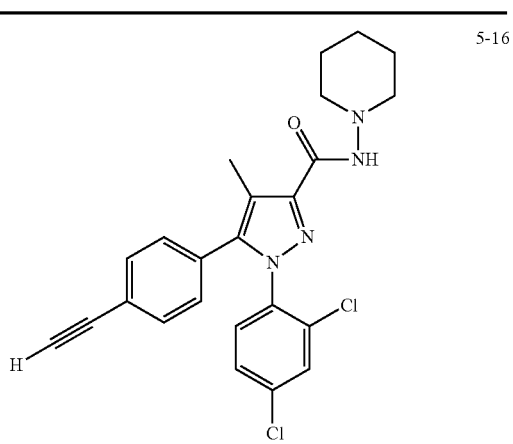
5-17
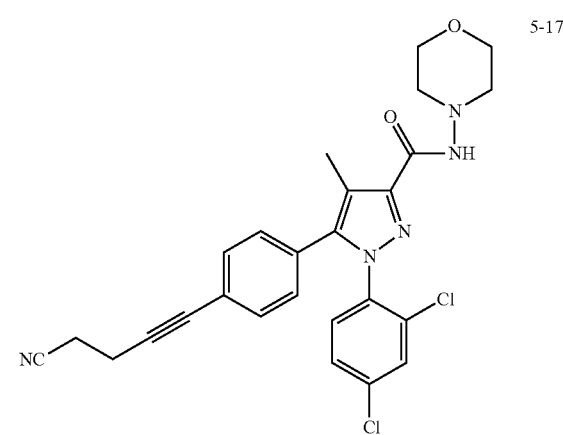
5-18
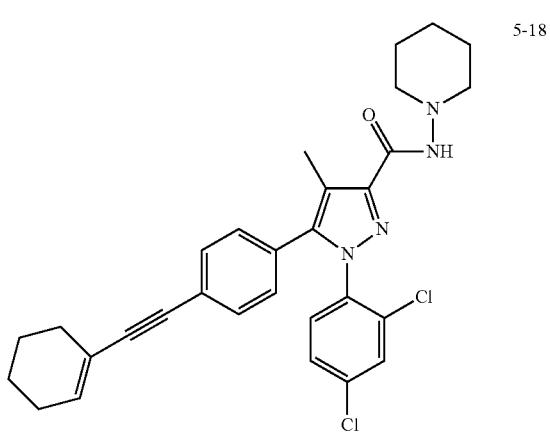

TABLE 5-continued

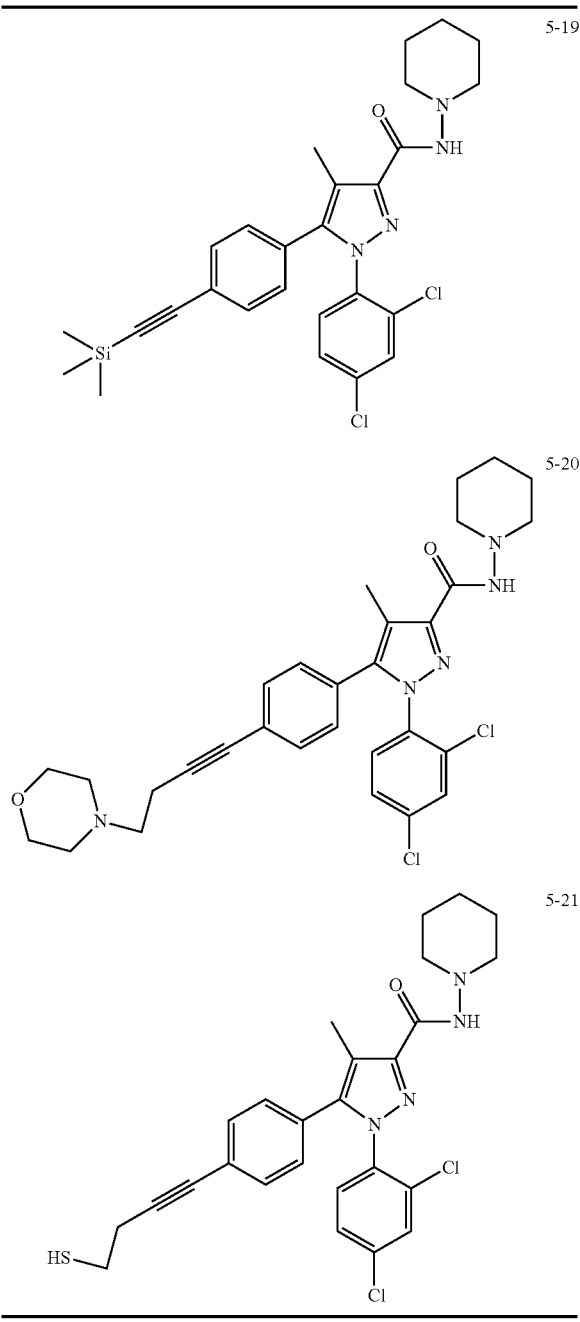

Some of the inventive analogs were tested for CB2 receptor binding affinity and for CB1 receptor affinity (to determine selectivity). As used herein, "binding affinity" is represented by the $K_i$ value which is the inhibition constant correlated with the concentration of an analog required to occupy the 50% of the total number (Bmax) of the receptors. The lower the $K_i$ value the higher the binding affinity. As used herein an analog is said to have "binding selectivity" if it has higher binding affinity for one receptor compared to the other receptor; e.g. a cannabinoid analog which has a K of 0.1 nM for CB1 and 10 nM for CB2, is 100 times more selective for the CB1 receptor.

For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107-118 (1981). The binding of the novel analogues to the CB1 cannabinoid receptor was assessed as described in W. A. Devane et al, *Determination and Characterization of a Cannabinoid Receptor in a Rat Brain*, Mol. Pharmacol., 34, 605-613 (1988) and A. Charalambous et al, 5'-*azido* $\Delta^8$-*THC: A Novel Photoaffinity Label for the Cannabinoid Receptor*, J. Med. Chem., 35, 3076-3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM $MgCl_2$ and 1 mM EDTA) at a pH 7.4. The suspension was incubated at 4° C. for 30 min. At the end of the incubation, the membranes were pelleted and washed three times with TME.

The treated membranes were subsequently used in the binding assay described below. Approximately 30 µg of membranes were incubated in silanized 96-well microtiter plate with TME containing 0.1% essentially fatty acid-free bovine serum albumin (BSA), 0.8 nM [$^3$H] CP-55,940, and various concentrations of test materials in a final volume of 200 µL. The assays were incubated for 1 hour at 30° C. and then immediately filtered using Packard Filtermate 196 harvester and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the assumptions of Cheng et al, *Relationship Between the Inhibition Constant ($K_i$) and the concentration of Inhibitor which causes 50% Inhibition ($IC_{50}$) of an Enzymatic Reaction*, Biochem. Pharmacol., 22, 3099-3102, (1973), which is incorporated by reference herein.

For the CB2 receptor binding studies, membranes were prepared from frozen mouse spleen essentially according to the procedure of P. R. Dodd et al, *A Rapid Method for Preparing Synaptosomes: Comparison with Alternative Procedures*, Brain Res., 226, 107-118 (1981) which is incorporated by reference herein. Silanized centrifuge tubes were used throughout to minimize receptor loss due to adsorption. The CB2 binding assay was conducted in the same manner as for the CB1 binding assay. The binding affinities ($K_i$) were also expressed in nanomoles (nM).

For the compounds of Table 1 the CB1 cannabinoid receptor binding affinities (Ki) for the synthesized analogs range between 1.2 and 5762. The CB2 cannabinoid receptor binding affinities (Ki) for the synthesized analogs range between 75.3 and 26311. The CB1 cannabinoid receptor selectivity for some of the synthesized analogs range from about 2 to about 452. The CB2 cannabinoid receptor selectivity for some of the synthesized analogs range from about 1 to about 4. The cannabinoid receptor binding affinities (Ki) for the synthesized analogs of Table 1 are summarized in Table 6.

TABLE 6

| Compound no. | CB1 Ki | CB2 Ki |
|---|---|---|
| 1-1 | 29.8 | 808.2 |
| 1-2 | 11.5 | 462.1 |
| 1-3 | 54.7 | 803.3 |
| 1-4 | 10.8 | 318.6 |
| 1-5 | 28.8 | 3784 |
| 1-6 | 2.7 | 4309 |
| 1-7 | 1.5 | 1645 |
| 1-8 | 57 | 7222 |
| 1-9 | 51 | 5465 |
| 1-10 | 4.6 | 3032 |
| 1-11 | 6.4 | 1148 |
| 1-12 | 19 | 22433 |
| 1-13 | 22 | 2454 |
| 1-14 | 39.8 | 3329 |
| 1-15 | 23 | 2781 |
| 1-16 | 404 | 10714 |
| 1-17 | 2285 | 24509 |
| 1-18 | 6.5 | 5082 |
| 1-19 | 5762 | 22315 |
| 1-20 | 400 | 12269 |
| 1-21 | 10.5 | 539 |
| 1-22 | 359 | 26311 |
| 1-23 | 982 | 4145 |
| 1-24 | 11.2 | 220 |
| 1-25 | 5214 | 858.2 |
| 1-26 | 101.3 | 1319 |
| 1-27 | 19.0 | 619.8 |
| 1-28 | 7.7 | 656 |
| 1-29 | 47.6 | 640.3 |
| 1-30 | 23.9 | 1508 |
| 1-31 | 18 | 1138 |
| 1-32 | 6.2 | 5092 |
| 1-33 | 1.6 | 270.5 |
| 1-34 | 23.2 | 5364 |
| 1-35 | 6.9 | 20537 |
| 1-36 | 1.2 | 7236 |
| 1-37 | 14.2 | 1423 |
| 1-38 | 5 | 75.3 |
| 1-39 | 6.8 | 1336 |
| 1-40 | 10 | 1015 |
| 1-41 | 7 | 954.3 |

For the compounds of Table 2 the CB1 cannabinoid receptor binding affinities (Ki) for the synthesized analogs range between 0.35 and 33.1. The CB2 cannabinoid receptor binding affinities (Ki) for the synthesized analogs range between 127 and 1490. The CB1 cannabinoid receptor selectivity for some of the synthesized analogs range from about 22 to about 480. The cannabinoid receptor binding affinities (Ki) for the synthesized analogs of Table 2 are summarized in Table 7.

TABLE 7

| Compound no. | CB1 Ki | CB2 Ki |
|---|---|---|
| 2-1 | 33.1 | 1490 |
| 2-2 | 19.7 | 440.5 |
| 2-3 | 0.35 | 127 |

For the compounds of Table 3 the CB1 cannabinoid receptor binding affinities (Ki) for the synthesized analogs range between 1 and 27. The CB2 cannabinoid receptor binding affinities (Ki) for the synthesized analogs range between 78 and 750. The CB1 cannabinoid receptor selectivity for some of the synthesized analogs range from about 6 to about 250. The cannabinoid receptor binding affinities (Ki) for the synthesized analogs of Table 5 are summarized in Table 8.

TABLE 8

| Compound | Receptor Affinities Ki (nM) | | Selectivity | |
|---|---|---|---|---|
|  | CB1 | CB2 | CB1 | CB2 |
| 3-1 | 6 | 265 | 44 |  |
| 3-2 | 16 | 165 | 10 |  |
| 3-3 | 3 | 750 | 250 |  |
| 3-4 | 21 | 313 | 15 |  |
| 3-5 | 2 | 144 | 72 |  |
| 3-6 | 7 | 199 | 28 |  |
| 3-7 | 3 | 116 | 39 |  |
| 3-8 | 12 | 440 | 36 |  |
| 3-9 | 27 | 257 | 9 |  |
| 3-10 | 2 | 279 | 140 |  |
| 3-11 | 1 | 82 | 82 |  |
| 3-12 | 13 | 78 | 6 |  |

For the compounds of Table 4 the CB1 cannabinoid receptor binding affinities (Ki) for the synthesized analogs range between 2 and 100. The CB2 cannabinoid receptor binding affinities (Ki) for the synthesized analogs range between 43 and 7,538. The CB1 cannabinoid receptor selectivity for some of the synthesized analogs range from about 3 to about 250. The cannabinoid receptor binding affinities (Ki) for the synthesized analogs of Table 5 are summarized in Table 9.

TABLE 9

| Compound | Receptor Affinities Ki (nM) | | Selectivity | |
|---|---|---|---|---|
|  | CB1 | CB2 | CB1 | CB2 |
| 4-1 | 26 | 230 | 8 |  |
| 4-2 | 2 | 43 | 21 |  |
| 4-3 | 31 | 7538 | 243 |  |
| 4-4 | 13 | 2294 | 176 |  |
| 4-5 | 3 | 177 | 59 |  |
| 4-6 | 21 | 66 | 3 |  |
| 4-7 | 100 | 290 | 3 |  |

For the compounds of Table 5 the CB1 cannabinoid receptor binding affinities (Ki) for the synthesized analogs range between 8 and 87. The CB2 cannabinoid receptor binding affinities (Ki) for the synthesized analogs range between 13 and 1,527. The CB1 cannabinoid receptor selectivity for some of the synthesized analogs range from about 1 to about 50. The cannabinoid receptor binding affinities (Ki) for the synthesized analogs of Table 5 are summarized in Table 10.

TABLE 10

| Compound | Receptor Affinities Ki (nM) | | Selectivity | |
|---|---|---|---|---|
|  | CB1 | CB2 | CB1 | CB2 |
| 5-1 | 51 | 76 | 1.5 |  |
| 5-2 | 68 | 88 | 1.3 |  |
| 5-3 | 30 | 66 | 2.2 |  |
| 5-4 | 21 | 40 | 2 |  |
| 5-5 | 30 | 30 | 1 |  |
| 5-6 | 12 | 20 | 1.5 |  |
| 5-7 | 20 | 68 | 3.5 |  |
| 5-8 | 9 | 13 | 1.5 |  |
| 5-9 | 50 | 59 | 1 |  |
| 5-10 | 15 | 54 | 3.6 |  |
| 5-11 | 25 | 25 | 1 |  |
| 5-12 | 8 | 421 | 52 |  |
| 5-13 | 20 | 732 | 36 |  |
| 5-14 | 46 | 947 | 20 |  |
| 5-15 | 87 | 1527 | 17 |  |

Preparation of Compounds

General. Column chromatography was carried out by using Horizon, HPFC system available from Biotage, Inc., Charlottesville, Va. Eluents were distilled before use. Solvents for reactions were dried or purified as required. Reactions were carried out under argon atmosphere unless otherwise noted. All of the reagents are available from Sigma-Aldrich Fine Chemicals of Milwaukee, Wis. and/or Lancaster Synthesis Inc. of Windham, N.H.

Modification of the direct aromatic substitution at Imidazole position 1 can be obtained by varying the respective starting aniline (i.e. 4-Bromoaniline).

Modification at imidazole position 2 can be obtained by varying the respective starting material (2,4-dichlorobenznitrile).

Method A: Modification at Imidazole Positions 1, 2 and 4

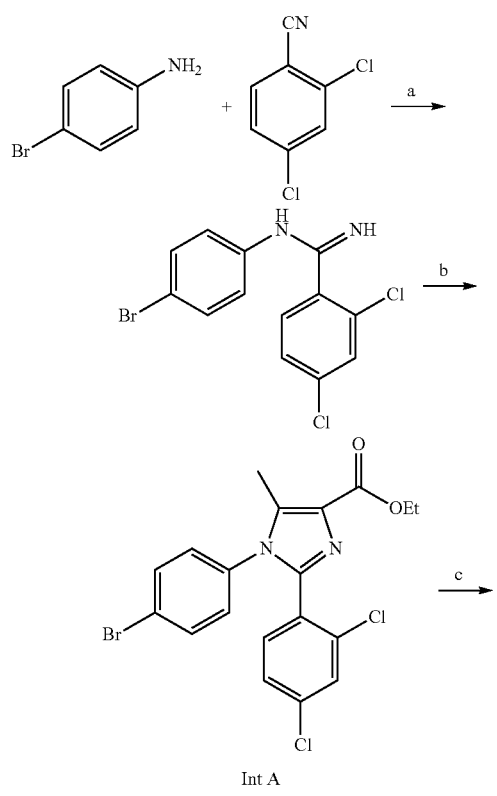

Int A

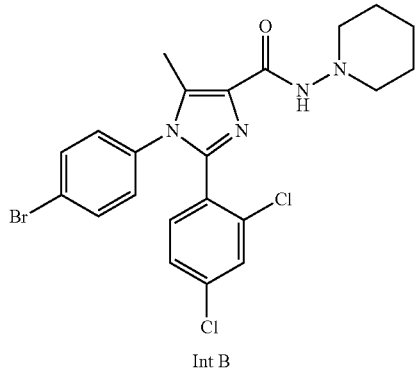

Int B (a) EtMgBr, THF; (b) Ethyl-3-bromo-2-oxo butanoate, Na$_2$CO$_3$, toluene;
(c) 1-aminopiperdine, AlCl$_3$, 1,2-dichloroethane 2,4-dichloro-N-(4-bromophenyl)benzenecarboxylmidamide To a magnetically stirred solution of EtMgBr (3.3 mL, 3M in diethyl ether, 10 mmol) in THF (30 mL) was slowly added 4-bromoaniline portion wise. After the solution was stirred for 30 min., 2,4-dichlorobenzonitrile (1.72 g, 10 mmol) was added. The resulting solution was stirred at room temperature (RT) overnight. The reaction mixture was quenched with water and extracted with ethyl acetate. The combined extracts were dried over anhydrous MgSO$_4$, filtered and evaporated under reduced pressure.

Ethyl 1-(4-bromophenyl)-2-(2,4-dichlorophenyl)-5-methyl-1H-imidazole-4-carboxylate (Int A)

To a magnetically stirred solution of above imidamide (2.45 g, 7 mmol) in 30 mL anhydrous toluene were added ethyl 3-bromo-2-oxobutanoate (1.48 g, 7 mmol) and Na$_2$CO$_3$ (0.74 g, 7 mmol). The contents were stirred at 100° C. for 12 hours (h). The reaction was brought to RT. The reaction mixture was quenched with water and extracted with ethyl acetate. The combined extracts were dried over anhydrous MgSO$_4$, filtered and evaporated under reduced pressure. Purification by column chromatography gave the Int A.

1-(4-bromophenyl)-2-(2,4-dichlorophenyl)-5-methyl-N-(1-piperidinyl)-1H-imidazole-4-carboxylate (Int B)

To the suspension of AlCl$_3$ (1.0 g, 8 mmol) in dichloroethane (20 mL) was added 1-aminopiperidine (1.2 mL, 12 mmol) at 0° C. and stirred for 25 min at that temperature. To this was added a solution of Int A (1.81 g, 4 mmol) in dichloroethane (5 mL). The reaction was brought to RT and stirred at that temperature for 8 h. The reaction was quenched with dil. HCl and the organic layer was extracted with dichloromethane. The combined extracts were dried over anhydrous MgSO$_4$, filtered and evaporated under reduced pressure. Purification by column chromatography gave the Int B.

Method B: Modification at Imidazole Position 1

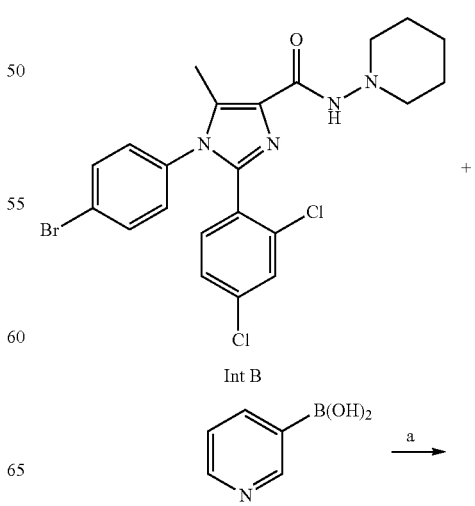

Int B

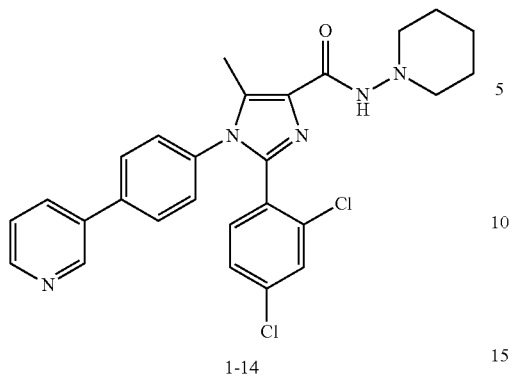

1-14

(a) Pd(PPh₃)₄, Ba(OH)₂•8H₂O, DME

To the suspension of Pd (PPh₃)₄ (0.046 g, 0.04 mmol) in anhydrous DME (10 mL) was added Int B (0.2 g, 0.4 mmol). The mixture was stirred at RT for 30 min. To this solution were added sequentially the pyridine-3-boronic acid (0.058 g, 0.48 mmol), Ba(OH)₂.8H₂O (0.189 g, 0.6 mmol) and 0.3 mL of water and the mixture was refluxed for 18 h., and subjected to filtration. The filtrate was evaporated to dryness. The crude reaction mixture was subjected to column chromatography to yield the biaryl product 1-14.

Method C: Modification at Imidazole Position 1

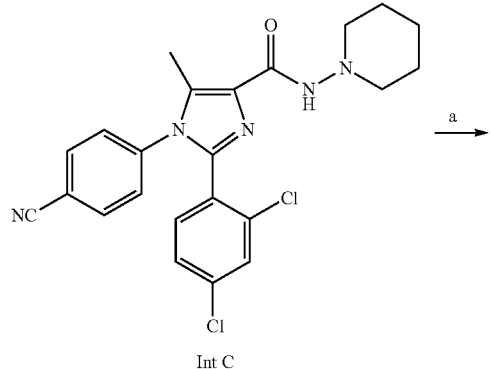

Int C

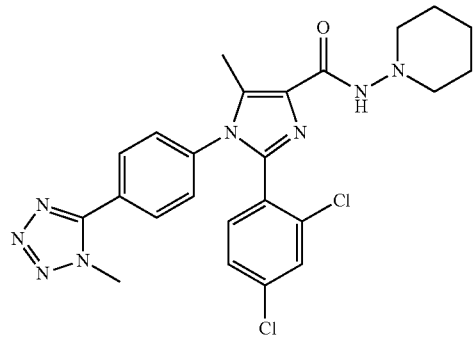

1-17

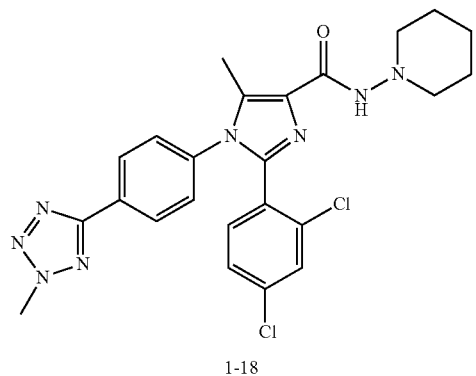

1-18

(a) NaN₃, Et₃N•HCl, toulene; (b) CH₃I, K₂CO₃, CH₃CN

Int. D. The mixture of Int I (1.44 g, 3.19 mmol), NaN₃ (0.65 g, 10 mmol) and Et₃N.HCl (1.37 g, 10 mmol) in toluene (25 mL) was heated to 70° C. for 12 h with stirring. After cooling, the product was extracted with water. The aqueous layer, 36% HCl was added dropwise to salt out the title product. After filtration, the solid was dried under reduced pressure.

Compounds 1-17 and 1-18. To the Int D (0.49 g, 1 mmol) in CH₃CN (10 mL) K₂CO₃ (0.13 g, 1 mmol) was added. To this CH₃I (0.12 ml, 2 mmol) was added. The contents were stirred at room temperature for 4-5 hrs. The reaction was quenched with water and extracted with ethyl acetate. The organic layer was separated and dried over anhydrous MgSO₄. The solvent was removed under reduced pressure. Two isomers 1-17 and 1-18 were separated and purified by column chromatography.

Method D: Modification at Imidazole Position 1

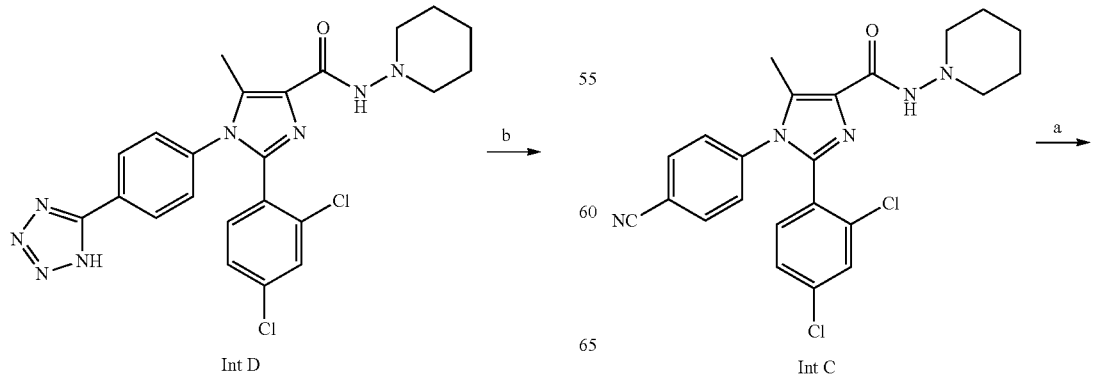

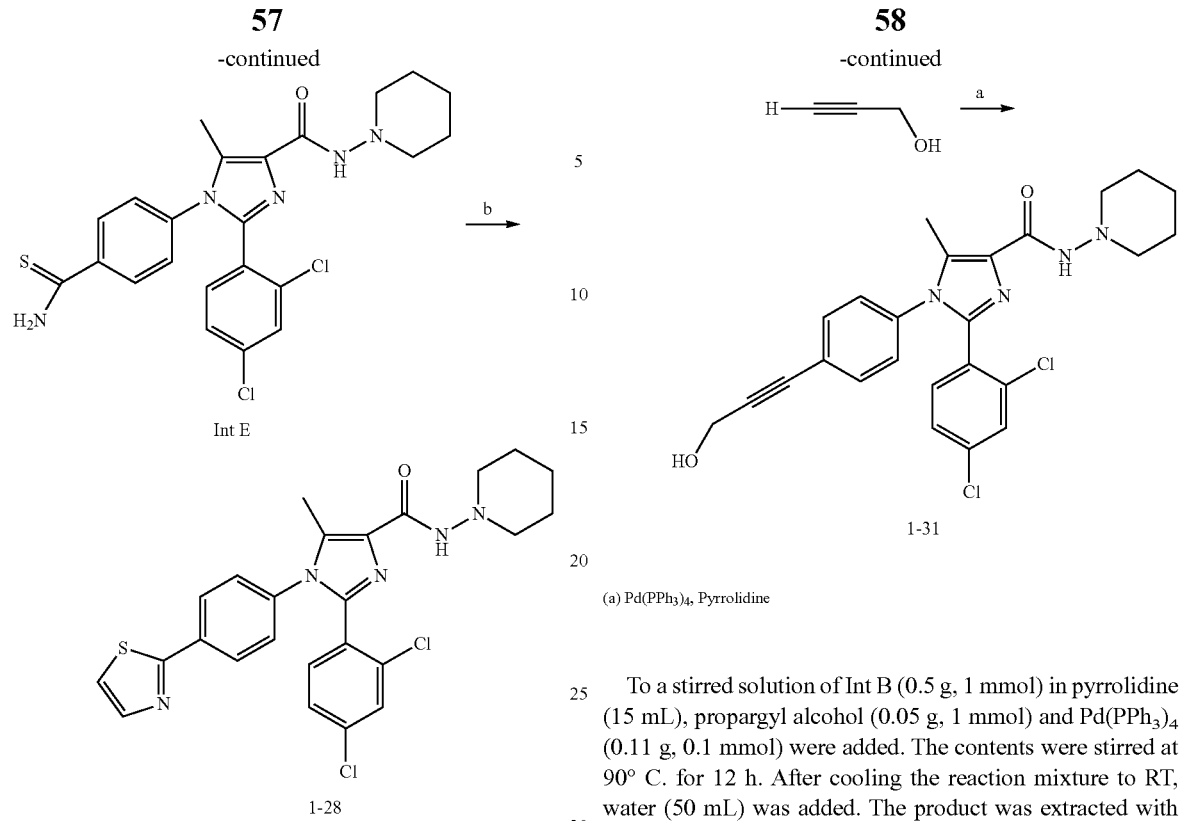

Int E 1-28

(a) Diethyl dithiophosphate, dioxane/water (b) Bromoacetaldehyde diethylacetal, DMF Int E: To the Int C (0.45 g, 1 mmol) in dioxane:water (6:4) (20 mL) diethyl dithiophosphate was added. The contents were stirred at 100° C. for 12 h. The reaction was brought to RT and the organic layer was extracted with diethyl ether. The ether layer was washed with NaHCO₃ and dried over anhydrous MgSO₄. The solvent was removed to yield the titled product. See Tetrahedron, 1989, 45, 4599, the contents of which are herein incorporated by reference.

Compound 1-28: To the above Int E (0.24 g, 0.5 mmol) in DMF (5 mL), bromoacedaldehyde diethylacetal (0.15 mL, 1 mmol) was added and the contents were stirred at 100° C. for 8 h. The contents were brought to RT. Water was added and the product was extracted with ethyl acetate. The organic layer was separated and dried over anhydrous MgSO₄. The solvent was removed under reduced pressure to yield the title product.

Method E: Modification at Imidazole Position 1

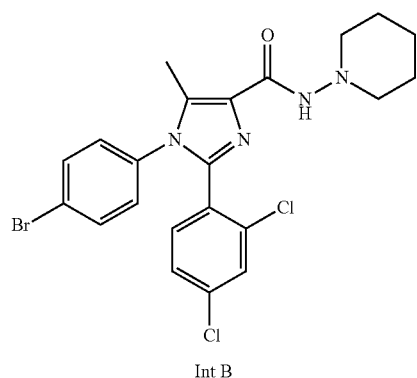

Int B

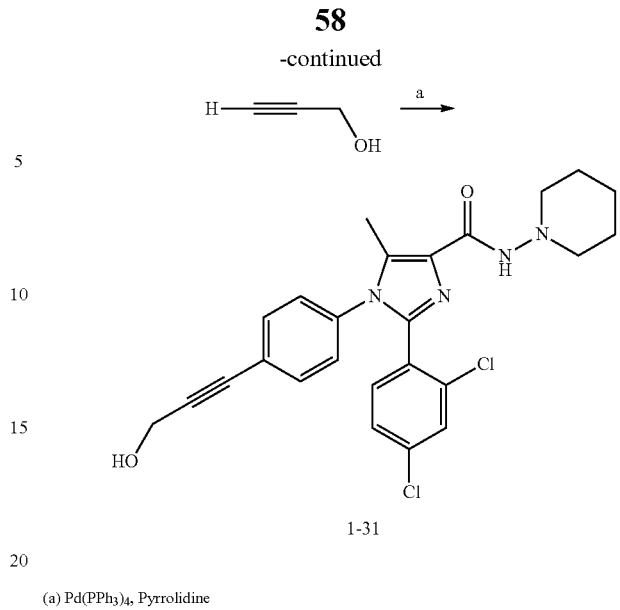

1-31

(a) Pd(PPh₃)₄, Pyrrolidine

To a stirred solution of Int B (0.5 g, 1 mmol) in pyrrolidine (15 mL), propargyl alcohol (0.05 g, 1 mmol) and Pd(PPh₃)₄ (0.11 g, 0.1 mmol) were added. The contents were stirred at 90° C. for 12 h. After cooling the reaction mixture to RT, water (50 mL) was added. The product was extracted with ethyl acetate. The organic layer was dried over anhydrous MgSO₄, filtered and evaporated under reduced pressure. Purification by column chromatography gave the product 1-31.

Method F: Modification at Imidazole Position 4

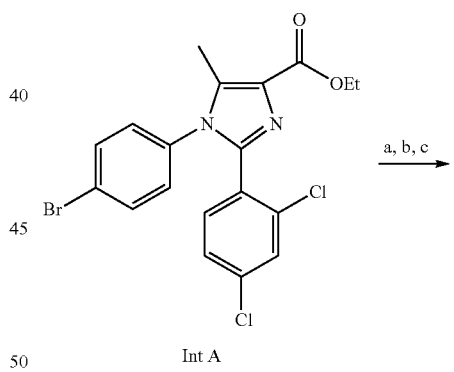

Int A

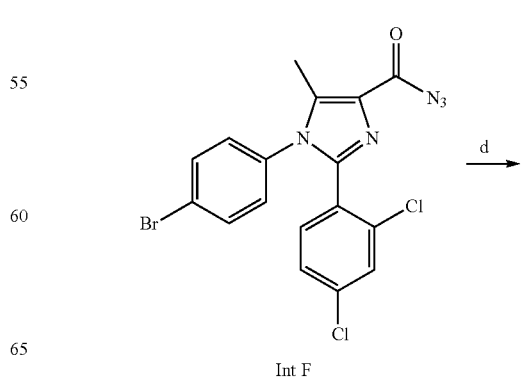

Int F

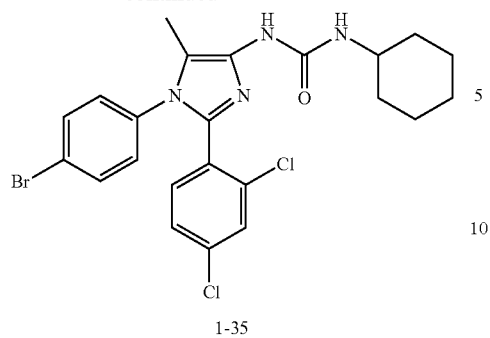

1-35

(a) LiOH, THF/MeOH/H₂O; (b) SOCl₂, toulene; (c) aq. NaN₃, THF; (d) cyclohexylamine, toulene;

Int. F. To a magnetically stirred solution of ester Int. A (0.626 g, 1.38 mmol) in THF: methanol:water (7:2:1, 15 mL) lithium hydroxide monohydrate (0.08 g, 2 mmol) was added. The mixture was heated under reflux for 3 h. The cooling reaction mixture was then poured into water (10 mL) and acidified with 10% hydrochloric acid. The precipitate was filtered, washed with water, and dried under vacuum to yield the corresponding acid as a solid.

A solution of the crude acid (0.585 g) and thionyl chloride (0.492 g, 4.14 mmol) in toluene (10 mL) was refluxed for 3 h. Solvent was evaporated under reduced pressure, and the residue was then redissolved in toluene (20 mL) and evaporated to yield the crude carboxylic chloride as a solid. To the solution of above carboxylic chloride (1.24 mmol) in THF (5 mL), NaN₃ (0.081 g, 1.24 mmol) in 0.5 mL of water was added at 0° C. The contents were stirred at that temperature for 1 hr. The reaction was quenched with water (5 mL), both aqueous and organic layers were separated. The organic layer was extracted using ethyl acetate (10 mL) and dried over anhydrous MgSO₄. The solvent was evaporated under reduced pressure to give the title product.

Compound 1-35. To a magnetically stirred solution of Int. F (0.448 g, 1 mmol) in toluene (10 mL) cyclohexyl amine (0.34 mL, 3 mmol) was added. The contents were stirred at 100° C. for 8 h. After cooling to room temperature the reaction was quenched by water (5 mL). Both aqueous and organic layers were separated, the organic layer was dried over anhydrous MgSO₄. The solvent was evaporated under reduced pressure. Purification by column chromatography gave the title product.

Method G: Modification at Imidazole Position 5

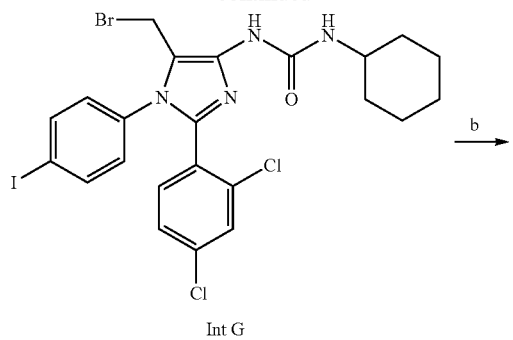

Int G

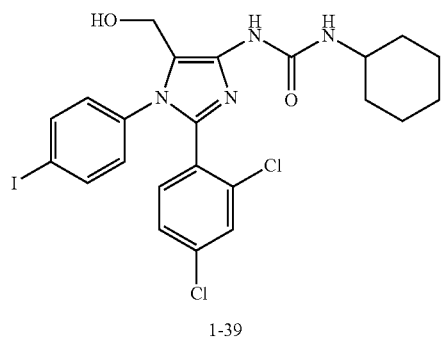

1-39

(a) NBS, AIBN, CCl₄, (b) DMSO, H₂O

Int. G. To a magnetically stirred solution of 1-36 (0.569 g, 1 mmol) in carbon tetrachloride (20 mL) was added N-bromosuccinimide (0.21 g, 1.2 mmol) and 2,2'-azobisisobutyronitrile (AIBN, 5 mg). The resulting mixture was refluxed for 3 h. After cooling to RT, the precipitate was filtered. The solvent was removed from the filtrate under reduced pressure to give the title product.

Compound 1-39. To the Int. G (0.648 g, 1 mmol), DMSO/H₂O (5:1) were added. The mixture was stirred at 60° C. for 5 h. After cooling to RT, water (30 mL) was added. The organic layer was extracted with ethyl acetate and dried over anhydrous MgSO₄. The solvent was removed under reduced pressure. Purification by column chromatography gave the title product.

Method H: Modification at Imidazole Position 5

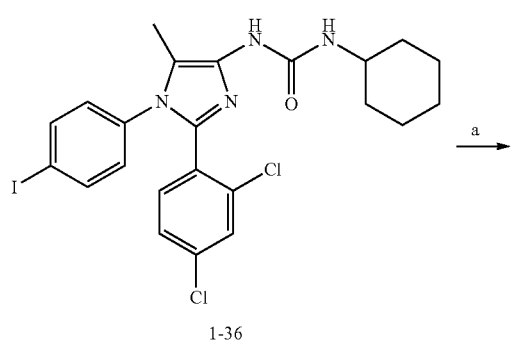

1-36

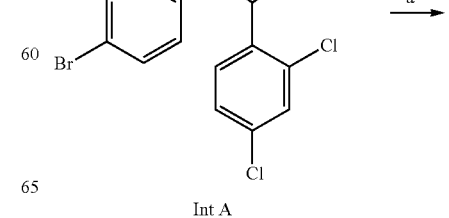

Int A

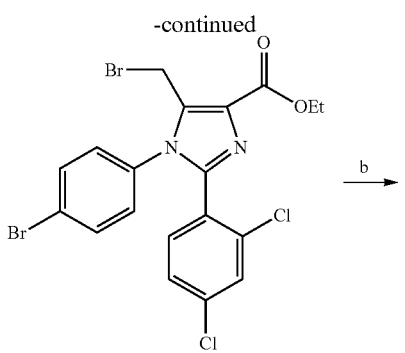

Int H

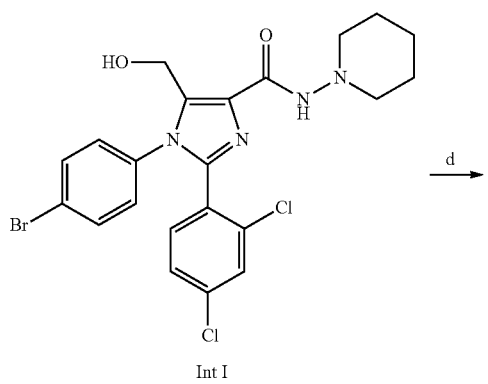

Int I

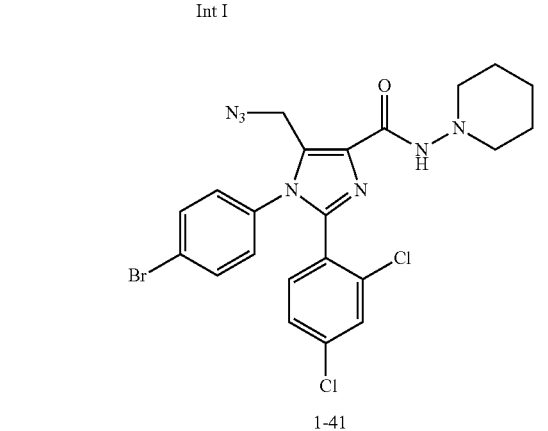

1-41

(a) NBS, AIBN, CCl₄; (b) DMSO/H₂O; (c) 1-aminopiperdine, AlCl₃, 1,2-dichloroethane
(d) Diphenylphosphoryl azide, DBU, toulene Int H To a magnetically stirred solution of Int A (0.454 g, 1 mmol) in carbon tetrachloride (20 mL) was added N-bromosuccinimide (0.21 g, 1.2 mmol) and 2,2'-azobisisobutyronitrile (AIBN, 5 mg). The resulting mixture was refluxed for 3 h. After cooling to RT, the precipitate was filtered. The solvent was removed from the filtrate under reduced pressure gave the bromo derivative, to which DMSO/H₂O (5:1) were added. The mixture was stirred at 60° C. for 5 h. After cooling to RT, water (30 mL) was added. The organic layer was extracted with ethyl acetate and dried over anhydrous MgSO₄. The solvent was removed under reduced pressure. Purification by column chromatography gave the title product.

Int I To the suspension of AlCl₃ (0.266 g, 2 mmol) in dichloroethane (20 mL) was added 1-aminopiperidine (0.6 mL, 6 mmol) at 0° C. and stirred for 25 min at that temperature. To this was added a solution of Int H (0.94 g, 2 mmol) in dichloroethane (5 mL). The reaction was brought to RT and stirred at that temperature for 8 h. The reaction was quenched with dil. HCl and the organic layer was extracted with dichloromethane. The combined extracts were dried over anhydrous MgSO₄, filtered and evaporated under reduced pressure. Purification by column chromatography gave the Int I.

Compound 1-41 A mixture of Int I (0.52 g, 1 mmol) and diphenyl phosphorazidate (DPPA) (0.25 mL, 1.2 mmol) was dissolved in anhydrous toluene (10 mL). The mixture was cooled to 0° C. under argon, and neat DBU (0.18 mL, 1.2 mmol) was added. The reaction was stirred for 2 h at 0° C. and then at RT for 16 h. The resulting two-phase mixture was washed with water and 5% HCl. The organic layer was extracted with ethyl acetate and dried over anhydrous MgSO₄. The solvent was removed under reduced pressure. Purification by column chromatography gave the product 1-41. See J. Org. Chem., 1993, 58, 5886, the contents of which are herein incorporated by reference.

Prophetic Methods

Methods 1-L are prophetic and are believed useful to prepare the inventive compounds of formulas II and III.

Method I: Modification at Pyrazole Positions 1, 3 and 5

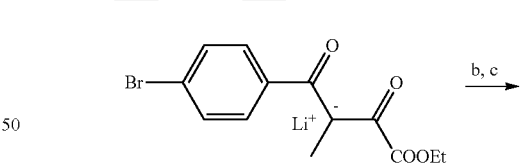

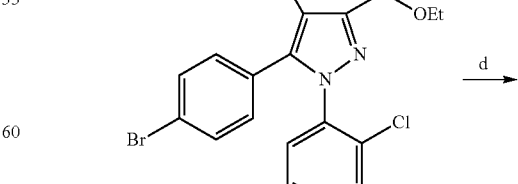

Int J

-continued

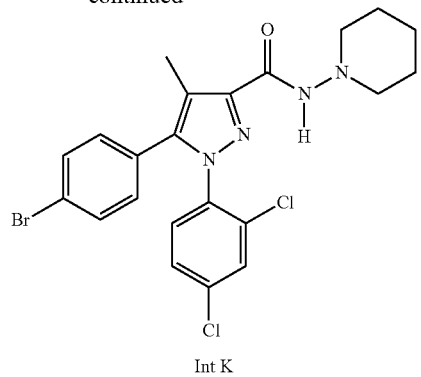

Int K (a) LiHMDS, ether, then EtO$_2$CCO$_2$Et; (b) 2,4-Dichlorophenylhydrazine hydrochloride, EtOH; (c) AcOH; (d) 1-Aminopiperidine, AlCl$_3$, 1,2-dichloroethane.

Lithium salt of ethyl
2,4-dioxo-3-methyl-4-(4-bromophenyl)butanoate

To a magnetically stirred solution of lithium bis(trimethylsilyl)amide (40 mL, 1.0 M solution in hexane, 40 mmol) in diethyl ether (120 mL) was added a solution of 4'-bromopropiophenone (8.52 g, 40 mmol) in diethyl ether (50 mL) at −78° C. After the mixture was stirred at the same temperature for an additional 45 min, diethyl oxalate (6.4 mL, 47 mmol) was added to the mixture. The reaction mixture was allowed to warm to room temperature (RT) and stirred for 16 h. The precipitate was filtered, washed with diethyl ether, and dried under vacuum to afford the lithium salt.

1-(2,4-Dichlorophenyl)-4-methyl-5-(4-bromophenyl)-1H-pyrazole-3-carboxylic acid, Ethyl Ester
(Int. J)

To a magnetically stirred solution of the above lithium salt (0.64 g, 2.0 mmol) in 10 mL of ethanol was added 2,4-dichlorophenylhydrazine hydrochloride (0.47 g, 2.2 mmol) at room temperature. The resulting mixture was stirred at room temperature for 20 h. The precipitate was filtered, washed with ethanol and diethyl ether, and then dried under vacuum to give a light yellow solid. This solid was dissolved in acetic acid (7 mL) and heated under reflux for 24 h. The reaction mixture was poured into cold water and extracted multiple times with ethyl acetate. The combined extracts were washed with water, saturated aqueous sodium bicarbonate, and brine, dried over anhydrous sodium sulfate, filtered, and evaporated. Purification by flash column chromatography on silica gel gave the expected ester Int. J N-(Piperidin-1-yl)-5-(4-bromophenyl)-1-(2,4-dichlorophenyl)-4-methyl-1H-pyrazole-3-carboxamide
(Int. K)

To the suspension of AlCl$_3$ (1.0 g, 8 mmol) in dichloroethane (20 mL) was added 1-aminopiperidine (1.2 mL, 12 mmol) at 0° C. and stirred for 25 min at that temperature. To this was added a solution of Int J (1.81 g, 4 mmol) in dichloroethane (5 mL). The reaction was brought to RT and stirred at that temperature for 8 h. The reaction was quenched with dilute HCl and the organic layer was extracted with dichloromethane. The combined extracts were dried over anhydrous MgSO$_4$, filtered and evaporated under reduced pressure. Purification by column chromatography gave the Int K.

Method J: Modification at Thiazole Positions 2, 4 and 5

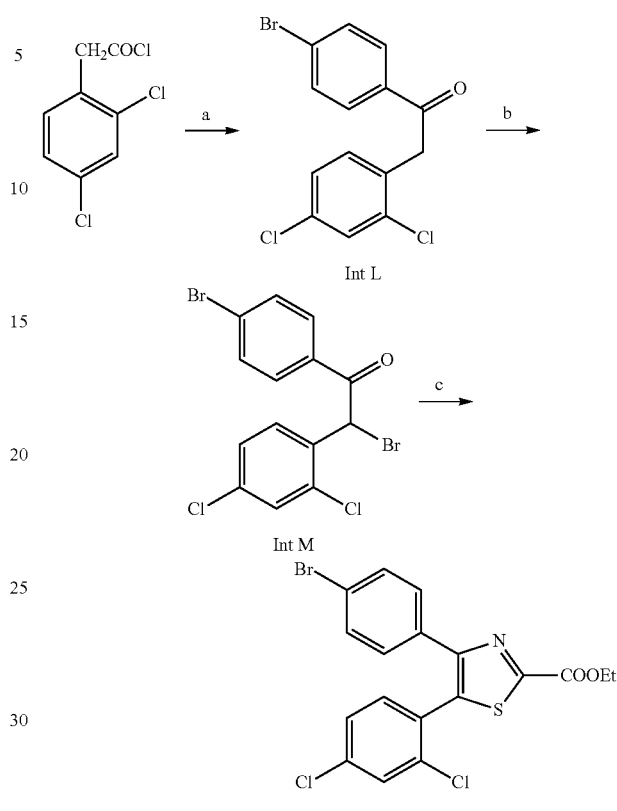

(a) AlCl$_3$, bromobenzene; (b) Br$_2$, CHCl$_3$; (C) ethyl thiooxamate, Ethanol 2-(2,4-dichlorophenyl)-1-(4-bromophenyl)ethanone
(Int L)

To the solution of 2,4-dichlorobenzyl chloride (2.33 g, 10 mmol) in bromobenzene at 0° C., AlCl$_3$ (1.72 g, 13 mmol) will be slowly added. The reaction mixture will be stirred overnight at room temperature. The reaction will be poured onto ice and extracted with ethyl acetate. The combined organic layers will be evaporated to yield the title compound.

2-Bromo-1-(4-bromophenyl)-2-(2,4-dichlorophenyl)ethanone (Int M)

To the stirring solution of Int L (3.44 g, 10 mmol) in chloroform (40 mL) bromine (1 mL, 15 mmol) will be added slowly. The contents will be stirred at 65-70° C. for 4 h. The reaction mixture will be brought to room temperature. Water will be added and the organic layer will be separated and dried over anhydrous MgSO$_4$. The evaporation of solvent will result in int M.

Ethyl-5-(2,4-dichlorophenyl)-4-(4-bromophenyl)thiazole-2-carboxylate (Int N)

Int M (4.2 g, 10 mmol) and ethyl thiooxamate (1.9 g, 15 mmol) will be dissolved in ethanol. The resulting solution will be heated at reflux temperature for 4-5 h. The reaction will be brought to room temperature and the solvent will be evaporated. The resulting crude will be purified by column chromatography to yield the title compound.

Method K: Modification at Oxazole Positions 2, 4 and 5

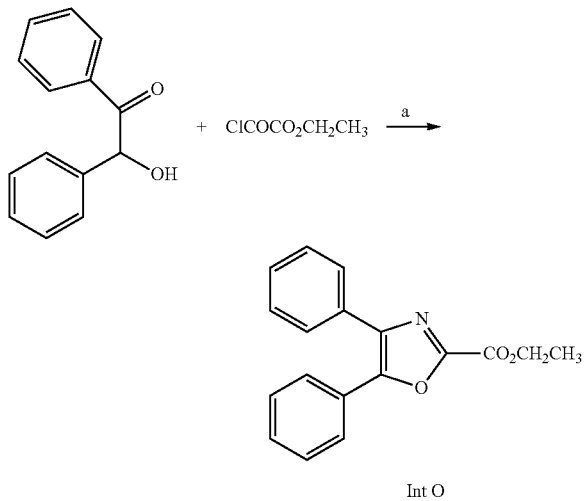

(a) NH₄OAC/ACOH

Ethyl 4,5-diphenyl-2-oxazolecarboxylate (Int O)

Ethyl oxalyl chloride (1.1 mL, 10 mmol) will be added dropwise to a stirring solution of 2-hydroxy-1,2-diphenyl ethanone (2.12 g, 10 mmol) and triethyl amine (2.2 mL, 16 mmol) in anhydrous THF (50 mL) under argon. After stirring for 45 min the mixture will be filtered and concentrated, and NH₄OAC (4 g, 50 mmol) and acetic acid (50 mL) will be added. The mixture will be heated to reflux for 6 h. The reaction will be brought to room temperature and water will be added and extracted with dichloromethane and the residue will be subjected to column chromatography to yield the title compound.

Method L: Modification at Triazole Positions 1, 3 and 5

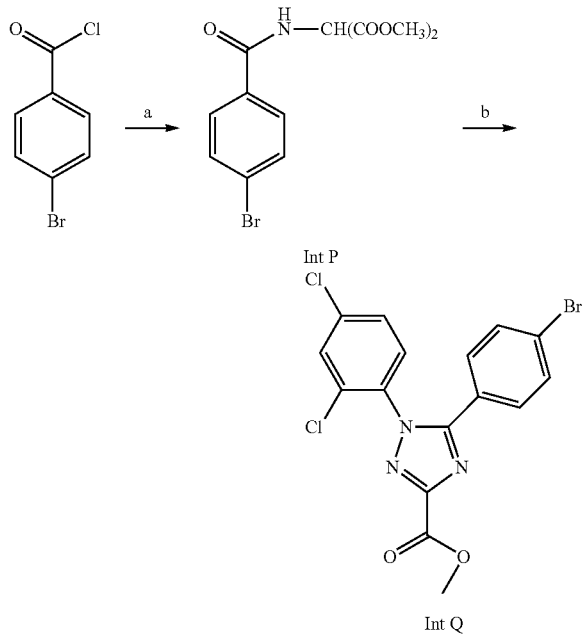

(a) dimethyl aminomalonate hydrochloride, Et₃N, CH₂Cl₂;
(b) 2,4-dichloroaniline, aq. HCl, AcOH, NaNO₂, NaOMe, Methanol

Dimethyl-2-(4-bromobenzoylamino)malonate (Int P)

To a stirred solution of dimethyl aminomalonate hydrochloride (1.83 g, 10 mmol) in dichloromethane (30 mL) triethylamine (3 mL, 22 mmol) will be added at 0° C. 4-bromobenzoyl chloride (2.19 g, 10 mmol) will be slowly added the resulting solution will be allowed to stand at room temperature overnight. Water will be added and the organic layer will be separated and dried over anhydrous MgSO₄. The evaporation of solvent will result in Int P.

Methyl 5-(4-bromophenyl)-1-(2,4-dichlorophenyl)-1H-1,2,4-triazole-3-carboxylate (Int Q)

To a stirred solution of 2,4-dichloroaniline (1.62 g, 10 mmol) in conc. HCl (5 mL) and acetic acid (30 mL) at 0° C. will be added a solution of NaNO₂ (0.69 g, 10 mmol) in water (10 mL) and resulting solution will be stirred for 15 min. A solution of Int P (2.37 g, 8.3 mmol) in acetone (20 mL) will be slowly added while keeping the temperature below 0° C. A solution of K₂CO₃ (1.2 g) in water (20 mL) will be slowly added and the resulting mixture will be stirred for 30 min at 0° C. The resulting mixture will be extracted with ethyl acetate. The organic layer will be washed with water and NaHCO₃ and dried over anhydrous MgSO₄. The solvent will be evaporated and dissolved in methanol and NaOMe will be added. The resulting mixture will be allowed stand overnight at room temperature and cooled in refrigerator. The title compound will precipitate out.

Method M: Modification at Pyrazole Positions 3 and 5

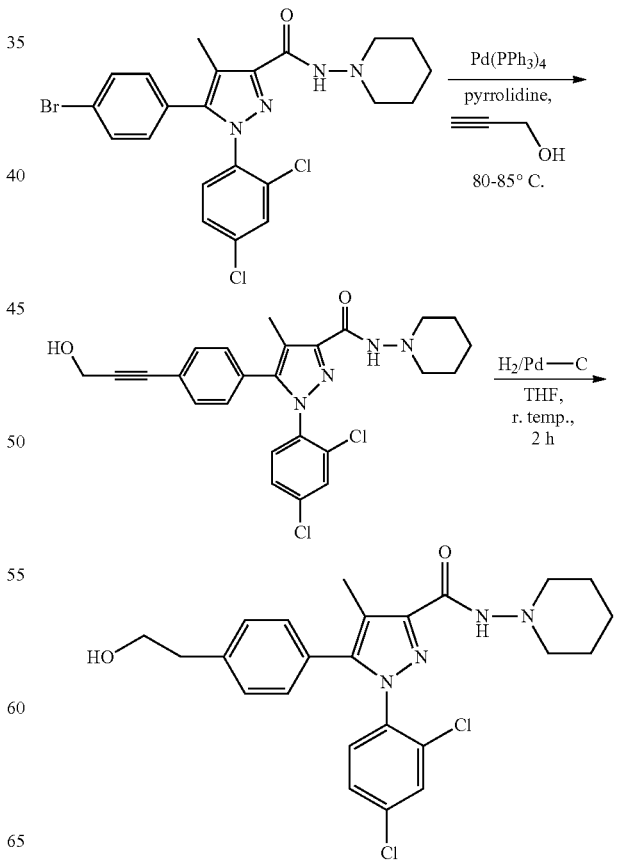

1-(2,4-Dichloro-phenyl)-5-[4-(3-hydroxy-prop-1-ynyl)-phenyl]-4-methyl-1H-pyrazole-3-carboxylic acid piperidin-1-ylamide (2-1)

To a stirred solution of 5-(4-Bromo-phenyl)-1-(2,4-dichloro-phenyl)-4-methyl-1H-pyrazole-3-carboxylic acid piperidin-1-ylamide (40 mg, 0.078 mmol) in pyrrolidine (2.5 ml) was added a catalytic amount of tetrakis(triphenylphosphine) palladium under an atmosphere of Argon. After stirring the contents for 5 min at room temperature, a solution of propargyl alcohol (10 mg, 0.178 m mol) in pyrrolidine (1.5 ml) was added to the reaction mixture. The contents were heated at 80-85° C. for 10 h. Then a saturated aqueous solution of ammonium chloride was added and the mixture was extracted with ethyl acetate. The organic extract was dried over MgSO$_4$ and the solvent was removed in vacuo. Purification by flash column chromatography on silica gel (petroleum ether-ethyl acetate, 7:3) afforded 28 mg (74%) of 2-1 as white solid.

1-(2,4-Dichloro-phenyl)-5-[4-(3-hydroxy-propyl)-phenyl]-4-methyl-1H-pyrazole-3-carboxylic acid piperidin-1-ylamide (4-1)

To a magnetically stirred suspension of 14 mg of palladium (10 wt % on carbon) taken in 8 ml of THF was added compound 2-1 (80 mg, 0.165 mmol) dissolved in 3 ml of THF. The resulting mixture was stirred at room temperature for 2 h under an atmosphere of hydrogen. Then to the mixture was added 10 ml of DCM and the catalyst was filtered and the residue was concentrated and purified by flash column chromatography (petroleum ether-ethyl acetate, 6:4) to afford 61 mg (76%) of 4-1 as a white solid.

Compounds 3-1 to 3-12 as shown in Table 3 and compounds 4-2 to 4-7 as shown in Table 4 were synthesized according to the above represented examples. Similarly compounds 5-1 to 5-21 shown in Table 5 were synthesized using other commercially available acetylenes.

Those skilled in the art will recognize, or be able to ascertain using no more than routine experimentation, many equivalents to specific embodiments of the invention described specifically herein. Such equivalents are intended to be encompassed in the scope of the invention.

What is claimed is:

1. A compound represented by the following structural formula,

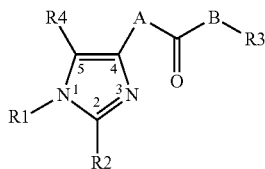

and physiologically acceptable salts thereof, wherein:
A is a direct bond;
B is N(R5),
R5 is selected from hydrogen, alkyl and substituted alkyl;
R1 and R2 are each independently —(CH$_2$)$_n$—Z,
n is 0, and
Z is selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or Z is selected from a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —(CH$_2$)$_n$— group and the Z group can be any available ring carbon atom or any available ring nitrogen atom; or Z is selected from 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or Z is selected from

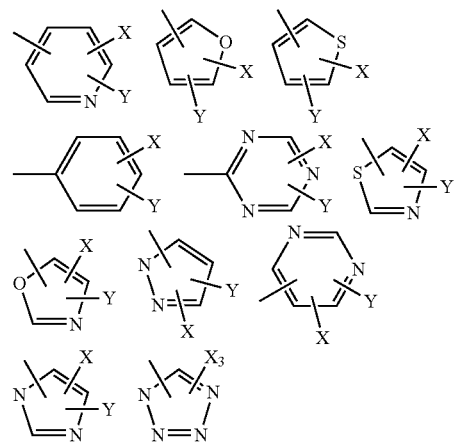

wherein X and Y are each independently selected from H, halogen, N$_3$, NCS, CN, NO$_2$, NX$_1$X$_2$, OX$_3$, OAc, O-acyl, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, alkyl, alcohol, alkoxy, alkylmercapto, alkylamino, di-alkylamino, alkylsulfinyl, alkylsulfonyl and methylene dioxy when Z comprises a structure having two adjacent carbon atoms, $X_1$ and $X_2$ are each independently selected from H and alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ is selected from H, alkyl, hydroxyloweralkyl and alkyl-$NX_1X_2$; or Z is selected from a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms; or Z is selected from an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 3 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members; or R1 and R2 are each independently -T-$(CH_2)_n$—Z, n is 0, T is selected from a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring and a heteropolycyclic ring, and Z is selected from H, halogen, $N_3$, NCS, CN, $NO_2$, $NX_1X_2$, $OX_3$, OAc, O-acyl, O-aroyl, $O(CH_2)_jOH$, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, alkoxy, alkylmercapto, alkylamino, di-alkylamino, alkylsulfinyl and alkylsulfonyl, $X_1$ and $X_2$ each independently is selected from H and alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ is selected from H, alkyl, hydroxyloweralkyl and or alkyl-$NX_1X_2$, j is an integer from 0 to about 6; or Z is selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or Z is selected from 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or Z is selected from

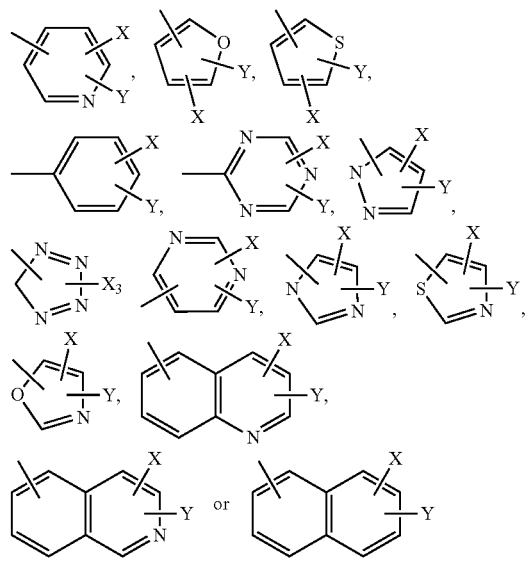

wherein X and Y are each independently selected from H, halogen, $N_3$, NCS, CN, $NO_2$, $NX_1X_2$, $OX_3$, OAc, O-acyl, O-aroyl, NH-acyl, NH-aroyl, CHO, C(halogen)$_3$, $COOX_3$, $SO_3H$, $SO_2NX_1X_2$, $CONX_1X_2$, alkyl, alcohol, alkoxy, alkylmercapto, alkylamino, di-alkylamino, alkylsulfinyl, alkylsulfonyl and methylene dioxy when Z comprises a structure having two adjacent carbon atoms, X₁ and X₂ are each independently is selected from H or alkyl, or X₁ and X₂ together comprise part of a heterocyclic ring having about 4 to about 7 ring members and optionally one additional heteroatom selected from O, N or S, or X₁ and X₂ together comprise part of an imide ring having about 5 to about 6 members, X₃ is selected from H, alkyl, hydroxyloweralkyl and alkyl-NX₁X₂; or Z is selected from an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members and an unsaturated ring having 6 ring atoms and 0 to 3 independently selected heteroatoms as ring members fused to an unsaturated ring having 6 or 7 ring atoms and 0 to 4 independently selected heteroatoms as ring members; or R1 and R2 are each independently -T-(CH₂)ₙ-Q₁-(CH₂)ₘ—Z, n is 0, m is an integer from 0 to about 7, T is selected from a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring and a heteropolycyclic ring, Q₁ is selected from NH, O, S, CH=CH, CO, SO₂ and OSO₂, and Z is selected from H, halogen, N₃, NCS, CN, NO₂, NX₁X₂, OX₃, OAc, O-acyl, O-aroyl, O(CH₂)ⱼOX₃, O(CH₂)ⱼNX₁X₂, NH-acyl, NH-aroyl, CHO, C(halogen)₃, COOX₃, SO₃H, SO₂NX₁X₂, CONX₁X₂, alkyl, alcohol, alkoxy, alkylmercapto, alkylamino or di-alkylamino, alkylsulfinyl and alkylsulfonyl, X₁ and X₂ each independently selected from H and alkyl, or X₁ and X₂ together comprise part of a heterocyclic ring having about 4 to about 7 ring members and optionally one additional heteroatom selected from O, N or S, or X₁ and X₂ together comprise part of an imide ring having about 5 to about 6 members, X₃ is selected from H, alkyl, hydroxyloweralkyl and alkyl-NX₁X₂, j is an integer from 0 to about 6; or Z is selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the (CHO, —(CH₂)ₘ— group and the Z group can be any available ring carbon atom or any available ring nitrogen atom; or Z is selected from 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH₂)ₘ— group and the Z group can be any available ring carbon atom or any available ring nitrogen atom; or Z is selected from

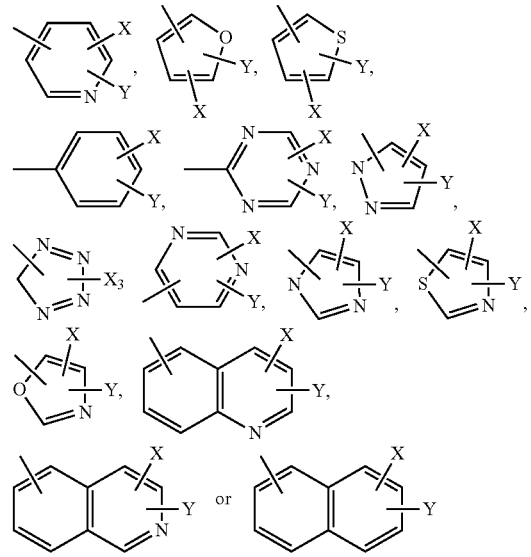

wherein X and Y are each independently is selected from H, halogen, N₃, NCS, CN, NO₂, NX₁X₂, OX₃, OAc, O-acyl, O-aroyl, O(CH₂)ⱼOX₃O (CH₂)ⱼNX₁X₂, NH-acyl, NH-aroyl, CHO, C(halogen)₃, COOX₃, SO₃H, SO₂NX₁X₂, CONX₁X₂, alkyl, alcohol, alkoxy, alkylmercapto, alkylamino, di-alkylamino, alkylsulfinyl, alkylsulfonyl and methylene dioxy when Z comprises a structure having two adjacent carbon atoms, X₁ and X₂ are each independently is selected from H and alkyl, or X₁ and X₂ together comprise part of a heterocyclic ring having about 4 to about 7 ring members and optionally one additional heteroatom selected from O, N or S, or X₁ and X₂ together comprise part of an imide ring having about 5 to about 6 members, X₃ is selected from H, alkyl, hydroxyloweralkyl and alkyl-NX₁X₂; or Z is selected from an unsaturated ring having 5 ring atoms and 0 to 2 independently selected heteroatoms as ring members fused to an unsaturated ring having 5 ring atoms and 0 to 2 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members; or Z is selected from

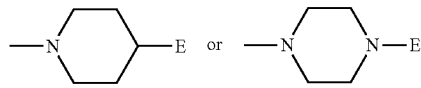

wherein E is selected from a C1 to about C4 linear or branched alkyl group, a phenyl group, a substituted phenyl group, a benzyl group and a substituted benzyl group; or Z is selected from

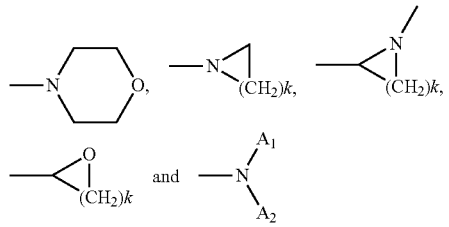

wherein k is an integer from 1 to about 5, $A_1$ and $A_2$ are each independently selected from a C1 to about C4 alkyl group, a phenyl group and a substituted phenyl group;

R3 is selected from a carbocyclic ring having about 4 to about 7 members, a heterocyclic ring having about 4 to about 7 members, an aromatic ring having about 5 to about 7 ring members, a heteroaromatic ring having about 5 to about 7 members, a bicyclic ring, a heterobicyclic ring, a tricyclic ring, a heterotricyclic ring, a polycyclic ring and a heteropolycyclic ring; or R3 is

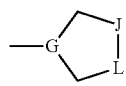

wherein G is selected from CH and N, and L and J each independently selected from $(CH_2)_n$, O, NH and S, n is an integer from 0 to about 7; or R3 is

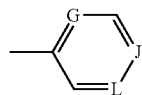

wherein G, L and J are each independently selected from CH and N; or

R3 is selected from

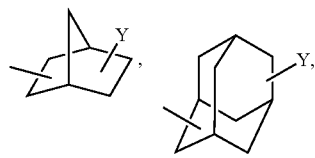

-continued

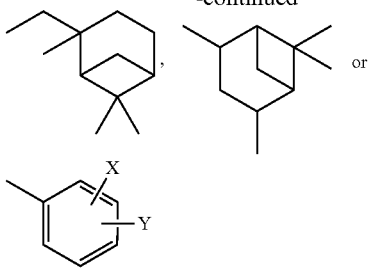

wherein X and Y are independently selected from H, halogen, $N_3$, NCS, phenyl, CN, $NO_2$, $NX_1X_2$, $OX_3$, OAc, O-acyl, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, alkyl, alcohol, alkoxy, alkylmercapto, alkylamino, di-alkylamino, alkylsulfinyl and alkylsulfonyl, $X_1$ and $X_2$ are each independently selected from H and alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members), $X_3$ is selected from H, alkyl, hydroxyloweralkyl and alkyl-$NX_1X_2$, j is an integer from 0 to about 6; or R3 is selected from a carbocyclic ring having 4 to 6 ring atoms fused to a heterocyclic ring having from 5 to 7 ring atoms, a carbocyclic ring having 4 to 6 ring atoms fused to a heteroaromatic ring having from 5 to 7 ring atoms, a heterocyclic ring having 6 ring atoms fused to a heterocyclic ring having from 5 to 7 ring atoms, a heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms, and a heteroaromatic ring having 6 ring atoms fused to a heteroaromatic ring having from 5 to 7 ring atoms;

R4 is selected from H, halogen, $N_3$, NCS, phenyl, CN, $NO_2$, $NX_1X_2$, $OX_3$, OAc, O-acyl, O-aroyl, $O(CH_2)_jOX_3$, $O(CH_2)_jNX_1X_2$, NH-acyl, NH-aroyl, CHO, $C(halogen)_3$, $COOX_3$, $SO_3H$, $SO_2NX_1X_2$, $CONX_1X_2$, alkyl, alcohol, alkoxy, alkylmercapto, alkylamino, di-alkylamino, alkylsulfinyl and alkylsulfonyl, $X_1$ and $X_2$ are each independently selected from H and alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members), $X_3$ is selected from H, alkyl, hydroxyloweralkyl and alkyl-$NX_1X_2$, j is an integer from 0 to about 6; or R4 is selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring and a heteropolycyclic ring; or R4 is selected from

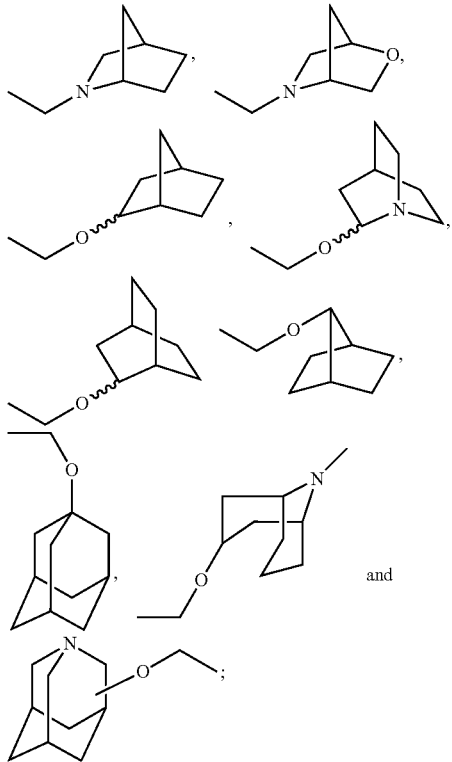

or

R4 is —(CH$_2$)$_d$—Z, d is an integer from 1 to about 6, and

Z is selected from H, halogen, N$_3$, NCS, phenyl, CN, NO$_2$, NX$_1$X$_2$, OX$_3$, OAc, O-acyl, O-aroyl, O(CH$_2$)$_j$OH, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, alkyl, alkoxy, alkylmercapto, alkylamino, di-alkylamino, alkylsulfinyl and alkylsulfonyl, X$_1$ and X$_2$ are each independently selected from H and alkyl, or X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members), X$_3$ is selected from H, alkyl, hydroxyloweralkyl and alkyl-NX$_1$ X$_2$, j is an integer from 0 to about 6; or Z is selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_d$— group and the Z group can be any available ring carbon atom or any available ring nitrogen atom; or Z is selected from 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_d$— group and the Z group can be any available ring carbon atom or any available ring nitrogen atom; or R4 is —(CH$_2$)$_p$-Q$_1$-(CH$_2$)$_q$—Z, Q$_1$ is selected from NH, O, S, CH=CH, CO, SO$_2$ and OSO$_2$, p is an integer from 1 to about 7, g is an integer from 0 to about 7, and Z is selected from H, halogen, N$_3$, NCS, phenyl, CN, NO$_2$, NX$_1$X$_2$, OX$_3$, OAc, O-acyl, O-aroyl, NH-acyl, NH-aroyl, O(CH$_2$)$_j$OX$_3$, O(CH$_2$)$_j$NX$_1$X$_2$, CHO, C(halogen)$_3$, COOX$_3$, SO$_3$H, SO$_2$NX$_1$X$_2$, CONX$_1$X$_2$, alkyl, alkoxy, alkylmercapto, alkylamino, di-alkylamino, alkylsulfinyl and alkylsulfonyl, X$_1$ and X$_2$ are each independently selected from H or alkyl, or X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ is selected from H, alkyl, hydroxyloweralkyl and alkyl-NX$_1$ X$_2$, j is an integer from 0 to about 6; or Z is selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_q$— group and the Z group can be any available ring carbon atom or any available ring nitrogen atom; or Z is selected from 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_q$— group and the Z group can be any available ring carbon atom or any available ring nitrogen atom; or Z is selected from

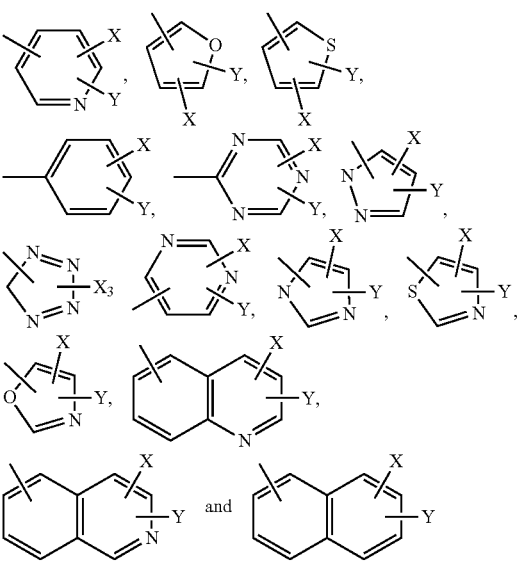

wherein X and Y are each independently selected from H, halogen, N$_3$, NCS, CN, NO$_2$, NX$_1$X$_2$, OX$_3$, OAc, O-acyl, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, alkyl, alcohol, alkoxy, alkylmercapto, alkylamino, di-alkylamino, alkylsulfinyl, alkylsulfonyl and methylene dioxy when Z comprises a structure having two adjacent carbon atoms, X$_1$ and X$_2$ are each independently selected from H and alkyl, or X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ is selected from H, alkyl, hydroxyloweralkyl and alkyl-NX$_1$X$_2$, J is an integer from 0 to about 6;

with the proviso that when either of R1 and R2 is phenyl [optionally substituted with one more members selected from halogen, (C$_1$-C$_6$) alkyl, (C$_1$-C$_6$) alkoxy, trifluoromethyl, cyano, nitro, (C$_1$-C$_6$) alkyl sulfonyl, (C$_1$-C$_6$) alkyl sulfonyl amino, (C$_1$-C$_6$) alkyl carbonyl-amino, (C$_1$-C$_6$) alkyl amino-carbonyl-amino and phenyl], (C$_2$-C$_6$) alkyl, cyclohexyl [optionally substituted with (C$_1$-C$_6$) alkyl, (C$_1$-C$_6$) alkoxy, trifluoromethyl, cyano or one or more fluorine atoms], 1-naphthyl or 2-naphthyl [optionally substituted with one or more members selected from halogen, (C$_1$-C$_6$) alkyl, (C$_1$-C$_6$) alkoxy, trifluoromethyl and cyano], benzyl [optionally substituted on the phenyl ring with one or more members selected from halogen, (C$_1$-C$_6$) alkyl, (C$_1$-C$_6$) alkoxy, trifluoromethyl and cyano], a 5- to 10-membered saturated or unsaturated heterocyclic radical [optionally substituted with one or more members selected from fluorine, (C$_1$-C$_6$) alkyl, (C$_1$-C$_6$) alkoxy, trifluoromethyl and cyano] and a 5- to 10-membered aromatic monocyclic or bicyclic heterocyclic radical [optionally substituted with one more members selected form halogen, (C$_1$-C$_6$) alkyl, (C$_1$-C$_6$) alkoxy, trifloromethyl, cyano, nitro and phenyl]; then R4 can not be H, (C$_1$-C$_6$) alkyl, benzyl, chloro, or bromo; and the proviso that when either R1 or R2 is phenyl, thienyl, 2-pyridinyl, 3-pyridinyl, 4-pyridinyl, pyrimidinyl, pyrazinyl, pyridazinyl, triazinyl or any above group substituted with 1, 2, 3 or 4 substituents which can be the same or different, selected from C$_{1-3}$ alkyl, C$_{1-3}$ alkoxy, hydroxy, halogen, trifluoromethyl, trifluoromethylthio, trifluoromethoxy, nitro, amino, mono- or dialkyl(C$_{1-2}$)-amino, mono- or dialkyl(C$_{1-2}$)-amido, (C$_{1-3}$)-alkoxycarbonyl, carboxyl, cyano, carbornyl, acetyl and naphthyl; then R4 can not be H, halogen, CN, carbornyl, formyl, acetyl, trifluoroacetyl, fluoroacetyl, propionyl, sulfamoyl, methanesulfonyl, methylsulfanyl, branched or unbranched C$_{1-4}$ alkyl group, which C$_{1-4}$ alkyl group may be substituted with 1 to 3 fluoro atoms or with a single bromo, chloro, iodo, cyano or hydroxy group.

2. A pharmaceutical preparation comprising a therapeutically effective amount of at least one of the compounds of claim 1 wherein the compound is in isolated and substantially purified form and at least one member selected from an excipient, a vehicle, an adjuvant, a flavoring, a colorant, or a preservative.

3. The compound of claim 1 wherein at least one of R1 or R2 is -T-(CH$_2$)$_n$—Z.

4. The compound of claim 1 wherein at least one of R1 or R2 is -T-(CH$_2$)$_n$-Q$_1$-(CH$_2$)$_m$—Z.

5. The compound of claim 1 wherein R3 is selected from a heterocyclic ring having about 4 to about 7 members, a heteroaromatic ring having about 5 to about 7 members, a bicyclic ring, a heterobicyclic ring, a tricyclic ring, a heterotricyclic ring, a polycyclic ring and a heteropolycyclic ring.

6. The compound of claim 1 wherein R4 is selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring and a heteropolycyclic ring.

7. The compound of claim 1, wherein
R1 is -T-(CH$_2$)$_n$-Q$_1$-(CH$_2$)$_m$—Z;
T is selected from an aromatic ring or a heteroaromatic ring; and
Q$_1$ is C≡C.

8. The compound of claim 1, wherein
R1 is -T-(CH$_2$)$_n$-Q$_1$-(CH$_2$)$_m$—Z;
T is selected from an aromatic ring;
Q$_1$ is C≡C; and
R2 is selected from

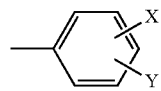

wherein X and Y are each independently selected from H, halogen, N$_3$, NCS, CN, NO$_2$, NX$_1$X$_2$, OX$_3$, OAc, O-acyl, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, alkyl, alcohol, alkoxy, alkylmercapto, alkylamino, di-alkylamino, alkylsulfinyl, alkylsulfonyl and methylene dioxy when Z comprises a structure having two adjacent carbon atoms, X$_1$ and X$_2$ are each independently selected from H and alkyl, or X$_1$ and X$_2$ together comprise part of a heterocyclic ring having 4 to 7 ring members and optionally one additional heteroatom selected from O, N or S, or X$_1$ and X$_2$ together comprise part of an imide ring having 5 to 6 members, X$_3$ is selected from H, alkyl, hydroxyloweralkyl and alkyl-NX$_1$X$_2$.

9. The compound of claim 8, wherein

R4 is selected from H, halogen, N$_3$, NCS, phenyl, CN, NO$_2$, NX$_1$X$_2$, OX$_3$, OAc, O-acyl, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, alkyl, alcohol, alkoxy, alkylmercapto, alkylamino, di-alkylamino, alkylsulfinyl and alkylsulfonyl, X$_1$ and X$_2$ are each independently selected from H and alkyl, or X$_1$ and X$_2$ together comprise part of a heterocyclic ring having 4 to 7 ring members and optionally one additional heteroatom selected from O, N or S, or X$_1$ and X$_2$ together comprise part of an imide ring having 5 to 6 members), X$_3$ is selected from H, alkyl, hydroxyloweralkyl and alkyl-NX$_1$X$_2$, j is an integer from 0 to 6; or R4 is —(CH$_2$)$_d$—Z, d is an integer from 1 to 6, and Z is selected from H, CN, OX$_3$, O(CH$_2$)$_j$OX$_3$, O(CH$_2$)$_j$NX$_1$X$_2$, NH—C(halogen)$_3$, alkyl, alkoxy, alkylmercapto, alkylsulfinyl and alkylsulfonyl, X$_1$ and X$_2$ are each independently selected from H and alkyl, or X$_1$ and X$_2$ together comprise part of a heterocyclic ring having 4 to 7 ring members and optionally one additional heteroatom selected from O, N or S, or X$_1$ and X$_2$ together comprise part of an imide ring having 5 to 6 members), X$_3$ is selected from H, alkyl, hydroxyloweralkyl and alkyl-NX$_1$X$_2$, j is an integer from 0 to 6.

10. The compound of claim 1, wherein

R1 is -T-(CH$_2$)$_n$-Q$_1$-(CH$_2$)$_m$—Z;

T is selected from a heteroaromatic ring;

Q$_1$ is C≡C; and

R2 is selected from wherein X and Y are each independently selected from H, halogen, N$_3$, NCS, CN, NO$_2$, NX$_1$X$_2$, OX$_3$, OAc, O-acyl, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, alkyl, alcohol, alkoxy, alkylmercapto, alkylamino, di-alkylamino, alkylsulfinyl, alkylsulfonyl and methylene dioxy when Z comprises a structure having two adjacent carbon atoms, X$_1$ and X$_2$ are each independently selected from H and alkyl, or X$_1$ and X$_2$ together comprise part of a heterocyclic ring having 4 to 7 ring members and optionally one additional heteroatom selected from O, N or S, or X$_1$ and X$_2$ together comprise part of an imide ring having 5 to 6 members, X$_3$ is selected from H, alkyl, hydroxyloweralkyl and alkyl-NX$_1$X$_2$.

11. The compound of claim 10, wherein

R4 is selected from H, halogen, N$_3$, NCS, phenyl, ON, NO$_2$, NX$_1$X$_2$, OX$_3$, OAc, O-acyl, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, alkyl, alcohol, alkoxy, alkylmercapto, alkylamino, di-alkylamino, alkylsulfinyl and alkylsulfonyl, X$_1$ and X$_2$ are each independently selected from H and alkyl, or X$_1$ and X$_2$ together comprise part of a heterocyclic ring having 4 to 7 ring members and optionally one additional heteroatom selected from O, N or S, or X$_1$ and X$_2$ together comprise part of an imide ring having 5 to 6 members), X$_3$ is selected from H, alkyl, hydroxyloweralkyl and alkyl-NX$_1$X$_2$, j is an integer from 0 to 6; or R4 is —(CH$_2$)$_d$—Z, d is an integer from 1 to 6, and Z is selected from H, CN, OX$_3$, O(CH$_2$)$_j$OX$_3$, O(CH$_2$)$_j$NX$_1$X$_2$, NH—C(halogen)$_3$, alkyl, alkoxy, alkylmercapto, alkylsulfinyl and alkylsulfonyl, X$_1$ and X$_2$ are each independently selected from H and alkyl, or X$_1$ and X$_2$ together comprise part of a heterocyclic ring having 4 to 7 ring members and optionally one additional heteroatom selected from O, N or S, or X$_1$ and X$_2$ together comprise part of an imide ring having 5 to 6 members), X$_3$ is selected from H, alkyl, hydroxyloweralkyl and alkyl-NX$_1$ X$_2$, j is an integer from 0 to 6.

12. The compound of claim 8, wherein

R3 is selected from a carbocyclic ring having 4 to 7 members, a heterocyclic ring having 4 to 7 members, an aromatic ring having 5 to 7 ring members, a heteroaromatic ring having 5 to 7 members, a bicyclic ring, a heterobicyclic ring, a tricyclic ring, a heterotricyclic ring, a polycyclic ring and a heteropolycyclic ring.

13. The compound of claim 10, wherein

R3 is selected from a carbocyclic ring having 4 to 7 members, a heterocyclic ring having 4 to 7 members, an aromatic ring having 5 to 7 ring members, a heteroaromatic ring having 5 to 7 members, a bicyclic ring, a heterobicyclic ring, a tricyclic ring, a heterotricyclic ring, a polycyclic ring and a heteropolycyclic ring.

14. The compound of claim 1, wherein

R1 is -T-(CH$_2$)$_n$-Q$_1$-(CH$_2$)$_m$—Z,

T is phenyl; and

Q$_1$ is C≡C.

15. The compound of claim 1, wherein

R1 is -T-(CH$_2$)$_n$-Q$_1$-(CH$_2$)$_m$—Z,

T is thienyl; and

Q$_1$ is C≡C.

16. The compound of claim 1, wherein
R1 is -T-(CH$_2$)$_n$—Z,
T is phenyl; and
Z is heteroaromatic.
17. The compound of claim 1 and physiologically accepted salts thereof, selected from one of the following structures:
1-14
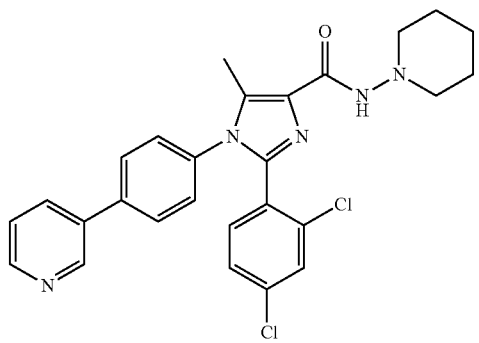 [SMILES: Cc1c(C(=O)NN2CCCCC2)nc(-c2ccc(Cl)cc2Cl)n1-c1ccc(-c2cccnc2)cc1]
1-15
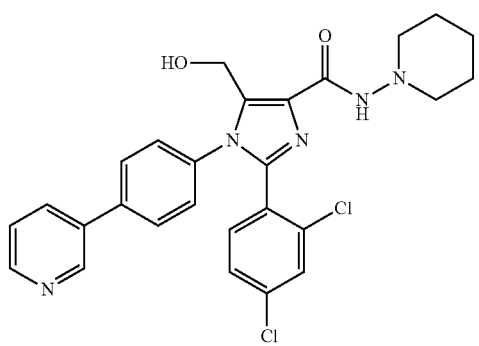 [SMILES: O=C(NN1CCCCC1)c1nc(-c2ccc(Cl)cc2Cl)n(-c2ccc(-c3cccnc3)cc2)c1CO]
1-16
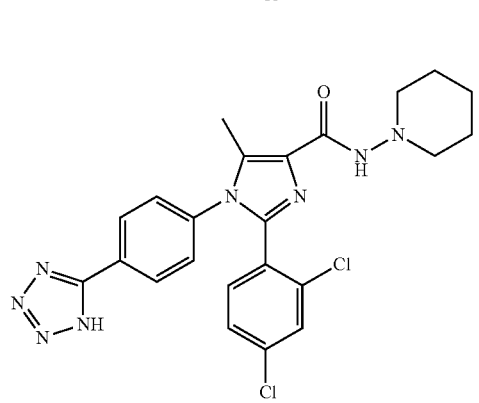 [SMILES: Cc1c(C(=O)NN2CCCCC2)nc(-c2ccc(Cl)cc2Cl)n1-c1ccc(-c2nnn[nH]2)cc1]
1-17
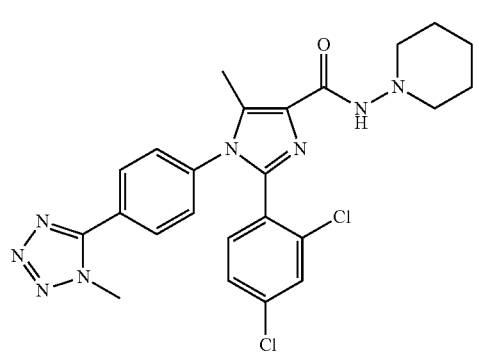 [SMILES: Cc1c(C(=O)NN2CCCCC2)nc(-c2ccc(Cl)cc2Cl)n1-c1ccc(-c2nnnn2C)cc1]
-continued
1-18
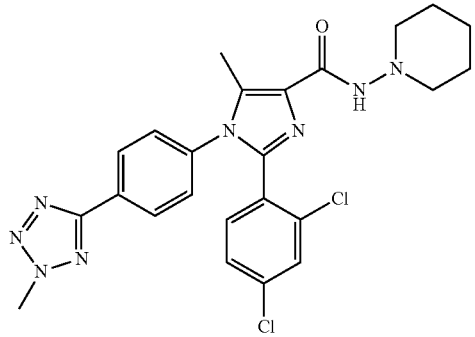 [SMILES: Cc1c(C(=O)NN2CCCCC2)nc(-c2ccc(Cl)cc2Cl)n1-c1ccc(-c2nnn(C)n2)cc1]
1-19
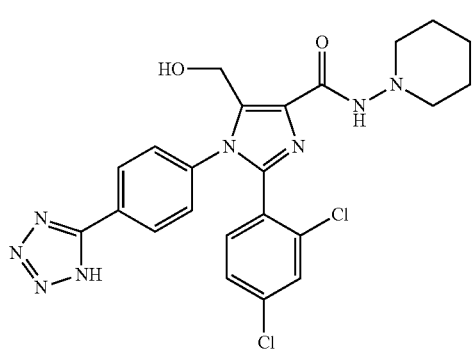 [SMILES: O=C(NN1CCCCC1)c1nc(-c2ccc(Cl)cc2Cl)n(-c2ccc(-c3nnn[nH]3)cc2)c1CO]
1-20
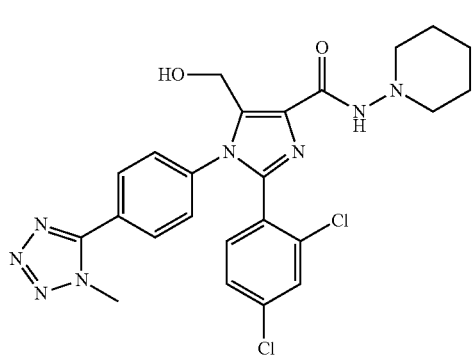 [SMILES: Cn1nnnc1-c1ccc(-n2c(-c3ccc(Cl)cc3Cl)nc(C(=O)NN3CCCCC3)c2CO)cc1]
1-21
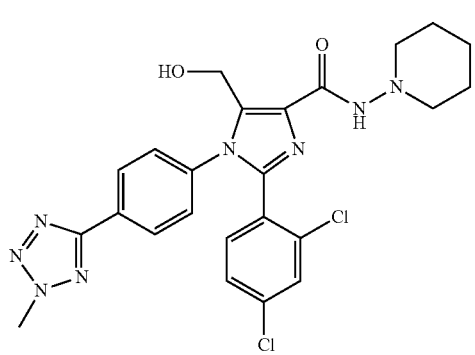 [SMILES: Cn1nnc(-c2ccc(-n3c(-c4ccc(Cl)cc4Cl)nc(C(=O)NN4CCCCC4)c3CO)cc2)n1]

1-22
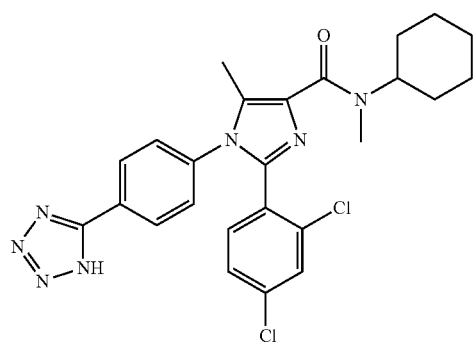 [SMILES: Cc1c(C(=O)N(C)C2CCCCC2)nc(-c2ccc(Cl)cc2Cl)n1-c1ccc(-c2nnn[nH]2)cc1]
1-23
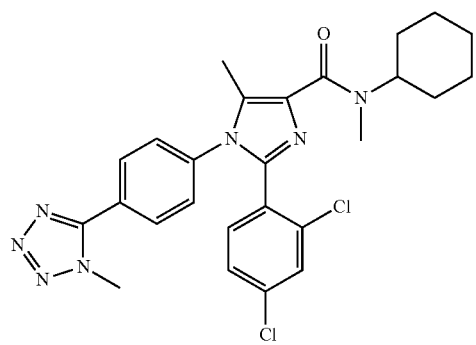 [SMILES: Cc1c(C(=O)N(C)C2CCCCC2)nc(-c2ccc(Cl)cc2Cl)n1-c1ccc(-c2nnnn2C)cc1]
1-24
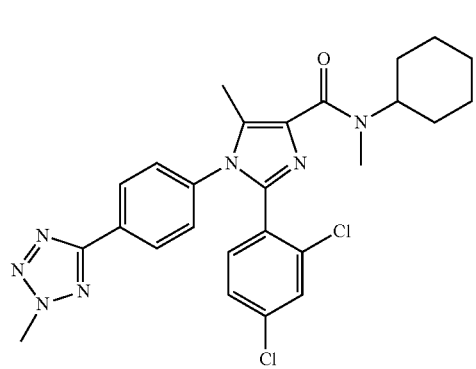 [SMILES: Cc1c(C(=O)N(C)C2CCCCC2)nc(-c2ccc(Cl)cc2Cl)n1-c1ccc(-c2nnn(C)n2)cc1]
1-25
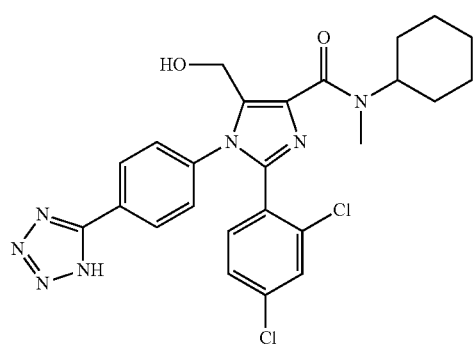 [SMILES: CN(C(=O)c1nc(-c2ccc(Cl)cc2Cl)n(-c2ccc(-c3nnn[nH]3)cc2)c1CO)C1CCCCC1]
1-26
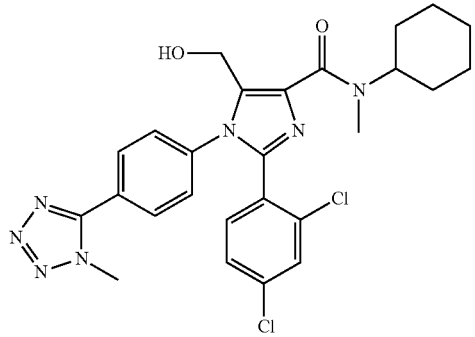 [SMILES: CN(C(=O)c1nc(-c2ccc(Cl)cc2Cl)n(-c2ccc(-c3nnnn3C)cc2)c1CO)C1CCCCC1]
1-27
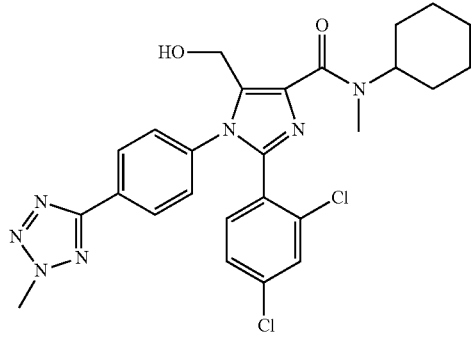 [SMILES: CN(C(=O)c1nc(-c2ccc(Cl)cc2Cl)n(-c2ccc(-c3nnn(C)n3)cc2)c1CO)C1CCCCC1]
1-28
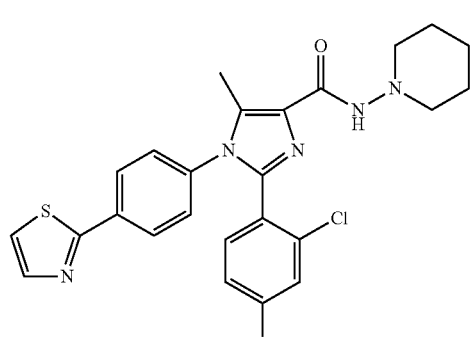
1-30
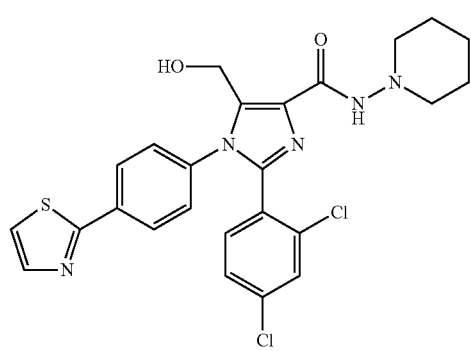 [SMILES: O=C(NN1CCCCC1)c1nc(-c2ccc(Cl)cc2Cl)n(-c2ccc(-c3nccs3)cc2)c1CO]

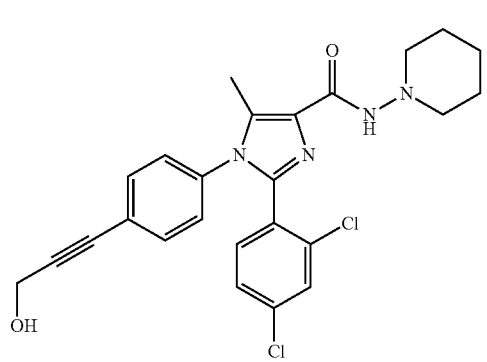 [SMILES: Cc1c(C(=O)NN2CCCCC2)nc(-c2ccc(Cl)cc2Cl)n1-c1ccc(C#CCO)cc1]
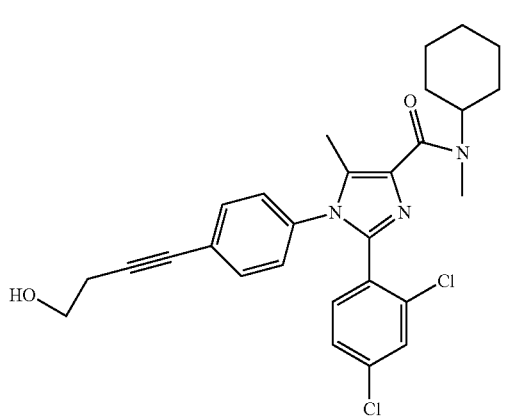
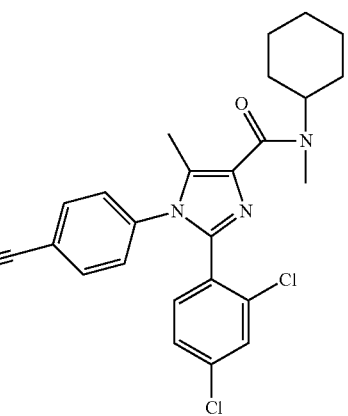

-continued

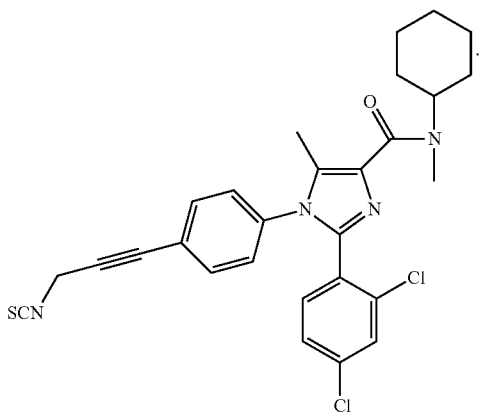

18. The compound of claim 1, wherein
R1 and R2 are each independently -T-(CH$_2$)$_n$—Z,
  T is selected from the group consisting of an aromatic ring and a heteroaromatic ring; and
  Z is a heteroaromatic ring.

19. The compound of claim 18, wherein R4 is selected from the group consisting of —CH$_3$, —CH$_2$CH$_3$, CN, —S-alkyl, —SO$_2$-alkyl and —O-alkyl.

20. The compound of claim 7 wherein R4 is selected from the group consisting of —CH$_3$, —CH$_2$CH$_3$, CN, —S-alkyl, —SO$_2$-alkyl and —O-alkyl.

* * * * *

UNITED STATES PATENT AND TRADEMARK OFFICE
CERTIFICATE OF CORRECTION

Page 1 of 2

PATENT NO. : 8,410,097 B2
APPLICATION NO. : 13/334163
DATED : April 2, 2013
INVENTOR(S) : Makriyannis et al.

It is certified that error appears in the above-identified patent and that said Letters Patent is hereby corrected as shown below:

In the Claims

Column 67, between lines 63 and 64:
insert
-- Z is selected from H, halogen, N3, NCS, CN, NO2, NX1X2, OX3, OAc, O-acyl, O-aroyl, O(CH2)jOX3, O(CH2)jNX1X2, NH-acyl, NH-aroyl, CHO, C(halogen)3, COOX3, SO3H, SO2NX1X2, CONX1X2, alkoxy, alkylmercapto, alkylamino, di-alkylamino, alkylsulfinyl and alkylsulfonyl,
   X1 and X2 are each independently selected from H or alkyl, or
   X1 and X2 together comprise part of a heterocyclic ring having about 4 to about 7 ring members and optionally one additional heteroatom selected from O, N or S, or
   X1 and X2 together comprise part of an imide ring having about 5 to about 6 members,
   X3 is selected from H, alkyl, hydroxyloweralkyl and alkyl-NX1X2,
   j is an integer from 0 to about 6; --

Column 71, line 37:
after "CH=CH" insert -- C≡C --

Column 71, line 67:
delete "(CHO,"

Column 76, line 23:
after "CH=CH" insert -- C≡C --

Column 76, line 26:
delete "g" and insert -- q --

Column 78, lines 18-19:
delete "carbornyl" and insert -- carbonyl --

Signed and Sealed this
Twentieth Day of August, 2013

Teresa Stanek Rea
*Acting Director of the United States Patent and Trademark Office*

CERTIFICATE OF CORRECTION (continued)
U.S. Pat. No. 8,410,097 B2

In the Claims

Column 80, line 15:
delete "ON" and insert -- CN --

UNITED STATES PATENT AND TRADEMARK OFFICE
CERTIFICATE OF CORRECTION

PATENT NO. : 8,410,097 B2
APPLICATION NO. : 13/334163
DATED : April 2, 2013
INVENTOR(S) : Makriyannis et al.

It is certified that error appears in the above-identified patent and that said Letters Patent is hereby corrected as shown below:

In the Claims

Column 67, between lines 63 and 64 substitute as shown:

-- Z is selected from H, halogen, $N_3$, NCS, CN, $NO_2$, $NX_1X_2$, $OX_3$, OAc, O-acyl, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, alkoxy, alkylmercapto, alkylamino, di-alkylamino, alkylsulfinyl and alkylsulfonyl,
    $X_1$ and $X_2$ are each independently selected from H or alkyl, or
    $X_1$ and $X_2$ together comprise part of a heterocyclic ring having about 4 to about 7 ring members and optionally one additional heteroatom selected from O, N or S, or
    $X_1$ and X2 together comprise part of an imide ring having about 5 to about 6 members,
    $X_3$ is selected from H, alkyl, hydroxyloweralkyl and alkyl-$NX_1X_2$,
    j is an integer from 0 to about 6; --

Column 71, line 37:
after "CH=CH" insert -- C≡C --

Column 71, line 67:
delete "(CHO,"

Column 76, line 23:
after "CH=CH" insert -- C≡C --

Column 76, line 26:
delete "g" and insert -- q --

This certificate supersedes the Certificate of Correction issued August 20, 2013.

Signed and Sealed this
Tenth Day of December, 2013

Margaret A. Focarino
*Commissioner for Patents of the United States Patent and Trademark Office*

CERTIFICATE OF CORRECTION (continued)
U.S. Pat. No. 8,410,097 B2

In the Claims

Column 78, lines 18-19:
delete "carbornyl" and insert -- carbonyl --

Column 78, line 20:
delete "carbornyl" and insert -- carbonyl --

Column 80, line 15:
delete "ON" and insert -- CN --